US011865188B2

(12) United States Patent
Pykett et al.

(10) Patent No.: US 11,865,188 B2
(45) Date of Patent: *Jan. 9, 2024

(54) GENE THERAPY FOR AADC DEFICIENCY

(71) Applicant: National Taiwan University, Taipei (TW)

(72) Inventors: Mark Pykett, Cambridge, MA (US); Richard Thorn, Mendon, MA (US); Wuh-Liang ("Paul") Hwu, Taipei (TW)

(73) Assignee: National Taiwan University, Taipei (TW)

( * ) Notice: Subject to any disclaimer, the term of this patent is extended or adjusted under 35 U.S.C. 154(b) by 272 days.

This patent is subject to a terminal disclaimer.

(21) Appl. No.: 17/157,745

(22) Filed: Jan. 25, 2021

(65) Prior Publication Data

US 2021/0236653 A1    Aug. 5, 2021

Related U.S. Application Data

(63) Continuation of application No. 15/951,270, filed on Apr. 12, 2018, now Pat. No. 10,898,585.

(60) Provisional application No. 62/485,658, filed on Apr. 14, 2017.

(51) Int. Cl.
| A61K 48/00 | (2006.01) |
| A61P 25/00 | (2006.01) |
| A61K 9/51 | (2006.01) |
| A61K 31/5513 | (2006.01) |
| C12N 15/62 | (2006.01) |
| C12N 15/85 | (2006.01) |
| C12N 15/113 | (2010.01) |
| A61K 31/4515 | (2006.01) |
| C12N 15/86 | (2006.01) |
| C12N 9/88 | (2006.01) |
| C12N 15/864 | (2006.01) |

(52) U.S. Cl.
CPC .......... *A61K 48/005* (2013.01); *A61K 9/5184* (2013.01); *A61K 31/4515* (2013.01); *A61K 31/5513* (2013.01); *A61K 48/00* (2013.01); *A61K 48/0075* (2013.01); *A61K 48/0083* (2013.01); *A61P 25/00* (2018.01); *C12N 9/88* (2013.01); *C12N 15/113* (2013.01); *C12N 15/625* (2013.01); *C12N 15/8509* (2013.01); *C12N 15/86* (2013.01); *C12N 15/8645* (2013.01); *C12Y 401/01028* (2013.01)

(58) Field of Classification Search
None
See application file for complete search history.

(56) References Cited

U.S. PATENT DOCUMENTS

| 5,254,079 A | 10/1993 | Agbodoe et al. |
| 5,334,394 A | 8/1994 | Kossovsky et al. |
| 5,985,583 A | 11/1999 | Sealfon |
| 6,309,634 B1 | 10/2001 | Bankiewicz et al. |
| 6,420,415 B1 | 7/2002 | Yamashita et al. |
| 6,503,888 B1 | 1/2003 | Kaplitt et al. |
| 6,506,378 B1 | 1/2003 | Kang |
| 6,953,575 B2 | 10/2005 | Bankiewicz et al. |
| 7,071,172 B2 | 7/2006 | McCown et al. |
| 7,115,258 B2 | 10/2006 | Kang |
| 7,182,944 B2 | 2/2007 | Bankiewicz |
| 7,378,273 B2 | 5/2008 | Bleck |

(Continued)

FOREIGN PATENT DOCUMENTS

| WO | 2017023724 | 2/2017 |
| WO | 2018191450 | 10/2018 |

(Continued)

OTHER PUBLICATIONS

McInerney and Roberts (Mt. Sinai K Med Sep. 2000; 67(4):300-310, abstract provided (Year: 2000).*
Samaranch et al. Gene Therapy 23:393-398 (Year: 2016).*
Sebastian et al. Molecular Therapy—Methods & Clinical Development 3:14049. pp. 1-10, 2014 (Year: 2014).*
Aalbers et al., "Empty capsids and macrophage inhibition/depletion increase rAAV-transgene expression in joints of both healthy and arthritic mice,." Human Gene Therapy, 2017, pp. 168-178, vol. 28, No. 2.
Abeling et al., "Pathobiochemical implications of hyperdopaminuria in patients with aromatic L-amino acid decarboxylase defidency." J. Inherit Metab. Dis, 2000, pp. 325-328,. vol. 23.

(Continued)

*Primary Examiner* — Marcia S Noble
(74) *Attorney, Agent, or Firm* — Polsinelli, PC

(57) ABSTRACT

The present invention is directed to compositions and methods for treating aromatic L-amino acid decarboxylase (AADC) deficiency. This invention includes a method of treating AADC deficiency in a pediatric subject, comprising the steps of: (a) providing a pharmaceutical formulation comprising an rAAV2-hAADC vector, (b) stereotactically delivering the pharmaceutical formulation to at least one target site in the brain of the subject in a dose of an amount of at least about $1.8 \times 10^{11}$ vg; wherein delivering the pharmaceutical formulation to the brain is optionally by frameless stereotaxy, and optionally wherein the dose is an amount of at least about $2.4 \times 10^{11}$ vg and in some embodiments wherein the pharmaceutical formulation comprises a rAAV2-hAADC vector concentration of about $5.7 \times 10^{11}$ vg/mL. This invention is also directed to methods for treating aromatic L-amino acid decarboxylase (AADC) deficiency, wherein the method optionally further comprises the step of administering a therapeutically effective dose of dopamine-antagonist to the subject such as risperidone. This invention is also directed to methods for treating aromatic L-amino acid decarboxylase (AADC) deficiency, wherein the method optionally comprises providing a pharmaceutical formulation comprising an rAAV2-hAADC vector, and empty capsids.

15 Claims, 14 Drawing Sheets

Specification includes a Sequence Listing.

(56) References Cited

U.S. PATENT DOCUMENTS

| | | | |
|---|---|---|---|
| 7,402,564 | B1 | 7/2008 | Schteingart et al. |
| 7,427,396 | B2 | 9/2008 | Arbetman et al. |
| 7,534,613 | B2 | 5/2009 | Bankiewicz et al. |
| 7,588,757 | B2 | 9/2009 | Ozawa et al. |
| 8,137,948 | B2 | 3/2012 | Qu et al. |
| 8,309,355 | B2 | 11/2012 | Bankiewicz et al. |
| 8,709,811 | B2 | 4/2014 | Klee et al. |
| 8,865,881 | B2 | 10/2014 | Balazs et al. |
| 8,927,269 | B2 | 1/2015 | Bossis et al. |
| 9,284,357 | B2 | 3/2016 | Gao et al. |
| 9,492,415 | B2 | 11/2016 | Bankiewicz et al. |
| 9,527,904 | B2 | 12/2016 | Balazs et al. |
| 9,585,971 | B2 | 3/2017 | Deverman et al. |
| 9,598,703 | B2 | 3/2017 | Garcia et al. |
| 9,957,303 | B2 | 5/2018 | Deverman et al. |
| 10,006,049 | B2 | 6/2018 | Ling et al. |
| 10,035,825 | B2 | 7/2018 | Gao et al. |
| 10,072,251 | B2 | 9/2018 | Gao et al. |
| 10,202,425 | B2 | 2/2019 | Deverman et al. |
| 10,287,318 | B2 | 5/2019 | Korbelin et al. |
| 10,335,466 | B2 | 7/2019 | Kotin et al. |
| 10,400,252 | B2 | 9/2019 | Mitrophanous et al. |
| 2004/0058909 | A1 | 3/2004 | Goldstein |
| 2005/0143330 | A1 | 6/2005 | Mandel et al. |
| 2006/0193841 | A1 | 8/2006 | Mandel et al. |
| 2009/0036393 | A1 | 2/2009 | Kang |
| 2011/0269826 | A1 | 11/2011 | Kingsman et al. |
| 2012/0220648 | A1* | 8/2012 | Hwu ............... A61K 31/7088 514/44 R |
| 2012/0232133 | A1 | 9/2012 | Balazs et al. |
| 2014/0336245 | A1 | 11/2014 | Mingozzi et al. |
| 2015/0079038 | A1 | 3/2015 | Deverman et al. |
| 2016/0222067 | A1 | 8/2016 | Gao et al. |
| 2016/0256534 | A1 | 9/2016 | Bankiewicz et al. |
| 2016/0319303 | A1 | 11/2016 | Jimenez Cenzano et al. |
| 2017/0096683 | A1 | 4/2017 | Scaria et al. |
| 2017/0166925 | A1 | 6/2017 | Gao et al. |
| 2017/0166926 | A1 | 6/2017 | Deverman et al. |
| 2018/0066279 | A9 | 3/2018 | Gao et al. |
| 2018/0171357 | A1 | 6/2018 | Jantz et al. |
| 2018/0243249 | A1 | 8/2018 | Bankiewicz et al. |
| 2018/0362592 | A1 | 12/2018 | Gao et al. |
| 2019/0000940 | A1 | 1/2019 | Kotin et al. |
| 2019/0008931 | A1 | 1/2019 | Kotin et al. |
| 2019/0008932 | A1 | 1/2019 | Kotin et al. |
| 2019/0008933 | A1 | 1/2019 | Kotin et al. |
| 2019/0054158 | A1 | 2/2019 | Kotin et al. |
| 2019/0060425 | A1 | 2/2019 | Scheel et al. |
| 2019/0071681 | A1 | 3/2019 | Muzyczka et al. |
| 2019/0111157 | A1 | 4/2019 | Stanek et al. |
| 2019/0153034 | A1 | 5/2019 | Korbelin et al. |
| 2019/0153471 | A1 | 5/2019 | Paul et al. |
| 2019/0194689 | A1 | 6/2019 | Gao et al. |
| 2019/0224339 | A1 | 7/2019 | Paul et al. |
| 2019/0300904 | A1 | 10/2019 | Gao et al. |
| 2019/0343937 | A1 | 11/2019 | Scheel et al. |
| 2019/0358306 | A1 | 11/2019 | Kotin et al. |

FOREIGN PATENT DOCUMENTS

| | | |
|---|---|---|
| WO | 2019028306 | 2/2019 |
| WO | 2019210137 | 10/2019 |
| WO | 2019222328 | 11/2019 |
| WO | 2019222329 | 11/2019 |
| WO | 2019222441 | 11/2019 |
| WO | 2019222444 | 11/2019 |

OTHER PUBLICATIONS

Ayuso et al., "High MV vector purity results in serotype- and tissue-independent enhancement of transduction efficiency," Gene Therapy, 2010, pp. 503-510, vol. 17.

Barnett et al., "Frameless stereotaxy with scalp-applied fiducial markers for brain biopsy procedures: experience in 218 cases," Journal of Neurosurgery, 1999, pp. 569-576, vol. 91.

Barr et al.,. "Efficient catheter-mediated gene transfer into the hea11 using replication-defective adenovirus," Gene Therapy, 1994,. pp. 51-58, vol. 1.

Berkner, "Development of Adenovirus Vectors for the Expression of Heterologous Genes," BioTechniques, 1988, pp. 616-629, vol. 6, No. 7.

Berry et al., "Use of Cranial Fixation Pins in Pediatric Neurosurgery," Neurosurgery, 2008, pp. 913-919, vol. 62, No. 4.

Bett et al. "Packaging Capacity and Stability of Human Adenovirus Type 5 Vectors," Journal of Virology, 1993, pp. 5911-5921, vol. 67, No. 10.

Brun et al., "Clinical and biochemical features of aromatic L-amino acid decarboxylase deficiency," Neurology, 2010, pp. 64-71, vol. 75.

Chahal et al.. "Production of adeno-associated virus (AAV) serotypes by transient transfection of HEK293 cell suspension cultures for gene delivery," Journal of Virological Methods, 2014, pp. 163-173, vol. 196.

Chen et al., "Automatic fiducial localization in brain images," International Journal of Computer Assisted Radiology and Surgery, 2006, 5 pgs.

Christine et al., "Safety and tolerability of putaminal AADC gene therapy for Parkinson disease," Neurology, 2009, pp. 1662-1669, vol. 73.

Fan et al, "Behavioral Recovery in 6-Hydroxydopamine-Lesioned Rats by Cotransduction of Striatum with Tyrosine Hydroxylase and Aromatic L-Amino Acid Decarboxylase Genes Using Two Separate Adeno-Associated Virus Vectors," Human Gene Therapy, 1998, pp. 2527y2535, vol. 9.

Gao et al., "Empty virions in AAV8 vector prepartions reduce transduction efficiency and may cause total viral particle dose-limiting side effects," Molecular Therapy—Methods & Clinical Development, 2014, pp. 1-8, vol. 9.

Grimm et al., "Titration of MV-2 particles via a novel capsid ELISA: packaging of genomes can limit production of recombinant AAV-2," Gene Therapy, 1999, pp. 1322-1330, vol. 6, No. 7.

Gummert et al., •Newer Immunosuppressive Drugs: A Review, Journal ofthe American Society of Nephrology, 1999, pp. 1366-1380, vol. 10.

Haj-Ahmad et al!, "Development of a Helper-Independent Human Adenovirus Vector and Its Use in the Transfer of the Herpes Simplex Virus Thymidine Kinase Gene," Journal of Virology, 1986, pp. 267-274, vol. 57, No. 1.

Heermann et al., Navigation with the StealthStation(TM) in Skull Base Surgery: An Otolaryngological Perspective, Skull Base, 2001, pp. 277-285, vol. 11, No. 4.

Henderson et al. "The application accuracy of a skull-mounted trajectory guide system for image-guided functional neurosurgery," Computer Aided Surgery, 2004, pp. 155-160, vol. 9, No. 4.

Holloway el al., "Frameless stereotaxy using bone fiducial markers for deep brain stimulation," Journal of Neurosurgery. 2005, pp. 404-413, vol. 103.

Huang et al., "Advances in Immunotherapy for Glioblastoma Multiforme," Journal of Immunology Research, 2017, pp. 1-11, vol. 2017.

Hwu et al., Gene Therapy for Aromatic L-Amino Acid Decarboxylase Deficiency, Sci Transl Med, 2012, vol. 4, No. 134, pp. 1-8.

Hyland et al.,. "Aromatic Amino Acid Decarboxylase Deficiency in Twins." J. Inher. Metab, Dis., 1990, pp. 301-304, vol. 13.

International Search Report for Application No. PCT/US2018/027225, dated Dec. 6, 2018, 6 pages.

Kotin, "Prospects for the Use of Adeno-Associated Virus as a Vector for Human Gene Therapy," Human Gene Therapy, 1994, pp. 793-801, vol. 5.

Lock et al., "Analysis of Particle Content of Recombinant Adena-Associated Vims Serotype 8 Vectors by Ion-Exchange Chromatography," Human Gene Therapy Methods: Part B, 2012, pp. 56-64, vol. 23.

Maurer et al., "Registration of Head Volume Images Using Implantable Fiducial Markers," IEEE Transactions on Medical Imaging, 1997, pp. 447-462, vol. 16. No. 4.

(56) References Cited

OTHER PUBLICATIONS

Mehta et al., "Frameless stereotactic placement of depth electrodes in epilepsy surgery," J. Neurosurg., 2005, pp. 1040-1045, vol. 102.
Mingozzi et al., "Overcoming Preexisting Humoral Immunity to AAV Using Capsid Decoys," Sci Transl. Med., 2013, pp. 1-20, vol. 5, No. 194.
Mittereder et al., "Evaluation of the Efficacy and Safety of In Vitro, Adenovirus-Mediated Transfer of the Human Cystic Fibrosis Trnnsmembrane Conductance Regulator cDNA," Human Gene Therapy, 1994, pp. 717-729, vol. 5.
Muramatsu et al., "A Phase I Study of Aromatic I-Amino Acid Decarboxylase Gene Therapy for Parkinson's Disease", Molecular Therapy, 2010, vol. 18, No. 9, pp. 1731-1735.
Bankiewicz, K.S., et al., "Convection-Enhanced Delivery of AAV Vector in Parkinsonian Monkeys; In Vivo Detection of Gene Expression and Restoration of Dopaminergic Function Using Pro-drug Approach", Experimental Neurology, 2000, vol. 164, pp. 2-14.
Poli et al., "Epidural haematoma by Mayfield head-holder®: Case report and review of literature," Journal of Pediatric Sciences, 2013, e195, pp. 1-5, vol. 5.
Reszka et al., "Mechanism of Action of Bisphosphonates." Current Osteoporosis Reports, 2003, pp. 45-52, vol. 1.
Rich et al., "Development and Analysis of Recombinant Adenoviroses for Gene Therapy of Cystic Fibrosis," Human Gene Therapy, 1993, pp. 461-476, vol. 4.
Russell "Bisphosphonates: The first 40 years," Bone, 20-11, pp. 2-19, vol. 49.
Sebastian et al., Safety and tolerability of MRI-guided infusion of AAV2-hAADC into the mid-brain of nonhuman primate, Molecular Therapy—Methods & Clinical Development, 2014, vol. 3, 10 pages.
Seth et al., "Mechanism of Enhancement of DNA Expression Consequent to Cointernalization of a Replication-Deficient Adenovirus and Unmodified Plasmid DNA" Journal of Virology, 1994, pp. 933-940, vol. 68, No. 2.
Sommer et al,, "Quantification of Adena-Associated Virus Particles and Empty Capsids by Optical Density Measurement," Molecular Therapy, 2003, pp. 122-128, vol. 7, No. 1.
Stechison, "A Digitized Biopsy Needle for Frameless Stereotactic Biopsies with the StealthStation," Neurosurgery, 2000, pp. 239-242, vol. 46, No. 1.
Thompson el al., "Skull-fixated fiducial markers improve accuracy in staged frameless slereotactic epilepsy surgery in children," Journal of Neurosurgery: Pediatrics. 2011. pp. 116-119, vol. 7, No. 1.
Vega et al., "Image-Guided Deep Brain Stimulation," Neurosurgery Clinics of North America, 2014, pp. 159-172, vol. 25, No. 1.
Wang et al., "Automatic localization of the center of fiducial markers in 3D CT/MRI images for image-guided neurosurgery," Pattern Recognition Letters, 2009, pp. 414-420, vol. 30, No. 4.
Wassenberg et al., "Consensus guideline for the diagnosis and treatment of aromatic L-amino acid decarboxylase (AADC) deficiency," Orphanet Journal of Rare Diseases, 2017, pp. 1-21, vol. 12.
Wright. "AAV Empty Capsids: For Better or for Worse?", Molecular Therapy,. 2014,. pp. 1-2, vol. 22. No. 1.
Written Opinion for Application No. PCT/US2018/027225, dated Dec. 6, 2018, 7 pages.
Wurm et al., "Novalis Frameless Image-Guided Noninvasive Radiosurgery: Initial Experience," Neurosurgery, 2008, pp. A11-A18, vol. 62, No. 5.
Samaranch et al., "Slow AAV2 clearance from the brain of nonhuman primates and anti-capsid immune response", Gene Therapy, 2016, pp. 393-398, vol. 23, No. 4.
Appeal from the United States Patent and Trademark Office, Patent Trial and Appeal Board in No. U.S. Appl. No. 12/456,567, In Re: Stephan Company, decided Aug. 25, 2017, No. 2016-1811, 11 pages.
McInerney et al., "Frameless stereotaxy of the brain", The Mount Sinai Journal of Medicine, 2000, pp. 300-310, vol. 67, No. 4.
First Office Action in Mexican Patent Appln. No. MX/A/2019/012113, dated May 31, 2023, dated May 23, 2023, 14 pages.

* cited by examiner

Biological Substance (rAAV2-hAADC Vector) Diagram

| | |
|---|---|
| ITR | = AAV2 inverted terminal repeat |
| CMV IEP | = Human cytomegalovirus immediate-early promoter |
| HBG2/3 | = Human beta globin partial intron 2/partial exon 3 |
| hAADC | = Human dopa decarboxylase (*DDC*) cDNA |
| Poly A | = Polyadenylation containing sequence |

Surgical Equipment

Figure 3
Surgical Equipment

Swaged catheter (brain and product contacting) (increased magnification)

Brain End of Swaged Cannula (Not to scale)

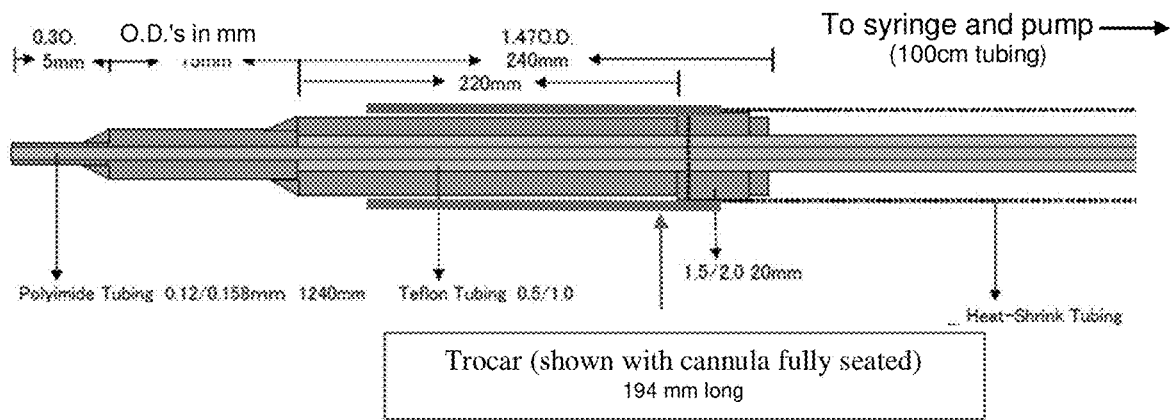

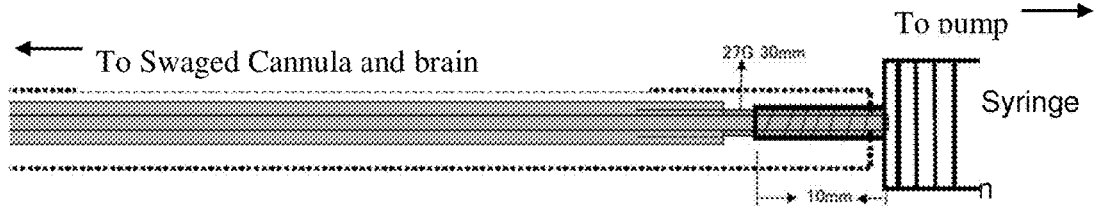

Swaged Cannula (Eicom Corporation) Components
Stainless Steel (product and brain tissue contact)
Polyimide Tubing (delivers vector solution)
Medical Adhesive (no product or brain tissue contact)
Teflon and "Heat-Shrink" Tubing (no product or brain tissue contact)

Bilateral Injection into the Putamen

PDMS-2 Total Raw Scores by Subject and Chronological Age (n=18)

LS means and SE for PDMS total score over time through 12 months after vector administration (n=18).

AIMS Total Scores by Subject and Chronological Age (n=18).

LS means and SE for AIMS total score over time through 12 months after vector administration (n=18).

Images of $^{18}$F-DOPA PET before and after gene therapy treatment.

LS mean PET specific uptake over time through 12 months after gene therapy treatment.

Schematic Overview of an rAAV-hAADC Vector Manufacture pAAV-CMV-hAADC-KanR DNA Map

Figure 13:

Nucleotide sequence of a pAAV-CMV-hAADC-KanR plasmid (SEQ ID NO. 1)

```
TGACAGATCT GCGCGCGATC GATCTGCGCG CTCGCTCGCT CACTGAGGCC GCCCGGGCGT CGGGCGACCT TTGGTCGCCC GGCCTCAGTG AGCGAGCGAG
CGCGCAGAGA GGGAGTGGCC AACTCCATCA CTAGGGGTTC CTTGTAGTTA ATGATTAACC CGCCATGCTA CTTATCTACG TAGCCATGCT CTAGAGCGGC
CGCACGCGTA CTAGTTATTA ATAGTAATCA ATTACGGGGT CATTAGTTCA TAGCCCATAT ATGGAGTTCC GCGTTACATA ACTTACGGTA AATGGCCCGC
CTGGCTGACC GCCCAACGAC CCCCGCCCAT TGACGTCAAT AATGACGTAT GTTCCCATAG TAACGCCAAT AGGGACTTTC CATTGACGTC AATGGGTGGA
GTATTTACGG TAAACTGCCC ACTTGGCAGT ACATCAAGTG TATCATATGC CAAGTACGCC CCCTATTGAC GTCAATGACG GTAAATGGCC CGCCTGGCAT
TATGCCCAGT ACATGACCTT ATGGGACTTT CCTACTTGGC AGTACATCTA CGTATTAGTC ATCGCTATTA CCATGGTGAT GCGGTTTTGG CAGTACATCA
ATGGGCGTGG ATAGCGGTTT GACTCACGGG GATTTCCAAG TCTCCACCCC ATTGACGTCA ATGGGAGTTT GTTTTGGCAC CAAAATCAAC GGGACTTTCC
AAAATGTCGT AACAACTCCG CCCCATTGAC GCAAATGGGC GGTAGGCGTG TACGGTGGGA GGTCTATATA AGCAGAGCTC GTTTAGTGAA CCGTCAGATC
GCCTGGAGAC GCCATCCACG CTGTTTTGAC CTCCATAGAA GACACCGGGA CCGATCCAGC CTCCGCGGAT TCGAATCCCG GCCGGGAACG GTGCATTGGA
ACGCGGATTC CCCGTGCCAA GAGTGACGTA AGTACCGCCT ATAGAGTCTA TAGGCCCACA AAAAATGCTT TCTTCTTTTA ATATACTTTT TTGTTTATCT
TATTTCTAAT ACTTTCCCTA ATCTCTTTCT TTCAGGGCAA TAATGATACA ATGTATCATG CCTCTTTGCA CCATTCTAAA GAATAACAGT GATAATTTCT
GGGTTAAGGC AATAGCAATA TTTCTGCATA TAAATATTTC TGCATATAAA TTGTAACTGA TGTAAGAGGT TTCATATTGC TAATAGCAGC TACAATCCAG
CTACCATTCT GGTTTATTTT TATGGTTGGG ATAAGGCTGG ATTATTCTGA GTCCAAGCTA GGCCCTTTTG CTAATCATGT TCATACCTCT TATCTTCCTC
CCACAGCTCC TGGGCAACGT GCTGGTCTGT GTGCTGGCCC ATCACTTTGG CAAAGAATTG GGATTCGAAC ATCGATTGAA TTCCCCGGGG ATCCACCATG
AACGCAAGTG AATCCGAAG GAGAGGGAAG GAGATGGTTG ATTACTGAGC CAACTACATG AGGCCATTG AGGGACCGCA GGTCTACCCT GACGTGGAGC
CCGGGTACCT GCGGCCGCTG ATCCCTGCCG CTGCCCCTCA GGAGCCAGAC ACGTTTGAGG ACATCATCAA CGACGTTGAG AAGATAATCA TGCCTGGGGT
GACGCACTGG CACAGCCCCT ACTTCTTCGC CTACTTCCCC ACTGCCAGCT CGTACCCGGC CATGCTTGCG GACATGCTGT GCGGGGCCAT TGGCTGCATC
GGCTTCTCCT GGGCGGCAAG CCCAGCATGC ACAGAGCTGG AGACTGTGAT GATGGACTGG CTCGGGAAGA TGCTGGAACT ACCAAAGGCA TTTTTGAATG
AGAAAGCTGG AGAAGGGGGA GGAGTGATCC AGGGAAGTGC CAGTGAAGCC ACCCTGGTGG CCCTGCTGGC CGCTCGGGAC AAAGTGATCC ATCGGCTGCA
GGCAGCGTCC CCAGAGCTCA CACAGGCCGC TATCATGGAG AAGCTGGTGG CTTACTCATC CGATCAGGCA CACTCCTCAG TGGAAAGAGC TGGGTTAATT
GGTGGAGTGA AATTAAAAGC CATCCCCTCA GATGGCAACT TCGCCATGCG TGCGTCTGCC CTGCAGGAAG CCCTGGAGAG AGACAAAGCG GCTGGCCTGA
TTCCTTTCTT TATGGTTGCC ACCCTGGGGA CCACAACATG CTGCTCCTTC GACAAATCTC TAGAAGTCGG TCCTATCTGC AACAAGGAAG ACATATGGCT
GCACGTTGAT GCAGCCTACG CAGGCAGTGC ATTCATCTGC CCTGAGTTCC GGCACCTTCT GAATGAGTG GAGTTTGCAG ATTCATTCAA CTTTAATCCC
CACAAATGGC TATTGGTGAA TTTTGACTGT TCTGCCATGT GGGTGAAAAA GAGAACAGAC TTAACGGGAG CCTTTAGACT GGACCCCACT TACCTGAAGC
ACAGCCATCA GGATTCAGGG CTTATCACTG ACTACCGGCA TTGGCAGATA CCACTGGGCA GAAGATTTCG CTCTTTGAAA ATGTGGTTTG TATTTAGGAT
GTATGGAGTC AAAGGACTGC AGGCTTATAT CCGCAAGCAT GTCCAGCTGT CCCATGAGTT TGAGTCACTG GTGCGCCAGG ATCCCCGCTT TGAAATCTGT
GTGGAAGTCA TTCTGGGGCT TGTCTGCTTT CGGCTCAAGG GTTCCAACAA AGTGAATGAA GCTCTTCTGC AAAGAATAAA CAGTGCCAAA AAAATCCACT
TGGTTCCATG TCACCTCAGG GACAAGTTTG TCCTGCGCTT TGCCATCTGT TCTCGCACGG TGGAATCTGC CCATGTGCAG CGGGCCTGGG AACACATCAA
AGAGCTGGCG GCCGACGTGC TGCGAGCAGA GAGGGAGTAG GAGTGAAGCC AGCTGCGGGA GCCAAGAATT GAAGAGAGAT ATATCTGAAA ACTGGAATAA
GAAGCAAATA AATATCATCC TGCCTTCATG GAACTCAGCT GTCTGTGGCT TCCCATGTCT TTCTCCAAAG TTATCCAGAG GGTTGTGATT TTGTCTGCTT
AGTATCTCAT CAACAAAGAA ATATTATTTG CTAATTAAAA AGTTAATCTT CATGGCCATA GCTTTTATTC ATTAGCTGTG ATTTTGTTG ATTAAAACAT
TATAGATTTT CATGTTCTTG CAGTCATCAG AAGTGGTAGG AAAGCCTCAC TGATATATTT TCCAGGGCAA TCAATGTTCA CGCAACTTGA AATTATATCT
GTGGTCTTCA AATTGTCTTT TGTCATGTGG CTAAATGCCT AATAAGGAAT TAATTCGATA TCAACACACG GTAGGGATAA CAGGGTAATC
TCGAGGCAAG CTTGGGCCCG GTACCCAATT CGCCCTATAG TGAGTCGTAT TACGCGCGCA GCGGCCGACC ATGGCCCAAC TTGTTATTG CAGCTTATAA
TGGTTACAAA TAAAGCAATA GCATCACAAA TTTCACAAAT AAAGCATTTT TTTCACTGCA TTCTAGTTGT GGTTTGTCCA AACTCATCAA TGTATCTTAT
CATGTCTGGA TCTCCGGACA CGTGCGGACC GAGCGGCCGC TCTAGAGCAT GGCTACGTAG ATAAGTAGCA TGGCGGGTTA ATCATTAACT ACAAGGAACC
CCTAGTGATG GAGTTGGCCA CTCCCTCTCT GCGCGCTCGC TCGCTCACTG AGGCCGGGCG ACCAAAGGTC GCCCGACGCC CGGGCTTTGC CCGGGCGGCC
TCAGTGAGCG AGCGAGCGCG CAGATCAGCG CTTTAAATTC AGAAGAACTC GTCAAGAAGG CGATAGAAGG CGATGCGCTG CGAATCGGGA GCGGCGATAC
CGTAAAGCAC GAGGAAGCGG TCAGCCCATT CGCCGCCAAG CTCTTCAGCA ATATCACGGG TAGCCAACGC TATGTCCTGA TAGCGGTCCG CCACACCCAG
CCGGCCACAG TCGATGAATC CAGAAAAGCG GCCATTTTCC ACCATGATAT TCGGCAAGCA GGCATCGCCA TGGGTCACGA CGAGATCCTC GCCGTCGGGC
ATGCTCGCCT TGAGCCTGGC GAACAGTTCG GCTGGCGCGA GCCCCTGATG CTCTTCGTCC AGATCATCCT GATCGACAAG ACCGGCTTCC ATCCGAGTAC
GTGCTCGCTC GATGCGATGT TTCGCTTGGT GGTCGAATGG GCAGGTAGCC GGATCAAGCG TATGCAGCCG CCGCATTGCA TCAGCCATGA TGGATACTTT
CTCGGCAGGA GCAAGGTGAG ATGACAGGAG ATCCTGCCCC GGCACTTCGC CCAATAGCAG CCAGTCCCTT CCCGCTTCAG TGACAACGTC GAGCACAGCT
GCGCAAGGAA CGCCCGTCGT GGCCAGCCAC GATAGCCGCG CTGCCTCGTC TTGCAGTTCA TTCAGGGCAC CGGACAGGTC GGTCTTGACA AAAAGAACCG
GGCGCCCCTG CGCTGACAGC CGGAACACGG CGGCATCAGA GCAGCCGATT GTCTGTTGTG CCCAGTCATA GCCGAATAGC CTCTCCACCC AAGCGGCCGG
AGAACCTGCG TGCAATCCAT CTTGTTCAAT CATGCGAAAC GATCCTCATC CTGTCTCTTG ATCAGATCTT GATCCCCTGC GCCATCAGAT CTTTGGCGGC
AAGAAAGCCA TCCAGTTTAC TTTGCAGGGC TTCCCAACCT TACCAGAGGG CGCCCCAGCT GGCAATTCCG GTTCGCTTGC TGTCCATAAA ACCGCCCAGT
CTAGCTATCG CCATGTAAGC CCACTGCAAG CTACCTGCTT TCTCTTTGCG CTTGCGTTTT CCCTTGTCCA GATAGCCCAG TAGCTGACAT TCATCCGGGG
TCAGCACCGT TTCTGCGGAC TGGCTTTCTA CGTGAAAAGG ATCTAGGTGA AGATCCTTTT TGATAATCTC ATGACCAAAA TCCCTTAACG TGAGTTTTCG
TTCCACTGAG CGTCAGACCC CGTAGAAAAG ATCAAAGGAT CTTCTTGAGA TCCTTTTTTT CTGCGCGTAA TCTGCTGCTT GCAAACAAAA AAACCACCGC
TACCAGCGGT GGTTTGTTTG CCGGATCAAG AGCTACCAAC TCTTTTTCCG AAGGTAACTG GCTTCAGCAG AGCGCAGATA CCAAATACTG TTCTTCTAGT
GTAGCCGTAG TTAGGCCACC ACTTCAAGAA CTCTGTAGCA CCGCCTACAT ACCTCGCTCT GCTAATCCTG TTACCAGTGG CTGCTGCCAG TGGCGATAAG
TCGTGTCTTA CCGGGTTGGA CTCAAGACGA TAGTTACCGG ATAAGGCGCA GCGGTCGGGC TGAACGGGGG GTTCGTGCAC ACAGCCCAGC TTGGAGCGAA
CGACCTACAC CGAACTGAGA TACCTACAGC GTGAGCTATG AGAAAGCGCC ACGCTTCCCG AAGGGAGAAA GGCGGACAGG TATCCGGTAA GCGGCAGGGT
CGGAACAGGA GAGCGCACGA GGGAGCTTCC AGGGGGAAAC GCCTGGTATC TTTATAGTCC TGTCGGGTTT CGCCACCTCT GACTTGAGCG TCGATTTTTG
TGATGCTCGT CAGGGGGGCG GAGCCTATGG AAAAACGCCA GCAACGCGGC CTTTTTACGG TTCCTGGCCT TTTGCTGGCC TTTTGCTCAC A
```

Figure 14:

Nucleotide sequence of a rAAV-hAADC-gene insert (SEQ ID NO. 2)

```
TCTGCGCG CTCGCTCGCT CACTGAGGCC GCCCGGGCGT CGGGCGACCT TTGGTCGCCC GGCCTCAGTG
AGCGAGCGAG CGCGCAGAGA GGGAGTGGCC AACTCCATCA CTAGGGGTTC CTTGTAGTTA ATGATTAACC
CGCCATGCTA CTTATCTACG TAGCCATGCT CTAGAGCGGC CGCACGCGTA CTAGTTATTA ATAGTAATCA
ATTACGGGGT CATTAGTTCA TAGCCCATAT ATGGAGTTCC GCGTTACATA ACTTACGGTA AATGGCCCGC
CTGGCTGACC GCCCAACGAC CCCCGCCCAT TGACGTCAAT AATGACGTAT GTTCCCATAG TAACGCCAAT
AGGGACTTTC CATTGACGTC AATGGGTGGA GTATTTACGG TAAACTGCCC ACTTGGCAGT ACATCAAGTG
TATCATATGC CAAGTACGCC CCCTATTGAC GTCAATGACG GTAAATGGCC CGCCTGGCAT TATGCCCAGT
ACATGACCTT ATGGGACTTT CCTACTTGGC AGTACATCTA CGTATTAGTC ATCGCTATTA CCATGGTGAT
GCGGTTTTGG CAGTACATCA ATGGGCGTGG ATAGCGGTTT GACTCACGGG GATTTCCAAG TCTCCACCCC
ATTGACGTCA ATGGGAGTTT GTTTTGGCAC CAAAATCAAC GGGACTTTCC AAAATGTCGT AACAACTCCG
CCCCATTGAC GCAAATGGGC GGTAGGCGTG TACGGTGGGA GGTCTATATA AGCAGAGCTC GTTTAGTGAA
CCGTCAGATC GCCTGGAGAC GCCATCCACG CTGTTTTGAC CTCCATAGAA GACACCGGGA CCGATCCAGC
CTCCGCGGAT TCGAATCCCG GCCGGGAACG GTGCATTGGA ACGCGGATTC CCCGTGCCAA GAGTGACGTA
AGTACCGCCT ATAGAGTCTA TAGGCCCACA AAAAATGCTT TCTTCTTTTA ATATACTTTT TTGTTTATCT
TATTTCTAAT ACTTTCCCTA ATCTCTTTCT TTCAGGGCAA TAATGATACA ATGTATCATG CCTCTTTGCA
CCATTCTAAA GAATAACAGT GATAATTTCT GGGTTAAGGC AATAGCAATA TTTCTGCATA TAAATATTTC
TGCATATAAA TTGTAACTGA TGTAAGAGGT TTCATATTGC TAATAGCAGC TACAATCCAG CTACCATTCT
GGTTTTATTT TATGGTTGGG ATAAGGCTGG ATTATTCTGA GTCCAAGCTA GGCCCTTTTG CTAATCATGT
TCATACCTCT TATCTTCCTC CCACAGCTCC TGGGCAACGT GCTGGTCTGT GTGCTGGCCC ATCACTTTGG
CAAAGAATTG GGATTCGAAC ATCGATTGAA TTCCCCGGGG ATCCACCATG AACGCAAGTG AATTCCGAAG
GAGAGGGAAG GAGATGGTGG ATTACGTGGC CAACTACATG GAAGGCATTG AGGGACGCCA GGTCTACCCT
GACGTGGAGC CCGGGTACCT GCGGCCGCTG ATCCCTGCCG CTGCCCCTCA GGAGCCAGAC ACGTTGAGG
ACATCATCAA CGACGTTGAG AAGATAATCA TGCCTGGGGT GACGCACTGG CACAGCCCCT ACTTCTTCGC
CTACTTCCCC ACTGCCAGCT CGTACCCGGC CATGCTTGCG GACATGCTGT GCGGGGCCAT TGGCTGCATC
GGCTTCTCCT GGGCGGCAAG CCCAGCATGC ACAGAGCTGG AGACTGTGAT GATGGACTGG CTCGGGAAGA
TGCTGGAACT ACCAAAGGCA TTTTTGAATG AGAAAGCTGG AGAAGGGGGA GGAGTGATCC AGGGAAGTGC
CAGTGAAGCC ACCCTGGTGG CCCTGCTGGC CGCTCGGACC AAAGTGATCC ATCGGCTGCA GGCAGCGTCC
CCAGAGCTCA CACAGGCCGC TATCATGGAG AAGCTGGTGG CTTACTCATC CGATCAGGCA CACTCCTCAG
TGGAAAGAGC TGGGTTAATT GGTGGAGTGA AATTAAAAGC CATCCCCTCA GATGGCAACT TCGCCATGCG
TGCGTCTGCC CTGCAGGAAG CCCTGGAGAG AGACAAAGCG GCTGGCCTGA TTCCTTTCTT TATGGTTGCC
ACCCTGGGGA CCACAACATG CTGCTCCTTT GACAATCTCT TAGAAGTCGG TCCTATCTGC AACAAGGAAG
ACATATGGCT GCACGTTGAT GCAGCCTACG CAGGCAGTGC ATTCATCTGC CCTGAGTTCC GGCACCTTCT
GAATGGAGTG GAGTTTGCAG ATTCATTCAA CTTTAATCCC CACAAATGGC TATTGGTGAA TTTTGACTGT
TCTGCCATGT GGGTGAAAAA GAGAACAGAC TTAACGGGAG CCTTTAGACT GGACCCCACT TACCTGAAGC
ACAGCCATCA GGATTCAGGG CTTATCACTG ACTACCGGCA TTGGCAGATA CCACTGGGCA GAAGATTTCG
CTCTTTGAAA ATGTGGTTTG TATTTAGGAT GTATGGAGTC AAAGGACTGC AGGCTTATAT CCGCAAGCAT
GTCCAGCTGT CCCATGAGTT TGAGTCACTG GTGCGCCAGG ATCCCCGCTT TGAAATCTGT GTGGAAGTCA
TTCTGGGGCT TGTCTGCTTT CGGCTAAAGG GTTCCAACAA AGTGAATGAA GCTCTTCTGC AAAGAATAAA
CAGTGCCAAA AAAATCCACT TGGTTCCATG TCACCTCAGG GACAAGTTTG TCCTGCGCTT TGCCATCTGT
TCTCGCACGG TGGAATCTGC CCATGTGCAG CGGGCCTGGG AACACATCAA AGAGCTGGCG GCCGACGTGC
TGCGAGCAGA GAGGGAGTAG GAGTGAAGCC AGCTGCAGGA ATCAAAAATT GAAGAGAGAT ATATCTGAAA
ACTGGAATAA GAAGCAAATA AATATCATCC TGCCTTCATG GAACTCAGCT GTCTGTGGCT TCCCATGTCT
TTCTCCAAAG TTATCCAGAG GGTTGTGATT TTGTCTGCTT AGTATCTCAT CAACAAAGAA ATATTATTTG
CTAATTAAAA AGTTAATCTT CATGGCCATA GCTTTTATTC ATTAGCTGTG ATTTTGTTG ATTAAACAT
TATAGATTTT CATGTTCTTG CAGTCATCAG AAGTGGTAGG AAAGCCTCAC TGATATATTT TCCAGGGCAA
TCAATGTTCA CGCAACTTGA AATTATATCT GTGGTCTTCA AATTGTCTTT TGTCATGTGG CTAAATGCCT
AATAAGGAAT TAATTCGATA TCAAGCTATC CAACACACTG GTAGGGATAA CAGGGTAATC TCGAGGCAAG
CTTGGGCCCG GTACCCAATT CGCCCTATAG TGAGTCGTAT TACGCGCGCA GCGGCCGACC ATGGCCCAAC
TTGTTTATTG CAGCTTATAA TGGTTACAAA TAAAGCAATA GCATCACAAA TTTCACAAAT AAAGCATTT
TTTCACTGCA TTCTAGTTGT GGTTTGTCCA AACTCATCAA TGTATCTTAT CATGTCTGGA TCTCCGGACA
CGTGCGGACC GAGCGGCCGC TCTAGAGCAT GGCTACGTAG ATAAGTAGCA TGGCGGGTTA ATCATTAACT
ACAAGGAACC CCTAGTGATG GAGTTGGCCA CTCCCTCTCT GCGCGCTCGC TCGCTCACTG AGGCCGGGCG
ACCAAAGGTC GCCCGACGCC CGGGCTTTGC CCGGCGGCC TCAGTGAGCG AGCGAGCGCG CAGAT
```

GENE THERAPY FOR AADC DEFICIENCY

CROSS-REFERENCE TO RELATED APPLICATIONS

This application is a continuation of U.S. patent application Ser. No. 15/951,270, filed Apr. 12, 2018, now U.S. Pat. No. 10,898,585, which claims the benefit of and priority to U.S. Provisional Application Ser. No. 62/485,658, filed Apr. 14, 2017, the entire contents of which are hereby incorporated by reference in their entirety.

FIELD OF THE INVENTION

This invention concerns a method of treating AADC deficiency in a subject, comprising the steps of (a) providing a pharmaceutical formulation comprising an rAAV2-hAADC vector and (b) delivering the pharmaceutical formulation to the brain of the subject; in an amount of at least about $1.8 \times 10^{11}$ vg. Particular reference is made to treating pediatric subjects using frameless stereotaxy, treating dyskinesia in pediatric subjects. Particular reference is also made to pharmaceutical formulations comprising rAAV2-hAADC vectors and empty capsids.

REFERENCE TO SEQUENCE LISTING

This application contains a Sequence Listing that has been submitted in ASCII format via EFS-Web and is hereby incorporated by reference in its entirety. The ASCII copy, created on Sep. 6, 2018, is named A36-7000US1_085143-593590_SL.txt, and is 13,000 bytes in size. A paper copy of the sequence listing and a computer readable form of the same sequence listing are appended below and herein incorporated by reference. The information recorded in computer readable form is identical to the written sequence listing, according to 37 C.F.R. 1.821(f).

BACKGROUND

Aromatic L-amino acid decarboxylase (AADC) deficiency is a rare genetic disorder believed to arise from mutation of the DDC gene (dopa decarboxylase). Without being bound by any theory, AADC is an enzyme reported in the literature as responsible for the final step in the synthesis of neurotransmitters dopamine (which is then synthesized into norepinephrine and subsequently epinephrine) and serotonin (which is then synthesized into melatonin). AADC deficiency results in severe developmental failures, global muscular hypotonia and dystonia, severe, long-lasting seizures known as oculo-gyric crises, frequent hospitalizations (including prolonged stays in intensive care), and the need for life-long care. Symptoms and severity vary depending on the type of underlying genetic mutation which abrogates AADC enzyme function.

Presently, treatment options are limited. Only patients with relatively mild forms of the disease respond to drugs. Furthermore, patients obtain relief from only a limited subset of symptoms. Drug therapy provides little or no benefit for many patients who often die during childhood. Patients with severe forms usually die before the age of 6 or 7 years due to severe motor dysfunction, autonomic abnormalities, and secondary complications such as choking, hypoxia, and pneumonia.

Only limited research has been directed toward AADC deficiency in children. Only one group has reported the restoration of some motor development and function in four children treated for AADC deficiency by gene therapy using a low dosage. No dose has been used above $1.6 \times 10^{11}$ vg per subject. See Wuh-Liang Hwu, et al., "Gene Therapy for Aromatic 1-Amino Acid Decarboxylase Deficiency," *Sci. Transl. Med.* 4, 134 (2012), and Wuh Liang Hwu, et al., U.S. Pat. App. Pub. No. US 2012/0220648. These references and all publications cited herein are incorporated by reference in their entirety.

Other research has been limited to adult patients with Parkinson's disease. Clinical studies using gene therapy in Parkinson's disease have shown that the adeno-associated virus (AAV) type 2 vector-mediated delivery of the human AADC gene (hAADC) into the putamen is safe and well tolerated in adults. See C. W. Christine, et al., "Safety and tolerability of putaminal AADC gene therapy for Parkinson disease," *Neurology* 73, 1662-1669 (2009); and S. Muramatsu, et al., "A phase I study of aromatic L-amino acid decarboxylase gene therapy for Parkinson's disease," *Mol. Ther.* 18, 1731-1735 (2010); K. Ozawa et al. U.S. Pat. No. 7,588,757 "Methods of treating Parkinson's disease using recombinant adeno-associated virus virions"; and K. Bankiewicz et al., U.S. Pat. No. 6,309,634, "Methods of treating Parkinson's disease using recombinant adeno-associated vector (rAAV)."

Several problems of AADC gene therapy treatments need to be addressed. (i) There is no data as to the safety or efficacy of high doses in children. (ii) There is no data as to the safety or efficacy of doses selected according to a child's age. (iii) Stereotaxy for AADC gene therapy in Parkinson's disease uses a cumbersome skull-fixed head frame that is not feasible for pediatric subjects. (iv) There is no data as to the safety or efficacy of treatments for pediatric subjects experiencing AADC gene therapy induced dyskinesia. (v) A subject's immune system limits AADC gene transduction. Without being bound by theory, it is believed that macrophages neutralize adeno-associated virus (AAV)-mediated gene delivery by phagocytosis of AAV particles.

SUMMARY OF THE INVENTION

The present invention is directed to compositions and methods for treating aromatic L-amino acid decarboxylase (AADC) deficiency.

FOR SUMMERY OF INVENTION

This invention includes a method of treating AADC deficiency in a pediatric subject, comprising the steps of: (a) providing a pharmaceutical formulation comprising an rAAV2-hAADC vector, (b) stereotactically delivering the pharmaceutical formulation to at least one target site in the brain of the subject in a dose of an amount at least about $1.8 \times 10^{11}$ vg; wherein delivering the pharmaceutical formulation to the brain is by frameless stereotaxy, and optionally wherein the dose is an amount of at least about $2.4 \times 10^{11}$ vg and in some embodiments wherein the pharmaceutical formulation comprises a rAAV2-hAADC vector concentration of about $5.7 \times 10^{11}$ vg/mL. Particular note is made that the pharmaceutical formulation is delivered at a rate of about 3 µL/min and further wherein the pharmaceutical formulation is delivered to at least one target site in a brain at a dose volume of about 80 µL per target site.

Particular note is also made that the pharmaceutical formulation is delivered to a putamen of the brain. In one embodiment, the pharmaceutical formulation is delivered bilaterally to each putamen. In one particular embodiment, said bilateral delivery is to points about 1 mm to about 10 mm apart. Optionally the rAAV2-hAADC vector comprises: (a) a WT AAV2 capsid, and (b) a recombinant DNA DDC gene insert comprising: (i) a first inverted terminal repeat (ITR), (ii) a cytomegalovirus (CMV) immediate early promoter (IEP)IEP, (iii) a human β-globin partial intron2/exon 3, (iv) a nucleic acid sequence encoding hAADC, (v) an SV40 poly A tail, and (vi) a second ITR; wherein the first ITR and second ITR flank the CMV IEP promoter and the Poly A tail. Particular note is made that the nucleic acid sequence encoding hAADC is an unmodified DDC cDNA. In further embodiments, the method further comprises the step of: (c) administering a therapeutically effective dose of dopamine-antagonist to the subject. Particular note is made that the dopamine-antagonist can be optionally clozapine, haloperidol, olanzapine paliperidone, quetiapine, risperidone, or ziprasidone, optionally administered at a dose from about 0.1 mg daily to about 1000 mg daily.

This invention also includes a method of treating gAADC deficiency in a pediatric subject, comprising the steps of: (a) providing a pharmaceutical formulation comprising an rAAV2-hAADC vector, and (b) stereotactically delivering the pharmaceutical formulation to at least one target site in the brain of the subject in a dose of an amount at least about $2.4 \times 10^{11}$ vg. In some embodiments wherein the pharmaceutical formulation comprises a rAAV2-hAADC vector concentration of about $7.5 \times 10^{11}$ vg/mL. Particular note is made that the pharmaceutical formulation is delivered at a rate of about 3 µL/min and further wherein the pharmaceutical formulation is delivered to at least one target site in a brain at a dose volume of about 80 µL per target site. Particular note is also made that the pharmaceutical formulation is delivered to a putamen of the brain. In one embodiment, the pharmaceutical formulation is delivered bilaterally to each putamen. In one particular embodiment, said bilateral delivery is to points about 1 mm to about 10 mm apart. Optionally the rAAV2-hAADC vector comprises: (a) a WT AAV2 capsid, and (b) a recombinant DNA DDC gene insert comprising: (i) a first inverted terminal repeat (ITR), (ii) a cytomegalovirus (CMV) immediate early promoter (IEP) IEP, (iii) a human β-globin partial intron2/exon 3, (iv) a nucleic acid sequence encoding hAADC, (v) an SV40 poly A tail, and (vi) a second ITR; wherein the first ITR and second ITR flank the CMV IEP promoter and the Poly A tail. Particular note is made that the nucleic acid sequence encoding hAADC is an unmodified DDC cDNA. In further embodiments, the method further comprises the step of: (c) administering a therapeutically effective dose of dopamine-antagonist to the subject. Particular note is made that the dopamine-antagonist can be optionally clozapine, haloperidol, olanzapine, paliperidone, quetiapine, risperidone, or ziprasidone, optionally administered at a dose from about 0.1 mg daily to about 1000 mg daily.

This invention also includes a method of treating AADC deficiency in a pediatric subject aged less than about 3 years, comprising the steps of: (a) providing a pharmaceutical formulation comprising an rAAV2-hAADC vector, and (b) stereotactically delivering the pharmaceutical formulation to at least one target site in the brain of the subject in a dose of an amount at least about $2.0 \times 10^{11}$ vg; and optionally wherein the dose is an amount of at least about $2.4 \times 10^{11}$ vg and in some embodiments wherein the pharmaceutical formulation comprises a rAAV2-hAADC vector concentration of about $7.5 \times 10^{11}$ vg/mL. Particular note is made that the pharmaceutical formulation is delivered at a rate of about 3 µL/min and further wherein the pharmaceutical formulation is delivered to at least one target site in a brain at a dose volume of about 80 µL per target site. Particular note is also made that the pharmaceutical formulation is delivered to a putamen of the brain. In one embodiment, the pharmaceutical formulation is delivered bilaterally to each putamen. In one particular embodiment, said bilateral delivery is to points about 1 mm to about 10 mm apart. Optionally the rAAV2-hAADC vector comprises: (a) a WT AAV2 capsid, and (b) a recombinant DNA DDC gene insert comprising: (i) a first inverted terminal repeat (ITR), (ii) a cytomegalovirus (CMV) immediate early promoter (IEP)IEP, (iii) a human β-globin partial intron2/exon 3, (iv) a nucleic acid sequence encoding hAADC, (v) an SV40 poly A tail, and (vi) a second ITR; wherein the first ITR and second ITR flank the CMV IEP promoter and the Poly A tail. Particular note is made that the nucleic acid sequence encoding hAADC is an unmodified DDC cDNA. In further embodiments, the method further comprises the step of: (c) administering a therapeutically effective dose of dopamine-antagonist to the subject. Particular note is made that the dopamine-antagonist can be optionally clozapine, haloperidol, olanzapine, paliperidone, quetiapine, risperidone, or ziprasidone, optionally administered at a dose from about 0.1 mg daily to about 1000 mg daily.

This invention also includes a method of treating AADC deficiency in a pediatric subject aged about 3 or more years, comprising the steps of: (a) providing a pharmaceutical formulation comprising an rAAV2-hAADC vector, and (b) stereotactically delivering the pharmaceutical formulation to at least one target site in the brain of the subject in a dose from about $1.8 \times 10^{11}$ vg to about $2.4 \times 10^{11}$ vg. Particular note is made that the pharmaceutical formulation is delivered at a rate of about 3 µL/min and further wherein the pharmaceutical formulation is delivered to at least one target site in a brain at a dose volume of about 80 µL per target site. Particular note is also made that the pharmaceutical formulation is delivered to a putamen of the brain. In one embodiment, the pharmaceutical formulation is delivered bilaterally to each putamen. In one particular embodiment, said bilateral delivery is to points about 1 mm to about 10 mm apart. Optionally the rAAV2-hAADC vector comprises: (a) a WT AAV2 capsid, and (b) a recombinant DNA DDC gene insert comprising: (i) a first inverted terminal repeat (ITR), (ii) a cytomegalovirus (CMV) immediate early promoter (IEP) IEP, (iii) a human β-globin partial intron2/exon 3, (iv) a nucleic acid sequence encoding hAADC, (v) an SV40 poly A tail, and (vi) a second ITR; wherein the first ITR and second ITR flank the CMV IEP promoter and the Poly A tail. Particular note is made that the nucleic acid sequence encoding hAADC is an unmodified DDC cDNA. In further embodiments, the method further comprises the step of: (c) administering a therapeutically effective dose of dopamine-antagonist to the subject. Particular note is made that the dopamine-antagonist can be optionally clozapine, haloperidol, olanzapine paliperidone, quetiapine risperidone, or ziprasidone, optionally administered at a dose from about 0.1 mg daily to about 1000 mg daily.

This invention also includes a method of treating AADC deficiency in a pediatric subject, comprising the steps of: (a) providing a pharmaceutical formulation comprising an AAV2-hAADC vector, (b) delivering the pharmaceutical formulation to the brain of the subject, and (c) administering a therapeutically effective dopamine-antagonist to the subject. The dopamine-antagonist is optionally administered from about the beginning of week-4 after gene-transduction until at least about the end of 12-weeks after gene-transduction. Particular note is made that the dopamine-antagonist can be optionally clozapine, olanzapine paliperidone, quetiapine, risperidone, or ziprasidone. Particular note is made that the dopamine-antagonist is optionally administered at a dose from about 0.1 mg daily to about 1000 mg daily.

This invention also includes a pharmaceutical formulation comprising: (a) an rAAV2 hAADC vector, and (b) 1x PBS. The pharmaceutical formulation optionally further comprises:

(c) about 200 mM NaCl. The pharmaceutical formulation optionally further comprises rAAV2 hAADC vector at a concentration of about $5.7 \times 10^{11}$ vg/mL. Particular note is made that the pharmaceutical formulation optionally further comprises: (d) empty capsids. Particular note is made that the pharmaceutical formulation optionally comprises empty capsids at a percentage of at least about 0.1% cp/cp.

In one aspect, the invention is directed to a method of treating pediatric AADC deficiency in a subject, comprising the steps of: (a) providing a pharmaceutical formulation comprising an rAAV2-hAADC vector, and (b) delivering the pharmaceutical formulation to the brain of the subject; wherein: (i) the pharmaceutical formulation is delivered at a dose of at least about $1.8 \times 10^{11}$ vg, and (ii) the pharmaceutical formulation is delivered using a frameless stereotactic procedure.

Optionally, the dose is at least about $2.4 \times 10^{11}$ vg, at least about $1 \times 10^{12}$ vg, at least about $1 \times 10^{14}$ vg, or at least about $1 \times 10^{16}$ vg. Preferably the dose ranges from about $1.8 \times 10^{11}$ vg to about $1.5 \times 10^{12}$ vg, or ranges from about $1.8 \times 10^{11}$ vg to about $2.4 \times 10^{11}$ vg. More preferably, the dose is about $1.8 \times 10^{11}$ vg, about $2.4 \times 10^{11}$ vg, or about $1.5 \times 10^{12}$ vg.

Optionally, the pharmaceutical formulation is delivered at a rate ranging from of about 0.1 µL/min to about 10 µL/min, or at a rate ranging from about 1 µL/min to about 5 µL/min, or at a rate ranging from about 2 µL/min to about 3 µL/min. Preferably, the pharmaceutical formulation is delivered at a rate of 1 µL/min, 2 µL/min, 3 µL/min, 4 µL/min, 5 µL/min, 6 µL/min, 7 µL/min, 8 µL/min 9 µL/min, or 10 µL/min. More preferably, the pharmaceutical formulation is delivered at a rate of 3 µL/min.

Optionally, the pharmaceutical formulation is delivered at a dose volume ranging from about 1 µL to about 1000 µL per target site, at a dose volume ranging from about 10 µL to about 100 µL per target site, or at a dose volume ranging from about 50 µL to about 100 µL per target site. Preferably, the pharmaceutical formulation is delivered at a dose volume of about 80 per target site.

In one embodiment, the pharmaceutical formulation, comprising a rAAV2-hAADC vector concentration of $5.7 \times 10^{11}$ vg/mL, is delivered to at a dose volume of about 80 µL per target site at a rate of about 3 µL/min.

In one embodiment, the rAAV2-hAADC vector comprises: (a) a WT AAV2 capsid, and (b) a recombinant DNA DDC gene insert comprising: (i) a first AAV2 ITR (ii) a cytomegalovirus (CMV) immediate early promoter (IEP), (iii) a human β-globin partial intron2/exon 3, (iv) a nucleic acid sequence encoding hAADC, (v) a Simian vacuolating virus 40 (SV40) poly A tail, and (vi) a second AAV2 ITR. Preferably, the first and second ITRs flank the other genetic elements of the gene insert. Preferably, the nucleic acid sequence encoding hAADC is an unmodified DDC cDNA.

In one embodiment, the pharmaceutical formulation is delivered to a putamen of the subject, or preferably both putamen of the subject.

Optionally, the pharmaceutical formulation is delivered bilaterally (i.e., to both putamens of the subject). Preferably, the pharmaceutical formulation is delivered to four target points wherein each putamen contains two target points separated dorsolaterally. More preferably, the pharmaceutical formulation is delivered to a deep target point and a shallow target point in each putamen. Optionally, the deep target point is from about the center to about 5 mm from the center of the putamen, or from about the center to about 5 mm from the center of the putamen. Optionally, the shallow target point is from about 10 mm to about 1 mm from the surface of the putamen. Optionally the deep target point is about 5 mm from the center of the putamen. Optionally, the shallow target point is about 5 mm from the surface of the putamen.

Preferably, the two target points are sufficiently distant to each other in the dorsolateral direction, as confirmed by computed tomography (CT) and magnetic resonance imaging (MRI). The stratum is shaped like an ellipse, with a long axis anterior-posterior. The upper half of the stratum is dorsal lateral. The long axis is divided into three sections. The target points are set as the middle two points between the sections. Entry points on the skull and trajectories for injection are drawn so that the catheter will not pass through a blood vessel. The catheter is inserted to a distance about 2 mm away from the target point. The infusion is started. During the infusion, the catheter is drawn back gradually until a distance about 2 mm beneath the margin of the putamen. In one embodiment, the catheter is drawn back at any rate ranging from about 0.1 mm/min to about 2 mm/min. In one embodiment, the catheter is drawn back at a rate of about 0.2 mm/min. In another embodiment, the catheter is drawn back at a rate of about 0.3 mm/min. In another embodiment, the catheter is drawn back at a rate of about 0.4 mm/min. In another embodiment, the catheter is drawn back at a rate of about 0.5 mm/min.

Optionally, the two target points are spaced from about 1 mm to about 10 mm apart, or are spaced from about 2 mm to about 5 mm apart. Optionally, the two target points are spaced about 5 mm apart.

In one embodiment, the method uses a frameless guidance system which is modified for use in children.

In one embodiment, the AAV2-hAADC vector is delivered bilaterally to shallow and deep target points in a subject's putamen. In one embodiment, the method is directed to treating children ranging in age from about 2 to about 8.

Another aspect the invention is directed to a method of treating pediatric AADC deficiency in a subject aged less than about 3 years, comprising the steps of: (a) providing a pharmaceutical formulation comprising an AAV2-hAADC vector; (b) delivering the pharmaceutical formulation to the brain of the subject; wherein: (i) the pharmaceutical formulation is delivered at a dose of at least about $2 \times 10^{11}$ vg, and (ii) the pharmaceutical formulation is delivered using a frameless stereotactic procedure. Optionally, the subject is aged less than about 3 years, aged less than about 2 years, aged less than about 1 year, or aged less than about 6 months. Optionally, the dose is at least about $2 \times 10^{11}$ vg, at least about $2.4 \times 10^{11}$ vg, at least about $5 \times 10^{11}$ vg, at least about $1 \times 10^{12}$ vg, at least about $2 \times 10^{11}$ vg, or at least about $2 \times 10^{12}$ vg. Preferably the dose is about $2.4 \times 10^{11}$ vg per subject.

Another aspect the invention is directed to a method of treating pediatric AADC deficiency in a subject aged about 3 or more years, comprising the steps of: (a) providing a pharmaceutical formulation comprising an AAV2-hAADC vector; (b) delivering the pharmaceutical formulation to the brain of the subject; wherein: (i) the pharmaceutical formulation is delivered at a dose from about $1.8 \times 10^{11}$ vg to about $2.4 \times 10^{11}$ vg, and (ii) the pharmaceutical formulation is delivered using a frameless stereotactic procedure. Optionally, the dose is about $1.8 \times 10^{11}$ vg or about $2.4 \times 10^{11}$ vg per subject. Preferably, the dose is about $1.8 \times 10^{11}$ vg per subject.

Optionally, the frameless trajectory-based stereotactic procedure comprises: (a) installing one or more bone fiducial markers, (b) installing a skull-mounted platform, (c) drilling a burr hole in a side of the skull, (d) locating a target point guided by MRI and CT, (e) inserting a guide tube and stylet to about 2 cm from the target point, (f) removing the stylet and inserting a catheter, and (g) infusing the pharmaceutical formulation. Preferably, the frameless trajectory-based stereotactic procedure further comprises: (h) locating a second target point guided by MRI and CT, (i) inserting a guide tube and stylet to about 2 cm from the second target point, (j) removing the stylet and inserting a catheter, and (k) infusing the pharmaceutical formulation. More preferably, the step of infusing the pharmaceutical formulation comprises withdrawing the catheter allowing the pharmaceutical formulation to be distributed along a tract of about 4 mm to about 8 mm.

Optionally, the fiducial markers comprise stainless steel, titanium or gold. Preferably, the fiducial markers comprise stainless steel.

Optionally, at least about 2, at least about 3, at least about 4, at least about 5, at least 6, at least about 7, at least about 8, at least 9, at least about 10 fiducial markers are installed. Preferably, at least about 4 fiducial markers are installed. More preferably, at least about 8 fiducial markers are installed. Optionally, 2, 3, 4, 5, 6, 7, 8, 9 or 10 fiducial markers are installed. In one embodiment, 8 fiducial markers are installed in a circle on the lower part of the skull bones. In another embodiment, 7 fiducial markers are installed in a circle on the lower part of the skull bones. In another embodiment, 6 fiducial markers are installed in a circle on the lower part of the skull bones. In another embodiment, 5 fiducial markers are installed in a circle on the lower part of the skull bones. In another embodiment, 4 fiducial markers are installed in a circle on the lower part of the skull bones. Without being bound by theory, the fiducial markers are installed on the lower part of the skull bones because the lower part of the skull in thicker.

Another aspect the invention is directed to a method of treating pediatric AADC deficiency in a subject, comprising the steps of: (a) providing a pharmaceutical formulation comprising an AAV2-hAADC vector, (b) delivering the pharmaceutical formulation to the brain of the subject, and (c) administering a dopamine-antagonist to the subject.

Optionally, the dopamine-antagonist is administered simultaneously with gene therapy, is administering beginning at emergence of dyskinesia symptoms, or is administering beginning at about the beginning of week-4 after gene-transduction. Optionally, the dopamine-antagonist is administered for a duration ranging from about 1 week to about 12 weeks. Optionally, the dopamine-antagonist is administered until at least the end of about 4-weeks after gene-transduction, until at least the end of about 6-weeks after gene-transduction, until at least the end of about 8-weeks after gene-transduction, until at least the end of about 10-weeks after gene-transduction, or until at least the end of about 12-weeks after gene-transduction. Optionally, the dopamine-antagonist is administered until the subject no longer exhibits symptoms of dyskinesia. Preferably, the dopamine-antagonist is administered from about the beginning of week-4 until about the end of 12-weeks after gene-transduction.

Optionally, the dopamine-antagonist is clozapine, haloperidol, olanzapine paliperidone, quetiapine risperidone, or ziprasidone. Preferably, the dopamine-antagonist is haloperidol or risperidone. More preferably, the dopamine-antagonist is risperidone.

Optionally, the dopamine-antagonist is administered at a dose from about 0.01 mg daily to about 1000 mg daily, from about 1 mg daily to about 10 mg daily, or from about 0.1 mg daily to about 1 mg daily. In one embodiment, the dopamine-antagonist is administered at a dose of about 0.1 mg per day. In another embodiment, the dopamine-antagonist is administered at a dose of about 0.2 mg per day. In another embodiment, the dopamine-antagonist is administered at a dose of about 0.3 mg per day. In another embodiment, the dopamine-antagonist is administered at a dose of about 0.4 mg per day. In another embodiment, the dopamine-antagonist is administered at a dose of about 0.5 mg per day. In another embodiment, the dopamine-antagonist is administered at a dose of about 0.6 mg per day. In another embodiment, the dopamine-antagonist is administered at a dose of about 0.7 mg per day. In another embodiment, the dopamine-antagonist is administered at a dose of about 0.8 mg per day. In another embodiment, the dopamine-antagonist is administered at a dose of about 0.9 mg per day. In another embodiment, the dopamine-antagonist is administered at a dose of about 1.0 mg per day.

In one embodiment, risperidone is administered at a dose of about 0.1 mg per day. In another embodiment, risperidone is administered at a dose of about 0.2 mg per day. In another embodiment, risperidone is administered at a dose of about 0.3 mg per day. In another embodiment, risperidone is administered at a dose of about 0.4 mg per day. In another embodiment, risperidone is administered at a dose of about 0.5 mg per day. In another embodiment, risperidone is administered at a dose of about 0.6 mg per day. In another embodiment, risperidone is administered at a dose of about 0.7 mg per day. In another embodiment, risperidone is administered at a dose of about 0.8 mg per day. In another embodiment, risperidone is administered at a dose of about 0.9 mg per day. In another embodiment, risperidone is administered at a dose of about 1.0 mg per day.

In one particular embodiment, 0.1 mL of a 1 mg/mL oral solution of risperidone is administered twice daily (BID). In another particular embodiment, 0.2 mL of a 1 mg/mL oral solution of risperidone is administered twice daily.

In one embodiment, the frameless system comprises: installing one or more bone fiducial markers, installing a skull-mounted platform, drilling a burr hole in a side of the skull, locating a target point guided by MRI and CT, inserting a guide tube and stylet toward the target point, removing the stylet and inserting a catheter, and infusing the pharmaceutical formulation.

In another aspect, the invention is directed to a recombinant AAV2-hAADC vector comprising an AAV2 capsid, and a DDC gene insert. In one embodiment, the gene insert comprises: two AAV2 ITRs flanking a CMV IEP promoter, a human β-globin intron-2/exon-3 enhancer, a nucleic acid sequence encoding hAADC, and a SV40 poly A tail. In one embodiment, the rAAV2-hAADC vector comprises: (a) a WT AAV2 capsid, and (b) a recombinant DNA DDC gene insert comprising: (i) a first AAV2 ITR (ii) a CMV IEP promoter, (iii) a human β-globin partial intron 2/exon 3, (iv) a nucleic acid sequence encoding hAADC, (v) an SV40 poly A tail, and (vi) a second AAV2 ITR. Preferably, the first and second ITRs flank the other genetic elements of the gene insert. Preferably, the nucleic acid sequence encoding hAADC is an unmodified DDC cDNA.

In another aspect, the invention is directed to a pharmaceutical formulation. In one embodiment, the pharmaceutical formulation comprises an rAAV2-hAADC vector and one or more pharmaceutically acceptable excipients. In one embodiment, the pharmaceutical formulation comprises a rAAV2-hAADC vector, and 1×PBS. In another embodiment, the pharmaceutical formulation comprises a rAAV2-hAADC vector, 1×PBS, and about 200 mM NaCl.

Optionally, the pharmaceutical formulation comprises a rAAV2-hAADC vector concentration of at least about $1\times10^{11}$ vg/mL, at least about $5\times10^{11}$ vg/mL, at least about $1\times10^{12}$ vg/mL, or at least about $5\times10^{12}$ vg/mL. Preferably, the pharmaceutical formulation comprises a rAAV2-hAADC vector concentration of concentration of about $5.7\times10^{11}$ vg/mL.

In another aspect, the invention is directed to compositions and methods for increasing AADC gene therapy transduction. In one embodiment, the invention provides a pharmaceutical formulation comprising an rAAV2-hAADC vector and empty capsids. Optionally, the empty capsids are present in a percentage of at least about 0.1% cp/cp, at least about 10% cp/cp, at least about 50% cp/cp, at least about 75% cp/cp, or at least about 90% cp/cp.

Optionally, the empty capsids are present in a percentage ranging from about 0.1% to about 90% cp/cp, from about 1% to about 90% cp/cp, from about 10% to about 80% cp/cp, from about 20% to about 70% cp/cp, from about 40% to about 60% cp/cp, from about 10% to about 50% cp/cp, from about 10% to about 25% cp/cp, or from about 25% to about 75% cp/cp.

Preferably the empty capsids are present in at about 10% vg/vg, about 20% vg/vg about 30% cp/cp, about 40% cp/cp, about 50% cp/cp, about 60% cp/cp, about 70% cp/cp, about 80% cp/cp, or about 90% cp/cp. In one particular embodiment, the percentage of empty capsids is at least about 50% cp/cp. In another particular embodiment, the percentage of empty capsids is at least about 88% cp/cp. In another particular embodiment, the percentage of empty capsids is about 88% cp/cp. In another particular embodiment, the pharmaceutical formulation comprises about $1.76\times10^{12}$ cp empty capsids and about $2.4\times10^{11}$ vg rAAV-hAADC vector.

Optionally, the empty capsids are present in a ratio of empty capsids to rAAV2-hAADC vectors of at least about 9 to about 1, at least about 1 to about 1, or at least about 1 to about 9. Optionally, the pharmaceutical formulation comprises empty capsids that are present in an excess over rAAV2 hAADC vectors. In one embodiment, the pharmaceutical formulation comprises empty capsids are present in at least about a 10×excess over rAAV2-hAADC vectors.

BRIEF DESCRIPTION OF THE FIGURES

FIG. 3: Photographs of Surgical Equipment: Swaged catheter.

FIG. 13: Nucleotide sequence of a pAAV-CMV-hAADC-KanR plasmid (SEQ ID NO. 1).

FIG. 14: Nucleotide sequence of a rAAV-hAADC-vector gene insert (SEQ ID NO. 2).

DETAILED DESCRIPTION OF THE INVENTION

Figure 1:
FIG. 1: Biological Substance (rAAV2-hAADC Vector) Diagram.
Figure 2:
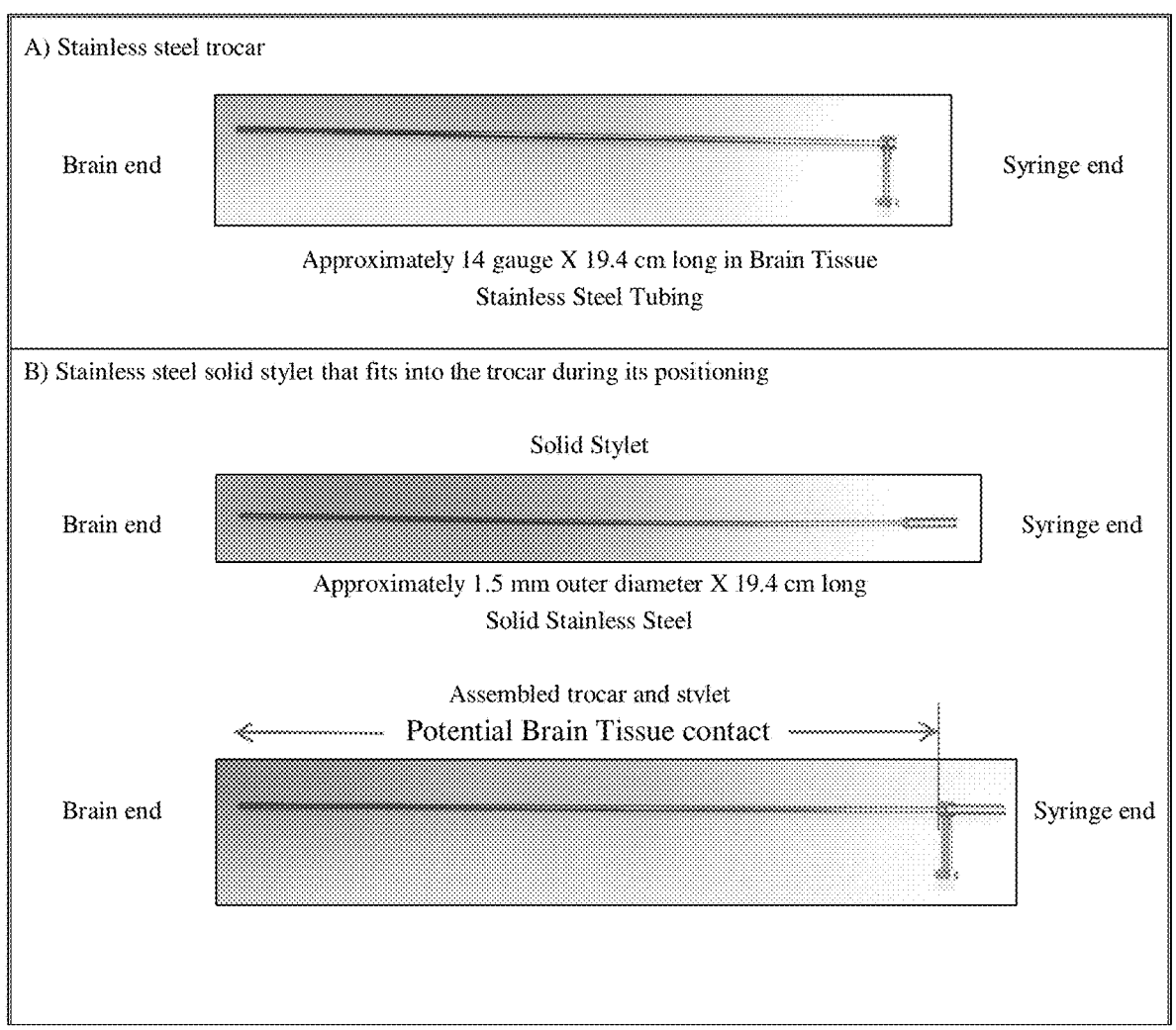
FIG. 2: Photographs of Surgical Equipment: Insertion tube, Stylet.

The present invention provides several advantages over prior AADC gene therapy.

(i) The present invention provides higher doses of rAAV-hAADC vector. (ii) The present invention provides doses of rAAV-hAADC tailored to a patient's age. (iii) The present invention treats or prevents AADC gene therapy induced dyskinesia. (iv) The present invention increases AADC gene therapy transduction. (iv) The present invention limits interference of a patient's immune system. (v) The present invention avoids using onerous skull-fixed head frame stereotaxy. (vi) The present invention offers greater precision, limited surgical exposure, and greater safety.

Definitions

The present invention will best be understood with reference to the following terms: The term "Aromatic L-amino acid decarboxylase" or "AADC" shall mean a polypeptide which decarboxylates dopa to dopamine. (See EC 4.1.1.28; OMIM 107930.) "AADC" includes, but is not limited to, a full-length AADC polypeptide, active fragment or functional homologue thereof. Literature reports that AADC is the final enzyme in the biosynthesis of the monoamine neurotransmitters serotonin and dopamine, and dopamine is the precursor for norepinephrine and epinephrine. See K. et al., "Aromatic amino acid decarboxylase deficiency in twins." J Inherit
  Metab Dis. 1990; 13(3):301-4.

The term "Aromatic L-amino acid decarboxylase deficiency," "AADC deficiency," or "AADCD" shall mean an inherited disorder of monoamine neurotransmitter syntheses reportedly caused by a homozygous or compound heterozygous mutation in the AADC gene DDC on chromosome 7p12 (OMIM 608643). Literature reports that AADC disorder is clinically characterized by vegetative symptoms, oculogyric crises, dystonia, and severe neurologic dysfunction, usually beginning in infancy or childhood. See Brun L, et al., "Clinical and biochemical features of aromatic L-amino acid decarboxylase deficiency," Neurology, 2010 Jul. 6; 75(1):64-71. Literature also reports that AADC deficiency is an autosomal recessive inborn error in neurotransmitter metabolism that leads to combined serotonin and catecholamine deficiency. See N. G. Abeling et al. "Pathobiochemical implications of hyperdopaminuria in patients with aromatic L-amino acid decarboxylase deficiency," J Inherit Metab Dis. 2000 June; 23(4):325-8. Reference is made to Wassenberg et al. "Consensus guideline for the diagnosis and treatment of aromatic L-amino acid decarboxylase (AADC) deficiency" Orphanet Journal of Rare Diseases (2017) 12:12. More than 50 different DDC gene disease-causing variants. A founder splice variant (IVS6+4A>T) is associated with a severe phenotype of AADC deficiency. Medical histories from 37 subjects with AADC deficiency were reviewed for motor development, mutation, and body weight. End points for patients were either their latest follow up, death, or entering into a gene therapy clinical trial. The mean age of these subjects, at the end points, was 4.78 years (1.31-11.33). Of the 37 patients, 36 did not develop a full head control, nor sitting or standing, during any time point from birth to the end points, and none of them developed a speech. Their body weights were normal in the first few months of life, but severe growth retardation occurred during 1-4 years of age. Founder splice variant c.714+4A>T (IVS6+4A>T) represented 76% of subjects' DDC mutations.

The term "AAV" shall mean an adeno-associated virus.

The term "AAV2" shall mean an adeno-associated virus serotype 2.

The term "vector" shall mean a vehicle used to deliver genetic material into a target cell. A vector can be any genetic element, that is capable of replication when associated with the proper control elements and which can transfer gene sequences between cells. Examples of such genetic elements, include but are not limited to, a plasmid, phage, transposon, cosmid, chromosome, virus, or virion. The term includes, but is not limited to, cloning and expression vehicles, as well as viral vectors. A vector can optionally be a gene therapy delivery vehicle, or carrier encapsulating a therapeutic gene for delivery to cells.

The term "recombinant virus" shall mean a virus that has been genetically altered. Examples of alterations include but are not limited to, addition or insertion of a heterologous nucleic acid construct.

The term "AAV virus" shall mean a complete virus particle, for example a wild-type (wt) AAV virus particle. An AAV virus has an AAV capsid protein coat encasing a linear, single-stranded AAV nucleic acid genome. An AAV virus is replication-incompetent (i.e., replication-defective or helper-dependent virus). An intact virus particle may also be referred to as a "virion." An AAV virus is optionally derived from any adeno-associated virus serotype, including without limitation, AAV-1, AAV-2, AAV-3, AAV-4, AAV-5, or AAVX7. AAV viruses can have one or more of the AAV wild-type genes deleted in whole or part, preferably the rep and/or cap genes, but retain functional flanking ITR sequences. Examples of AAV viruses include, but are not limited to, AAV viruses that are available from the American Type Culture Collection ("ATCC") under Accession Numbers 53222, 53223, 53224, 53225 and 53226. For a description of AAV viruses and their uses see, e.g., Haj-Ahmad and Graham (1986) *J. Virol.* 57:267-274; Bett et al. (1993) *J. Virol.* 67:5911-5921; Mittereder et al. (1994) *Human Gene Therapy* 5:717-729; Seth et al. (1994) *J. Virol.* 68:933-940; Barr et al. (1994) *Gene Therapy* 1:51-58; Berkner, K. L. (1988) *BioTechniques* 6:616-629; and Rich et al. (1993) *Human Gene Therapy* 4:461-476.

The term "recombinant AAV," a "rAAV," a "recombinant AAV vector," or a "rAAV vector" shall mean an infectious but replication-defective virus composed of an AAV protein shell (i.e., a capsid) encapsulating a gene insert different from the wild-type AAV DNA.

The term "inverted terminal repeat" or "ITR" shall mean a symmetrical nucleic acid sequence at either end of the genetic material of a virus. Without being bound by theory, literature reports show that ITRs aid the efficient multiplication of the AAV genome. Literature also reports ITRs ability to form a hairpin, which contributes to self-priming that allows primase-independent synthesis of a second nucleic acid strand. ITRs were also shown to aid both integration of AAV DNA into a host cell genome. ITRs need not be the wild-type nucleotide sequences, and may be altered, for example, by the insertion, deletion or substitution of nucleotides, so long as the sequences provide for functional rescue, replication and packaging. Optional nucleotide sequences of AAV ITR regions are known. See, e.g., Kotin, R. M. (1994) "Human Gene Therapy" 5:793-801; Berns, K. I. "Parvoviridae and their Replication" in *Fundamental Virology,* 2nd Edition, (B. N. Fields and D. M. Knipe, eds.)

The term "gene insert" shall mean a nucleic acid molecule encapsulated by capsid, that codes for a sequence of a polypeptide.

The term "gene therapy" shall mean a treatment of a subject comprising the introduction, to a subject, of a normal copy of one or more defective or missing genes. The term "AADC gene therapy" or "DDC gene therapy" shall mean a treatment of a subject comprising the introduction of a normal copy of a DDC gene to a subject that has a defective DDC gene or is missing a DDC gene.

The term "pediatric AADC gene therapy" shall mean a AADC gene therapy treatment of a minor child subject.

The term "subject," "individual," or "patient" shall be used interchangeably and shall mean a mammal, preferably a human in need of therapy. A subject is preferably a minor child aged about 10 years or less. More preferably the subject is aged about 3 years or less.

The term "capsid" shall mean a protein coat or shell of a virus. A capsid optionally comprises one or more oligomeric structural subunits comprising proteins, optionally referred to as protomers. A capsid may optionally be surrounded by a lipid bilayer and glycoprotein envelope. In one embodiment, a capsid is an adeno-associated virus (AAV) capsid. In one particular embodiment, the capsid is a recombinant adeno-associated virus (rAAV) serotype-2 capsid.

The term "empty capsid" shall mean a virus protein coat that does not contain a vector genome. An empty capsid can be a virus-like particle in that it reacts with one or more antibodies that react with intact (e.g., vector genome carrying) virus (e.g. adeno-associated virus, AAV). In a non-limiting example, an empty AAV2 capsid retains the ability to react with one or more antibodies that bind to an AAV, such as an AAV2 or another AAV serotype. For example, an empty AAV2 capsid retains the ability to react with one or more antibodies that bind to AAV8.

Empty capsids may sometimes be naturally found in AAV vector preparations. Such preparations can be used in accordance with the invention. Optionally, such preparations may be manipulated to increase or decrease the number of empty capsids. For example, the amount of empty capsid can be adjusted to an amount that would be expected to reduce the inhibitory effect of antibodies. Empty capsids can also be produced independently of vector preparations, and optionally (i) added to vector preparations, or (ii) administered separately to a subject. See F. Mingozzi et al., U.S. Patent Application Publication No. 2014/0336245 "Virus vectors for highly efficient transgene delivery."

The term "modified capsid" shall mean a content-modified capsid, or a capsid modified so that the capsid is unable to enter a cell.

The term "content-modified capsid" shall mean a capsid carrying a gene insert that is modified. Examples of gene inserts that are modified, include but are not limited to, non-coding nucleic acids.

The term "mutant empty capsid" shall mean an empty capsid comprising a mutation that disrupts virus receptor binding. In one embodiment, a mutant empty capsid is a non-infective mutant capsid. In another embodiment, an empty capsid can absorb an antibody but cannot enter a target cell. In another embodiment, an empty capsid can absorb a neutralizing antibody. See C. J. Aalbers, et al., "Empty Capsids and Macrophage Inhibition/Depletion Increase rAAV Transgene Expression in Joints of Both Healthy and Arthritic Mice," *Human Gene Therapy*, 2017 February; 28(2):168-1781; and Ayuso E, et al. "High AAV vector purity results in serotype- and tissue independent enhancement of transduction efficiency." *Gene Ther* 2010; 17:503-510.

The term "DDC gene insert" shall mean a gene insert comprising a nucleic acid sequence encoding AADC. In one embodiment, gene insert comprises a nucleic acid sequence encoding human AADC (hAADC). In another embodiment, the nucleic acid sequence encoding hAADC is an unmodified DDC cDNA.

The term "enhancer" shall mean a regulatory sequence, outside the promoter, that binds transcription factors. An enhancer is optionally a globin protein, a portion of a globin protein, a human growth hormone, a portion of human growth hormone or a first intron of human growth hormone. Examples of goblin proteins, include but are not limited to, β-globin, human β-globin, human β-globin intron, human β-globin intron 2, partial human β-globin intron 2, human 3-globin exon 3, and partial human β-globin exon 3. In a preferred embodiment, the enhancer is human β-globin partial intron 2/partial exon 3.

The term "plasmid construct" shall mean a circular nucleic acid molecule that replicates independently of a host cell's genetic material. In one embodiment, the plasmid construct comprises: a nucleic acid sequence encoding hAADC, a CMV IEP promoter, an SV40 poly A tail, a human β-globin intron 2/exon 3, two ITRs flanking the gene elements at two ends of the gene insert and an antibiotic resistance gene operably linked to an antibiotic resistance gene The term "antibiotic resistance gene" shall mean a gene conferring resistance to an antibiotic. Examples of antibiotic resistance genes, include but are not limited, to a resistant gene of ampicillin, kanamycin, spectinomycin, streptomycin, carbenicillin, bleomycin, erythromycin, tetracycline, chloramphenicol, and polymyxin B. In one embodiment, the of antibiotic resistance gene is, a resistant gene of ampicillin. In another embodiment, the of antibiotic resistance gene is, a resistant gene of kanamycin.

The term "vector genome" or "vg" shall be broadly understood to encompass gene inserts. For convenience, "vector genomes" shall include, but shall not be limited to, gene inserts encapsulated within capsids such as AAV viruses and rAAV vectors and gene inserts, that are not encapsulated by capsids. For convenience gene inserts, that are not encapsulated by capsids include isolated gene inserts. See U.S. Pat. No. 9,598,703 "Capsid-free AAV vectors, compositions, and methods for vector production and gene delivery"

For quantitative purposes, "vg" is calculated as a count of gene inserts. In one example, of a single "vector genome" or single "vg" is a single gene insert or a single capsid carrying a gene insert. In another example, one rAAV-hAADC vector particle shall mean "1 vg," while about $2.4 \times 10^{11}$ vg shall mean about $2.4 \times 10^{11}$ rAAV-hAADC vectors.

The term "capsid particle" or "cp" shall be broadly understood to encompass any capsid. For convenience, the capsids may be full (e.g., encapsulating a gene insert) or empty. Capsid particles include, but not limited to, capsids carrying vector genomes (e.g., AAV viruses, and rAAV vectors), empty capsids, modified capsids, content-modified capsids, and mutant empty capsids.

For quantitative purposes, "cp" is calculated as a count of the total number of combined capsids carrying vector genomes (e.g., AAV viruses, and rAAV vectors), empty capsids, modified capsids, content-modified capsids, and mutant empty capsids. In one example, "1 cp" shall mean one empty capsid, while about $1.76 \times 10^{12}$ cp shall mean about $1.76 \times 10^{12}$ empty capsids. In another example a pharmaceutical formulation comprising 88% cp/cp empty capsids comprises 88 empty capsid particles per 100 total capsid particles (full and empty). In another example, a pharmaceutical formulation can comprise a total of about $2.0 \times 10^{12}$ cp capsid particles, wherein the pharmaceutical formulation comprises about $2.4 \times 10^{11}$ vg rAAV-hAADC vectors and about $1.76 \times 10^{12}$ cp empty capsids.

The term "transduction" shall mean the transport of a gene to a cell by using a virus particle.

The term "effective amount" or "therapeutically effective amount" is an amount sufficient to affect a therapeutically beneficial or therapeutically desired result. A therapeutically effective amount can be administered in one or more administrations, applications or dosages.

The term "decoy," "decoy particle" or "viral decoy" shall mean a particle or other composition that mimics a virus. The decoy is preferably devoid of virulent activity. Without being bound by theory, a decoy can mimic a native virus in size, shape, structure, or composition thereby causing, and thereby can be consumed by macrophages (e.g., through phagocytosis), leaving functional vectors free to transduce cells. Examples of decoy particles include, but are not limited to, empty capsids, modified capsids, and mutant empty capsids.

The term "dyskinesia" shall mean abnormality of voluntary movement, diminished voluntary movement, impairment of voluntary movement, or involuntary movement.

The term "target point" or "target site" shall mean a location in the brain of a subject where the pharmaceutical formulation is administered. Preferably, the target point is the deepest location of injection.

The term "stereotaxy," "stereotaxis," or "stereotactic procedure" shall mean a method in neurosurgery or neurological research for locating points within the brain using an external, three-dimensional frame of reference usually based on the Cartesian coordinate system.

The term "frameless stereotaxy," "frameless stereotaxis," or "frameless stereotactic procedure" shall mean stereotaxy performed without a head frame. Particularly, "frameless stereotaxy" uses a surgical support bracket instead of a skull-mounted head frame. One example of a surgical support bracket is a Nexframe®—Frameless Surgical Support Bracket (Medtronic, Minneapolis, Minnesota).

The term "fiducial" or "fiducial marker" shall mean an object used as a point of reference or a measure. A fiducial is optionally placed into or on a subject where the fiducial appears in the field of view of an imaging system and the fiducial appears in the image produced. A fiducial marker may also be used as a bone anchor for a frameless stereotaxy skull platform.

The term "homolog" or "homologous sequence" shall be understood to mean a sequence having a percentage identity with the bases of a nucleotide sequence, or the amino acids of a polypeptide sequence, of at least about 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.5%, 99.6%, or 99.7%. This percentage is purely statistical, and it is possible to distribute the differences between the two nucleotide or amino acid sequences at random and over the whole of their length. Sequence identity can be determined, for example, by computer programs designed to perform single and multiple sequence alignments.

The term "substantial homology", when referring to a nucleic acid, or fragment thereof, indicates that, when optimally aligned with appropriate nucleotide insertions or deletions with another nucleic acid (or its complementary strand), there is nucleotide sequence identity in about 90 to 100% of the aligned sequences.

Embodiments of the Present Invention

The present invention is directed to compositions and methods for treating aromatic L-amino acid decarboxylase (AADC) deficiency.

In one aspect, the invention is directed to a vector comprising an adeno-associated virus (AAV) containing the human gene encoding the AADC enzyme (hAADC). In one particular aspect, the invention is directed to vector comprising AAV serotype 2 (AAV2) and a DDC gene insert. In one embodiment, the vector is a rAAV2-hAADC vector comprising an rAAV2 capsid, and a complementary DNA (cDNA) sequence encoding hAADC.

The goal of this therapeutic approach is to increase the amount of AADC in target areas of the central nervous system (CNS) to a level that is sufficient to result in clinical benefit. Without being bound by ant particular theory, it is believed that this goal is accomplished by increasing the production of critical neurotransmitters and subsequently improving neurological function.

In one embodiment, the viral vector of rAAV2-hAADC is an unnatural gene obtained by a genetic engineering by restriction enzyme cleavage and by DNA ligation of human β-globin, where the restriction enzyme cleavage is a cleavage of Cla I, EcoR V, Hind III, Not I, Sac II and Xho I.

The synthesis of an rAAV-hAADC vector may use any current methodology known to persons skilled in the art as well as standard variations of such methods. One non-limiting examples of an rAAV-hAADC vector is described in Fan et al., "Behavioral Recovery in 6-Hydroxydopamine-Lesioned Rats by Cotransduction of Striatum with Tyrosine Hydroxylase and Aromatic L-Amino Acid Decarboxylase Genes Using Two Separate Adeno-Associated Virus Vectors", *Human Gene Therapy* 9:2527-2535, 1998. Other non-limiting examples of rAAV-hAADC vectors are described in C. W. Christine, et al., "Safety and tolerability of putaminal AADC gene therapy for Parkinson disease," *Neurology* 73, 1662-1669 (2009); and S. Muramatsu, et al., "A phase I study of aromatic L-amino acid decarboxylase gene therapy for Parkinson's disease," *Mol. Ther.* 18, 1731-1735 (2010); K. Ozawa et al. U.S. Pat. No. 7,588,757 "Methods of treating Parkinson's disease using recombinant adeno-associated virus virions"; and K. Bankiewicz et al., U.S. Pat. No. 6,309,634, "Methods of treating Parkinson's disease using recombinant adeno-associated vector (rAAV); Wuh-Liang Hwu, et al., "Gene Therapy for Aromatic L-Amino Acid Decarboxylase Deficiency," *Sci. Transl. Med.* 4, 134 (2012); and Wuh-Liang Hwu, et al., U.S. Pat. App. Pub. No. US 2012/0220648.

Optionally, synthesis of the rAAV-hAADC vector uses HEK293/plasmid transfection technology. "Production of adeno-associated virus (AAV) serotypes by transient transfection of HEK293 cell suspension cultures for gene delivery" P. S. Chahal et al., *Journal of Virological Methods*, 2014, Vol. 196, Pages 163-173.

In one embodiment, the gene insert comprises a heterologous nucleic acid and one or more inverted terminal repeats (ITRs). AAV can be constructed using recombinant techniques that are known in the art and include one or more heterologous nucleic acids flanked by ITRs.

ITRs are optionally wild-type nucleotide sequences, or nucleic acid sequences that may be altered. Alterations include but are not limited to, insertion, deletion, or substitution of nucleotides. The sequences can provide for proper function, including but not limited to, rescue, replication, and packaging of an AAV genome. See for example, "Gene Transfer Vectors for Clinical Application," *Methods in Enzymology*; Academic Press, Vol. 507, 1st Ed. (2012).

An example of an rAAV-hAADC vector gene insert is shown in FIG. 1.

//-ITR-CMV-HBG2/3-hAADC-Poly A-ITR-//

ITR=AAV2 inverted terminal repeat,

CMV=cytomegalovirus promoter,

HBG2/3=Human Beta Globin Partial intron 2/partial exon 3, hAADC=human aromatic L-amino acid decarboxylase 1.85 kb cDNA.

Poly A=SV40 poly-adenylation sequence.

Pharmaceutical Formulations:

In another aspect, the invention is directed to a pharmaceutical formulation. A thorough discussion of pharmaceutically acceptable excipients is available in "Remington: The Science and Practice of Pharmacy" ($22^{nd}$ Edition, *Pharmaceutical Press*, New York, NY 2012)

In one embodiment, the pharmaceutical formulation comprises an rAAV2-hAADC vector and one or more pharmaceutically acceptable excipients.

Optionally, the rAAV2-hAADC vector is formulated in phosphate buffered saline (PBS), 1×PBS, 2×PBS, 10×PBS, Dulbecco's PBS (DPBS), or DPBS which does not comprise Magnesium or Calcium.

In one embodiment, the pharmaceutical formulation comprises a rAAV2-hAADC vector, and 1×PBS. In another embodiment, the pharmaceutical formulation comprises a rAAV2-hAADC vector, 1×PBS, and about 200 mM NaCl.

Examples of pharmaceutical formulations include, but are not limited to the pharmaceutical formulations shown in Table 1.

TABLE 1

Example rAAV2-AADC Formulations

| Component | Formulation 1 | Formulation 2 | Formulation 3 | Formulation 4 |
|---|---|---|---|---|
| rAAV2-hAADC | $5.67 \times 10^{11}$ vg/mL | $1.2 \times 10^{12}$ vg/mL | $7.41 \times 10^{11}$ vg/mL | $6 \times 10^{11}$-$9 \times 10^{11}$ vg/mL |
| Excipients | PBS | Dulbecco's PBS (no Mg, no Ca) + 200 mM NaCl | Dulbecco's PBS (no Mg, no Ca) + 200 mM NaCl | PBS |
| pH | 7.39 | | 6.99 | 6.9-7.5 |

Optionally, the pharmaceutical formulation comprises a rAAV2-hAADC vector concentration of at least about $1 \times 10^{11}$ vg/mL, at least about $5 \times 10^{11}$ vg/mL, at least about $1 \times 10^{12}$ vg/mL, or at least about $5 \times 10^{12}$ vg/mL. Preferably, the pharmaceutical formulation comprises a rAAV2-hAADC vector concentration of concentration of about $5.7 \times 10^{11}$ vg/mL or about $7.5 \times 10^{11}$ vg/mL.

Another aspect of the present invention is directed to pharmaceutical formulations and methods of increasing AADC gene therapy transduction. Vector degradation or vector neutralization, before the vector can transduce target cells, can decrease vector expression. Decreased expression may be caused by vector neutralization by macrophages (e.g., through phagocytosis or opsonization by soluble factors). Pharmaceutical formulations optionally comprise agents that influence macrophage activity or macrophage number, which improves efficacy of recombinant AAV vector transgene expression.

In one particular aspect, decoy particles are administered to a subject as part of the disclosed method. A non-limiting example of a decoy particle is an empty capsid. In one particular aspect, empty AAV capsids are administered to a subject as part of the disclosed method.

Much effort in gene-therapy research has been devoted to minimizing the presence of empty capsids. Some researchers believe, counterintuitively, that the presence of empty capsids is advantageous for gene transduction. See J. F. Wright, "AAV Empty Capsids: For Better or Worse?" *Molecular Therapy* 2014 January; 22(1):1-2.; D. Grimm, et al. "Titration of AAV-2 particles via a novel capsid ELISA: packaging of genomes can limit production of recombinant AAV-2" *Gene Therapy*, 1999, Volume 6, Number 7, Pages 1322-1330. Without being bound by theory, literature reports that empty capsids act as decoys and therefore increase the chances that full virus particles will be able to reach target cells. (see C. J. Aalbers, et al., "Empty Capsids and Macrophage Inhibition/Depletion Increase rAAV Transgene Expression in Joints of Both Healthy and Arthritic Mice," *Human Gene Therapy*, 2017 February; 28(2):168-178; F. Mingozzi et al., "Overcoming Preexisting Humoral Immunity to AAV Using Capsid Decoys," *Sci. Transl. Med.* 2013 Jul. 17; 5(194)). Without being bound by theory, literature reports disclose using viral decoys that are incapable of infectious behavior while at the same time being fully capable of effecting an immune response and otherwise being antigenically bioreactive. See N. Kossovsky et al., U.S. Pat. No. 5,334,394 "A Human immunodeficiency virus decoy," and F. Mingozzi et al., U.S. Patent Application Publication No. 2014/0336245 "Virus vectors for highly efficient transgene delivery."

In one embodiment, a pharmaceutical formulation comprises: (a) rAAV2-hAADC vectors, and (b) empty capsids. Optional embodiments include but are not limited to, pharmaceutical formulations, wherein the percentage of empty capsids is at least about 0.1% cp/cp, at least about 10% cp/cp, at least about 50% cp/cp, at least about 75% cp/cp, or at least about 90% cp/cp. Another optional embodiment includes pharmaceutical formulations, wherein the percentage of empty capsids ranges from about 10% to about 90%. In one particular embodiment, the percentage of empty capsids is at least about 88% cp/cp. In another particular embodiment, the pharmaceutical formulation comprises about $1.76 \times 10^{12}$ cp empty capsids, and about $2.4 \times 10^{11}$ vg rAAV-hAADC vector.

Other optional embodiments include, but are not limited to, pharmaceutical formulations, wherein the ratio of empty capsids to rAAV2 hAADC vectors is at least about 9:1, is at least about 1:1, is at least about 1:9. Other optional embodiments include, but are not limited to, pharmaceutical formulations, wherein the ratio of empty capsids to rAAV2 hAADC vectors is any ratio from about 1:1, to about 1:100,000. Other optional embodiments include, but are not limited to, pharmaceutical formulations, wherein the ratio of empty capsids to rAAV2 hAADC vectors is about 1:10 to 1:100, 1:100 to 1:1000, 1:1000 to 1:10,000, 1:10,000 to 1:100,000, or 1:100,000 to 1:>100,000.

Another particular embodiment includes a pharmaceutical formulation, wherein the empty capsids are present in an excess over rAAV2 hAADC vectors. Another particular embodiment, it is useful for empty capsids to be present in any number from about a 10×excess over rAAV2 hAADC vectors to about 1,000,000×excess over rAAV2-hAADC vectors. Other particular embodiments include a pharmaceutical formulation, wherein the empty capsids are present in at least about a 10×excess, 100×excess, or 1,000×excess over rAAV2-hAADC vectors.

In another example, a pharmaceutical formulation can comprise a total of about $2.0 \times 10^{12}$ cp capsid particles, wherein the pharmaceutical formulation comprises about $2.4 \times 10^{11}$ vg rAAV-hAADC vector and about $1.76 \times 10^{12}$ cp empty capsids.

A non-limiting example of a method for increasing AADC gene therapy transduction comprises the steps of: (a) providing a pharmaceutical formulation comprising: (i) an rAAV2-hAADC vector, and (ii) an empty capsid; and (b) delivering the pharmaceutical formulation to the brain of the subject.

In another particular aspect, an rAAV2-hAADC vector, is also administered along with an immunosuppressive agent to a subject as part of the disclosed method. A non-limiting example of a method for increasing AADC gene therapy transduction comprises the steps of: (a) providing a pharmaceutical formulation comprising: (i) an rAAV2-hAADC vector, and (ii) an immunosuppressive agent; and (b) delivering the pharmaceutical formulation to the brain of the subject. Another non-limiting example of a method for increasing AADC gene therapy transduction comprises the steps of: (a) providing a pharmaceutical formulation comprising: (i) an rAAV2-hAADC vector, (ii) an empty capsid, and (iii) an immunosuppressive agent.; and (b) delivering the pharmaceutical formulation to the brain of the subject.

The term "immunosuppressive agent" shall mean a composition that inhibits or prevents activity of a subject's immune system. Without being bound by theory, literature reports believe that immunosuppressive agents act by inhibiting the activation and proliferation of immune cells, including macrophages. See Gummert et al., "Newer Immunosuppressive Drugs; A Review," *J. Am. Soc. Nephrol.* 10:1366-1380, 1999; B. Huang et al. "Advances in Immunotherapy for Glioblastoma Multiforme." *J. Immunol. Res.*, 2017:3597613.) Examples of immunosuppressive agents, include but are not limited to, corticosteroids, glucocorticoids, mineralocorticoids, cytostatics, antibodies, and drugs acting on immunophilins. Examples of corticosteroids, include but are not limited to, triamcinolone, triamcinolone acetonide, hydrocortisone, methylprednisolone, prednisolone, prednisone, amcinonide, budesonide, desonide, fluocinolone acetonide, fluocinonide, halcinonide, and triamcinolone acetonide, beclometasone, betamethasone, dexamethasone, fluocortolone, halometasone, and mometasone. Alclometasone dipropionate, betamethasone dipropionate, betamethasone valerate, clobetasol propionate, clobetasone butyrate, fluprednidene acetate, and mometasone furoate. ciclesonide, cortisone acetate, hydrocortisone aceponate, hydrocortisone acetate, hydrocortisone buteprate, hydrocortisone butyrate, hydrocortisone valerate, prednicarbate, and tixocortol pivalate.

Optionally, the immunosuppressive agent is a macrophage depletion agent. In one embodiment, the macrophage depletion agent is a clodronate liposome. Without being bound by theory, literature reports believe that clodronate liposomes deplete macrophages by inducing apoptosis in phagocytes following phagocyte recognition and uptake. (See, A. Reszka et al., "Mechanism of action of bisphosphonates," *Current Osteoporosis Reports*, 1 (2003) 45-52, and R. G. G. Russell, "Bisphosphonates: The first 40 years," *Bone*, 49 (2011) 2-19.)

One non-limiting example of a clodronate liposomes includes Clodrosome® liposomal clodronate; (Encapsula NanoSciences LLC Brentwood, TN) Clodronate Disodium Salt, 5 mg/mL, 17 mM; L-α-Phosphatidylcholine, 18.8 mg/mL, 24 mM; Cholesterol, 4.2 mg/mL, 11 mM; Suspended in Phosphate Buffered Saline at pH 7.4, multilamellar liposomes (size range of 0.3-3 μm). A Clodrosome® Macrophage Depletion Kit (Encapsula NanoSciences LLC Brentwood, TN) comprises a vial of clodronate encapsulated liposomes and a vial of plain liposome for control.

Optionally the clodronate liposomes comprises a mannosylated liposome. A non-limiting example of a mannosylated liposome comprises monoMan3-glutaryl-phosphatidylethanolamine, a phospholipid derivative displaying a branched mannose structure on the surface of the liposome. One non-limiting example of a clodronate liposomes kit includes (m-Clodrosome® Mannosylated Clodrosome Macrophage Depletion Kits; Encapsula NanoSciences LLC Brentwood, TN) comprising (a) a vial of Clodronate encapsulated mannosylated liposomes (4-Aminophenyl-alpha-D-Mannopyranoside incorporated into the liposomes: size range (0.3-3 μm) Suspended in Phosphate Buffered Saline at pH 7.4: Clodronate Disodium Salt 5 mg/mL 17 mM; L-α-Phosphatidylcholine 18.8 mg/mL 24 mM; Cholesterol 4.2 mg/mL 11 mM; 4-Aminophenyl-alpha-D-Mannopyranoside 1 mg/mL 3.69 mM) and (b) a vial of plain mannosylated liposome for control (m-Encapsome®) (Encapsula NanoSciences LLC Brentwood, TN).

In one embodiment, an immunosuppressive agent is optionally administered about 48 hours before vector administration, about 24 hours before vector administration, about 12 hours before vector administration, about 6 hours before vector administration. In another embodiment, an immunosuppressive agent is adminstered at about the same time as the vector administration. In another embodiment, an immunosuppressive agent is adminstered as a component of the pharmaceutical formulation comprising the vector. In another embodiment, an immunosuppressive agent is adminstered at a time ranging from about 6 hours to about 48 hours after vector administration.

In one embodiment of the present invention, the stereotactic procedure uses a StealthStation® Integrated Navigation System (Medtronic, Minneapolis, Minnesota). (See R. Heermann et al., "Navigation with the StealthStation™ in Skull Base Surgery: An Otolaryngological Perspective," *Skull Base*. 2001; 11(4): 277-285; and M T Stechison et al., "A digitized biopsy needle for frameless stereotactic biopsies with the StealthStation," *Neurosurgery*. 2000 January; 46(1):239-41; discussion 241-2.) In another embodiment, the stereotactic procedure uses a Curve™ Image Guided Surgery (BrainLAB, Heimstetten, Germany). (See "Navigating Surgery: Latest Image-Guided Technology Promises to Lead the Way," *Journal of Clinical Engineering*: January/March 2012—Volume 37—Issue 1—p 12, the contents of which are incorporated herein it its entirety). Without being bound by theory, StealthStation® and Curve™ Image Guided Surgery use cameras or electromagnetic fields to capture and relay a subject's anatomy and the surgeon's precise movements in relation to the subject, to computer monitors in the operating room. Computerized systems are used before and during surgery to help orient the surgeon with three-dimensional images of the subject's anatomy.

Frameless stereotaxy typically uses pre-operative magnetic resonance imaging (MM) to patients using surface scalp anatomy or fiducial scalp markers. Optionally, Frameless stereotaxy uses a high-field intra-operative MRI (iMRI). Without being bound by theory, literature reports that a patient's scalp may shift slightly between pre-operative imaging and final surgical positioning with pinion placement, possibly introducing error. Frameless stereotaxy using (iMRI) may compensate for such errors.

Frameless stereotaxy is commonly understood to use a surgical support bracket instead of a skull-mounted head frame. In one embodiment of the present invention, the surgical support bracket is a Nexframe®—Frameless Surgical Support Bracket (Medtronic, Minneapolis, Minnesota). The Medtronic Nexframe Stereotactic System is a disposable, frameless, stereotactic guidance system used in conjunction with image-guided surgery (IGS) systems for intracranial surgical procedures. (see R. A. Vega et al. "Image-Guided Deep Brain Stimulation" *Neurosurgery Clinics of North America*, 2014; 25(1):159-172; J. M. Henderson et al., "The application accuracy of a skull-mounted trajectory guide system for image-guided functional neurosurgery." *Comput. Aided Surg.* 2004; 9(4):155-60; and KL Holloway, et al., "Frameless stereotaxy using bone fiducial markers for deep brain stimulation," *J. Neurosurg.* 2005; 103(3):404-413.) Another non-limiting example of a frameless procedure is Novalis® Radiosurgery (BrainLAB, Heimstetten, Germany). (See R. E. Wurm, et al., "Novalis Frameless Image-Guided Noninvasive Radiosurgery frameless image-guided noninvasive radiosurgery: Initial Experience," *Neurosurgery* (2008) 62 (suppl_5): A11-A18.) (See also A. D. Mehta et al., "Frameless stereotactic placement of depth electrodes in epilepsy surgery," *J Neurosurg.* 2005 June; 102(6):1040-5).

It is commonly understood that skulls of children are not fully developed and have bone areas that are fragile, uneven or not fused. In aspects where the surgical support bracket cannot be secured to the skull by screws, the surgical support bracket is held in place by a head holder. A head holder, also referred to as a head clamp or a skull clamp, is commonly understood to be a device used to secure a subject's head position during surgical procedures. Optionally, the head holder comprises a flexible arm. The head holder is tightened with a force appropriate for the subject's skull bone thickness and bone quality. One non-limiting example of a head clamp is a Mayfield® Infinity Skull Clamp (*Integra LifeSciences Corporation*, Plainsboro, NJ). (See U.S. Pat. No. 5,254,079; "Head Clamp.") Reference is made to the "FDA Safety Communication: Neurosurgical Head Holders (Skull Clamps) and Device Slippage," dated Feb. 25, 2016. Reference is also made to C. Berry et al., "Use of cranial fixation pins in pediatric neurosurgery," *Neurosurgery*, 2008; 62(4): 913-919; and J. C. Poli et al., "Epidural hematoma by Mayfield head-holder: case report and review of literature," *Journal of Pediatric Sciences*, 2013; 5: e195.

In one embodiment of the present invention, the platform of a Nexframe® Frameless Surgical Support Bracket is held in place against a subject's skull by a flexible arm operating as a head clamp. Optionally the Nexframe® platform is operably attached to the flexible arm using an adapter. Tightening the flexible arm presses the platform against the skull of the subject. In one particular embodiment, the Nexframe® is held in place against a subject's skull by a Mayfield® Infinity Skull Clamp. Optionally the Nexframe® platform is operably attached to the Mayfield® Infinity Skull Clamp using an adapter. Optionally any suitable adapter known in the art is used.

In one embodiment, the frameless stereotactic procedure comprises the steps of: (a) installing one or more bone fiducial markers, (b) installing a skull-mounted platform, (c) drilling a burr hole in a side of the skull, (d) locating a target point guided by Mill and CT, (e) inserting a guide tube and stylet at or near the target point, (f) removing the stylet and inserting a catheter, and (g) infusing the pharmaceutical formulation.

For administering the pharmaceutical formulation to a second target in a putamen, the frameless trajectory-based stereotactic procedure further comprises: (h) locating a second target point guided by MM and CT, (i) inserting a guide tube and stylet at or near the second target point, (j) removing the stylet and inserting a catheter, and (k) infusing the pharmaceutical formulation.

In one embodiment, the guide tube and stylet are inserted from about 1 cm to about 5 cm from a target point. In another embodiment, the guide tube and stylet are inserted about 2 cm from a target point.

In one embodiment, the infusion method includes administration of the pharmaceutical formulation wherein the catheter is withdrawn allowing the pharmaceutical formulation to be distributed along a tract of about 1 mm to about 20 mm. In one particular embodiment, the catheter is withdrawn allowing the pharmaceutical formulation to be distributed along a tract of about 5 mm to about 10 mm. In another particular embodiment, the catheter is withdrawn allowing the pharmaceutical formulation to be distributed along a tract of about 6 mm to about 8 mm.

It is commonly known in the art that a fiducial marker or fiducial is an object placed in the field of view of an imaging system which appears in the image produced, for use as a point of reference or a measure. It may be either something placed into or on the imaging subject, or a mark or set of marks in the reticle of an optical instrument. One or more fiducial markers are useful in conducting the stereotactic procedure described herein. It is useful to use any number of markers from about 2 to about 20. See E. M. Thompson et al. "Skull-fixated fiducial markers improve accuracy in staged frameless stereotactic epilepsy surgery in children" *J Neurosurg Pediatr.* 2011, 7(1):116-9; and C. R. Maurer, Jr. et al. "Registration of Head Volume Images Using Implantable Fiducial Markers" *IEEE Transactions on Medical Imaging*, 1997, vol. 16, no. 4, 447. It is useful to install the fiducial markers in a circular or square manner. Optionally, at least about 4, at least about 6, at least about 8, at least about 10 fiducial markers are installed. Preferably, at least about 4 fiducial markers are installed. More preferably, at least about 8 fiducial markers are installed. Optionally, 4, 6, 8, or 10 fiducial markers are installed. In one embodiment, 8 fiducial markers are installed in a generally circular manner on the lower part of the skull bones. Without being bound by theory, the fiducial markers are installed on the lower part of the skull bones because the lower part of the skull are thicker or less fragile.

Fiducial markers our optionally threaded and positioned by screwing the fiducials into a subject's skull. In some embodiments, the fiducials are self-tapping threaded screws. Optionally the fiducials are operably attached to self-tapping threaded screws. Fiducial markers upon installation, preferably avoid regions where the skull bones are too thin or fragile. Without being bound by theory, for children, the risk of skull fracture is pronounced when the bone is less than about 3 mm thick.

Other Fiducial markers are installed by adhering the fiducials to a subject's scalp using an adhesive including, but not limited to, tape or glue.

Fiducial markers may be made of any surgically suitable material. For example, fiducial markers optionally comprise stainless-steel, titanium or gold. In one embodiment, the fiducial markers are stainless-steel fiducial markers.

Fiducial markers are optionally about 1 mm to about 10 mm in length and about 1 mm to about 10 mm in width.

In one embodiment, the fiducial marker is a stainless-steel self-tapping screw (about 2.0 mm×about 5.0 mm). Without being bound by theory, stainless steel self-tapping screws provide optimal contrast again the bone and minimize migration. In another embodiment, the fiducial marker is a self-adhesive, Modality Fiducial Marker (about 15 mm outer-diameter and about 3.5 mm thick). (Brain Lab AG, product 52160). Reference is made to "Principles and Practice of Stereotactic Radiosurgery," L. S. Chin, Ed. Springer, 2008. Reference is also made to E. M. Thompson, et al., "Skull-fixated fiducial markers improve accuracy in staged frameless stereotactic epilepsy surgery in children," *Journal of Neurosurgery: Pediatrics*, 2011, 7(1) 116-119; and D. Chen et al., "Automatic fiducial localization in brain images" *International Journal of Computer Assisted Radiology and Surgery*, 2006; M Wang et al., "Automatic localization of the center of fiducial markers in 3D CT/MRI images for image-guided neurosurgery" *Pattern Recognition Letters*, 2009, 30 (4), 414-420; F. R. Kahn "Deep Brain Stimulation Surgical Techniques," Handbook of Clinical Neurology 2013, ch.3., pg. 27; and K. L. Holloway, "Frameless stereotaxy using bone fiducial markers for deep brain stimulation," Journal of Neurosurgery, 2005, 103(3) 404-413.

Delivery of Pharmaceutical Formulation:

The pharmaceutical formulation can be delivered by manual injection, by an infusion pumps or by an osmotic pump. Non-manual injection includes, but in not limited to, convection enhanced delivery (CED). Both osmotic and infusion pumps are commercially available from a variety of suppliers, for example Alzet Corporation, Hamilton Corporation, Alza, Inc., Palo Alto, Calif.). One non-limiting example of a syringe pump is a Pump 11 Elite Series, Harvard Pump, Harvard Apparatus Holliston, MA. One non-limiting example of a syringe pump is a Legato™ Syringe Pump, KD Scientific Inc. Holliston, MA.

The pharmaceutical formulation is optionally delivered by catheter and infusion pump. Any catheter and pump combination suitable for brain infusion is optionally used.

Stereotactic maps and positioning devices are available, for example from ASI Instruments, Warren, Mich. Positioning may also be conducted by using anatomical maps obtained by CT and/or MRI imaging of the subject's brain to help guide the injection device to the chosen target.

Another aspect of the present invention is directed to post-operative clinical management of dyskinesia. The present invention includes formulations and methods for preventing, ameliorating, treating, or reducing Dyskinesia caused by AADC gene-therapy. In one embodiment, the invention is directed to method of treating post hAADC gene-therapy dyskinesia in a subject comprising: administering a dopamine-antagonist to the subject.

Without being bound by theory, Post Gene-Transduction Dyskinesia is believed to be a transient, self-limited, phenomenon. However, the dyskinesia can disturb a patient's sleep. Orofacial dyskinesia can interfere with swallowing of food or saliva, and may be dangerous if the severity is high.

Without being bound by theory, the mechanism of dyskinesia is believed to include, but is not limited to, (i) Post-synaptic hypersensitivity and (ii) a Motor learning period. Post-synaptic hypersensitivity: Dopamine receptors become very sensitive after prolonged period of dopamine deficiency. Post-synaptic hypersensitivity may be the reason that younger patients often experienced less severe dyskinesia. Motor learning period: Purposeful motor movements come from learning, and therefore the movements of young infants all are dyskinesia. The first movements in patients after restoration of dopamine are first dyskinesia and then gradually transformed to controlled movement, if neural plasticity remains.

A dopamine-antagonist is optionally administered at or during the following times: (i) simultaneously with gene therapy, (ii) beginning at emergence of dyskinesia symptoms, (iii) beginning at about the beginning of week-4 after gene-transduction, (iv) until the end of about 12 weeks after gene-transduction, or (v) from about the beginning of week-4 until about the end of 12 weeks after gene-transduction.

Examples of dopamine-antagonists include, but are not limited to, clozapine, haloperidol, olanzapine paliperidone, quetiapine risperidone, or ziprasidone. In one particular embodiment, the dopamine-antagonist is haloperidol or risperidone. In another particular embodiment, the dopamine-antagonist is risperidone.

The dopamine-antagonist optionally may be administered at a dose from about 1 mg daily to about 1000 mg daily, at a dose from about 1 mg daily to about 10 mg daily, or at a dose from about 0.5 mg daily to about 1 mg daily. In one particular embodiment, the dopamine-antagonist is administered at a dose of about 0.5 mg per day. In another particular embodiment, the risperidone is administered at a dose of about 0.5 mg per day.

Container:

In one embodiment, the pharmaceutical formulation is contained in a pharmaceutical-grade borosilicate glass container with a fluoropolymer lined plastic closure. Examples of fluoropolymers include, but are not limited to, polytetrafluoroethylene (PTFE) (Teflon®). polyethylenetetrafluoroethylene (ETFE). (Fluorotec®), and a copolymer of ethylene and tetrafluoroethylene (Tefzel®). In one embodiment, the closure is lined with polytetrafluoroethylene (PTFE) (Teflon®).

Dose:

Reference is made to Wassenberg et al. "Consensus guideline for the diagnosis and treatment of aromatic L-amino acid decarboxylase (AADC) deficiency" *Orphanet Journal of Rare Diseases* (2017) 12:12.

In one embodiment of the instant invention, the dose per subject ranges from about $1.8 \times 10^{11}$ vg to about $2.4 \times 10^{11}$ vg. In another embodiment, the dose is at least about $2.4 \times 10^{11}$ vg, at least about $1 \times 10^{12}$ vg, or at least about $1 \times 10^{14}$ vg. In another embodiment, the dose is about $1.8 \times 10^{11}$ vg, about $2.4 \times 10^{11}$ vg, or about $1.5 \times 10^{12}$ vg.

The dose is a total dose per subject per administration over all target sites. For one non-limiting example, a total dose per subject of about $1.8 \times 10^{11}$ vg includes four injections of about $4.5 \times 10^{10}$ vg (i.e., one $4.5 \times 10^{10}$ vg injection at each of two target sites in each of a subject's two putamen). For another non-limiting example, a total dose volume per subject of about 320 µL includes four injections of about 80 µL (i.e., one 80 µL injection at each of two target sites in each of a subject's two putamen).

Dose Volume:

In one embodiment, the pharmaceutical formulation is delivered at a dose volume ranging from about 1 µL to about 1000 µL per target site. In another embodiment, the pharmaceutical formulation is delivered at a dose volume ranging from about 10 µL to about 100 µL per target site. In another embodiment, the pharmaceutical formulation is delivered at a dose volume ranging from about 50 µL to about 100 µL per target site. In one particular embodiment, the pharmaceutical formulation is delivered at a dose volume of 80 µL per target site.

Dose Concentration:

In one embodiment, the pharmaceutical formulation comprises an rAAV2-hAADC vector concentration of at least about $1 \times 10^{9}$ vg/mL. In another embodiment, the rAAV2-hAADC vector concentration is at least about $1 \times 10^{10}$ vg/mL, at least about $1 \times 10^{11}$ vg/mL, or at least about $1 \times 10^{12}$ vg/mL. In another embodiment, the rAAV2-hAADC vector concentration is at least about $5 \times 10^{11}$ vg/mL. In one particular embodiment, the pharmaceutical formulation comprises an rAAV2-hAADC vector concentration of about $5 \times 10^{11}$ vg/mL.

Rate of Administration:

In one embodiment, the pharmaceutical formulation is delivered at a rate ranging from of about 0.1 µL/min to about 10 µL/min.

In another embodiment, the pharmaceutical formulation is delivered at a rate of about 1 µL/min, about 2 µL/min, about 3 µL/min, about 4 µL/min, about 5 µL/min, about 6 µL/min, about 7 µL/min, about 8 µL/min about 9 µL/min, or about 10 µL/min. In one particular embodiment, the pharmaceutical formulation is delivered at a rate of about 3 µL/min.

In one embodiment, the pharmaceutical formulation, comprising a rAAV2-hAADC vector concentration of 5.7×

$10^{11}$ vg/mL, is delivered to at a dose volume of about 80 µL per target site at a rate of about 3 µL/min.

Outcome Measures:

Safety data including adverse events, physical and neurologic examinations, vital signs, clinical laboratory tests, EKGs, brain imaging (CT/MRI), anti-AAV2 antibodies, and viral shedding assay results (blood, urine) are summarized.

Efficacy data for the following clinical outcome measures: developmental tests for cognitive and motor function, MRI and CT assessments, FDOPA Positron Emission Tomography (PET) putamen-specific radioactivity uptake values, CSF neurotransmitter metabolite values, neurological evaluation, viral shedding, and monitoring for anti-AAV2 antibody production.

Motor/Developmental Tests:

The primary efficacy assessments of treatment with AADC gene therapy rely on the use of well-established motor and developmental tests administered at specified times before surgery, during the first year after surgery, and at other times as detailed in the study protocols.

Peabody Developmental Motor Scale (PDMS-II):

The Peabody Developmental Motor Scale, Second Edition (PDMS-II), is a skill-based measure of gross and fine motor development for infants and children from birth through 5 years of age. This tool separates motor development into gross and fine motor skills. Through a combination of the composite scores for the gross and fine motor skills, the examiner has a reliable estimate of the child's motor skills. It consists of 4 gross motor and 2 fine motor subtests, as follows: Reflexes (gross motor); Stationary (gross motor); Locomotion (gross motor); Object Manipulation (gross motor); Grasping (fine motor); and Visual-Motor Integration (fine motor).

Scoring the PDMS-II relies on raw scores, percentiles, standard scores, and age equivalents for the subtests, and quotients for the composites. Raw scores are total points accumulated by a child on a subtest. Developmental ages are often used to convey information to parents of young children. Age equivalents for PDMS-II are called "motor ages" which convey to parents that their child is "passing" on items that a child of a certain chronological age would typically pass. Age equivalents for PDMS-II subtests are generated from Table C.1 in the PDMS-II manual or by PDMS-II software scoring and report systems.

Alberta Infant Motor Scale:

The Alberta Infant Motor Scale (AIMS) is a 58-item observational measure of infant motor performance for use from birth through the age of independent walking (~18 months). It assesses the sequential development of motor milestones in terms of progressive development and integration of antigravity muscle control. The population intended for assessment with AIMS is pre- and full-term infants who are developing typically but are "at risk" due to pre-, peri-, or post-natal factors, and who display typical patterns of movement, although these may be delayed or immature. The assessment tool is appropriate for identifying infants with all forms of motor delays, including those who are exhibiting immature motor development as well as those who have severe motor delays involving abnormal patterns of movement. The assessment requires minimal handling and assesses infant movement in 4 positions: prone, supine, sitting, and standing.

The AIMS total score is calculated by summing the scores for the 58 items with a range of scores between 0 and 58. Higher scores indicate more mature motor development.

The infant's score can then be converted to a percentile and compared with age-equivalent peers from the normative sample.

Bayley Scales of Infant and Toddler Development®—Third Edition:

Bayley Scales of Infant and Toddler Development, Third Edition (Bayley-III) offers a standardized assessment of cognitive and motor development for children between 1 and 42 months of age. The assessment measures cognitive, communication, physical, social/emotional, and adaptive areas of development to identify children with developmental delays. The test consists of 5 scales of development: Cognitive Scale, Language Scale, Motor Scale, Social Emotional Scale, and Adaptive Behavior Scale. It is possible to present results for developmental age corresponding to each subscale vs chronological age.

Comprehensive Developmental Inventory for Infants and Toddlers:

The diagnostic test of the Comprehensive Developmental Inventory for Infants and Toddlers (CDIIT) is one of the child developmental tests covering 5 developmental subtests used for children aged 3 to 72 months.

EXAMPLES

Examples are offered for illustrative purposes only, and are not intended to limit the scope of the present invention in any way.

AAV2 Vector Manufacture

Viral particles, including but not limited to, vectors, virions, gene delivery vehicles, capsids and empty capsids, useful in the practice of the present invention, can be constructed using methods well known in the art of molecular biology. Viral vectors carrying transgenes can be assembled from polynucleotides encoding the transgene, suitable regulatory elements and elements necessary for production of viral proteins that mediate cell transduction.

Figure 7:
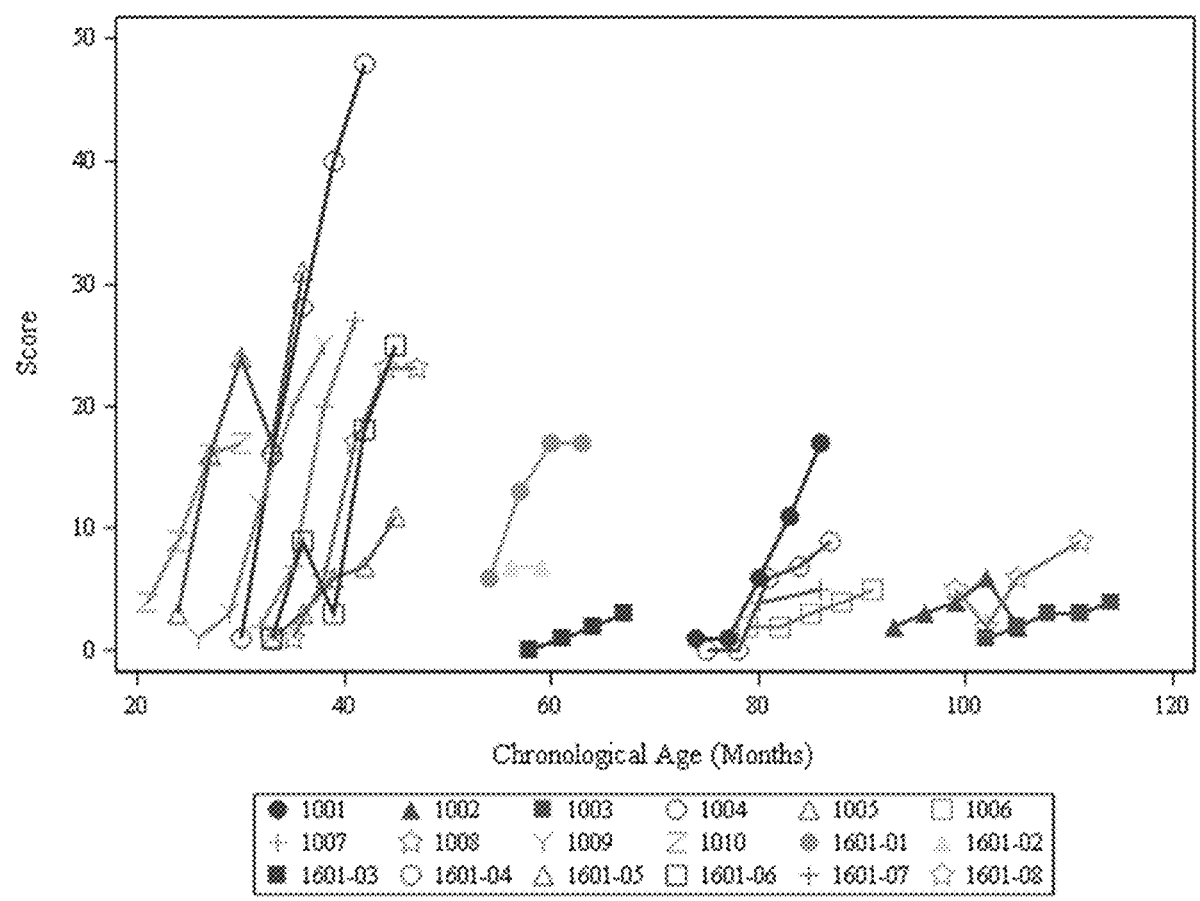
FIG. 7: Graphical representation of AIMS Total Scores by Subject and Chronological Age (n=18).
Figure 8:
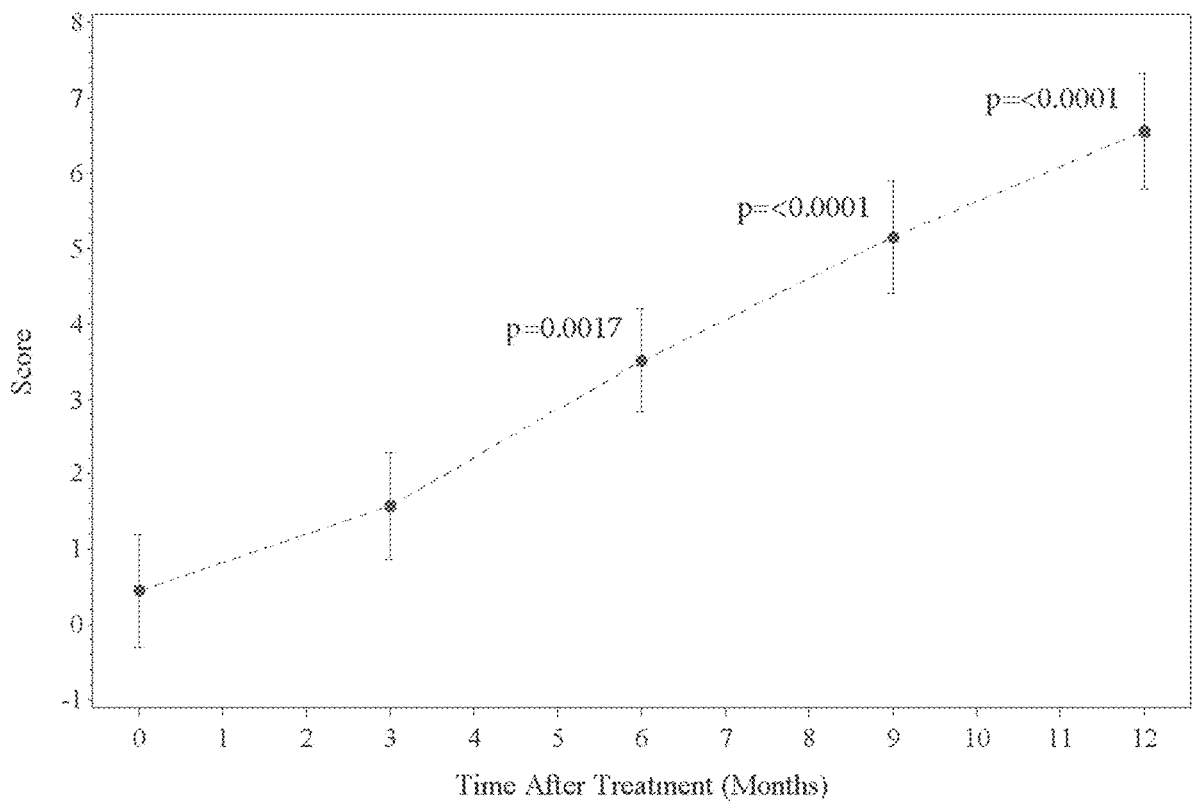
FIG. 8: Graphical representation of LS means and SE for AIMS total score over time through 12 months after vector administration (n=18).

Manufacturing Process Summary:

A schematic of the vector manufacturing process is shown in FIG. 7. The final product, Recombinant Adeno-associated Virus Serotype 2 human L-aromatic amino acid decarboxylase (rAAV2-CMV-hAADC) is usefully produced in a campaign mode in compliance with cGMP. The vector is produced in 293 human embryonic kidney cells using a co-transfection procedure. After expansion of 293 cells, which originate from a working cell bank, into 10-layer CellSTACKS, cells are co-transfected using a $CaPO_4$ precipitation method with the helper and vector plasmids (pDG-KanR and pAAV-CMV-hAADC-KanR). A schematic plasmid Map of pAAV-CMV-hAADC-KanR DNA is shown in FIG. 8. After approximately 72 hours, cells are harvested. The rAAV2-CMV-hAADC Harvest is frozen and stored.

A representative example of a pAAV-CMV-hAADC-KanR plasmid nucleotide sequence (SEQ ID NO. 1) is shown in FIG. 13. Embodiments of the present invention include, but are not limited to functional homologues of the pAAV-CMV-hAADC-KanR plasmid nucleotide sequence (SEQ ID NO. 1).

A representative example of a gene insert is a nucleotide sequence nucleotide sequence (SEQ ID NO. 2) is shown in FIG. 14. The sequence represents the pAAV2-CMV-hAADC plasmid from the beginning of the left ITR to the end of the right ITR, i.e. 23-3725. Embodiments of the present invention include, but are not limited to functional homologues of the nucleotide sequence (SEQ ID NO. 2).

Cell harvest is thawed, lysed in 20 mM Tris/150 mM NaCl with 0.5% Octyl Phenol Oxylate with Benzonase® and then disrupted by microfluidization. Virions are then purified by Heparin Sepharose affinity chromatography. Peak fractions are collected after elution with Phosphate Buffered Saline (PBS)+200 mM NaCl (HE Intermediate). The HE Intermediate peak is increased to approximately 1M NaCl and processed further by Phenyl Sepharose chromatography, and the rAAV2 flow through are collected. Each of the flow through fractions are diluted with WFI and further purified by sulfopropyl cation exchange chromatography and the first peak collected by elution with PBS+200 mM NaCl (Purified Bulk). The Purified Bulk is stored frozen for up to one year.

In-process testing is performed on Harvests and Purified Bulk. The Purified Bulk that meets set specifications are filtered and concentrated using Hollow Fiber Cartridge ultrafiltration (GE Healthcare) Hollow Fiber Cartridge MWCO=300,000) combined into one container, sterile filtered, and then vialed. Final product testing is performed on randomly selected final product vials.

Analysis of Full and Empty Capsids

The count of full and empty capsids is, in one embodiment, accomplished using transmission electron microscopy and chromatography. One chromatographic method, which uses a linear gradient elution on CIM QA disk, assesses charge differences between full and empty capsids (see BIA Separations 2015, M. Lock, et al.: "Analysis of Particle Content of Recombinant Adeno-Associated Virus Serotype 8 Vectors by Ion-Exchange Chromatography." *Human Gene Therapy Methods: Part B* 23:56-64 (2012)).

Other counting techniques include but are not limited to (i) CsCl or iodixanol gradients, and (ii) electron microscope (EM) assay, total particle assay (ELISA) combined with genome copy titration (qPCR). Reference is also made to J. M. Sommer, "Quantification of Adeno-Associated Virus Particles and Empty Capsids by Optical Density Measurement" *Molecular Therapy* 2003; 7(1):122-128, and D. Grimm, et al. "Titration of AAV-2 particles via a novel capsid ELISA: packaging of genomes can limit production of recombinant AAV-2" *Gene Therapy*, 1999, Volume 6, Number 7, Pages 1322-1330. Methods for separating empty capsids from full capsids, include but are not limited to, those provided in U.S. Pat. No. 8,137,948, "Methods for Producing Preparations of Recombinant AAV Virions Substantially Free of Empty Capsids."

Equipment for Delivering Pharmaceutical Composition:

1) Stainless steel insertion tube (trocar): Approximately 14 gauge×19.4 cm long; Stainless Steel Tubing suitable for brain insertion (Medtronic) (FIG. 3)

2) Stainless steel solid stylet that fits into the insertion tube during its positioning: Removed and replaced by swaged catheter; Solid Stylet; Approximately 1.5 mm outer diameter×19.4 cm long; Solid Stainless Steel suitable for brain insertion.

Figure 4:
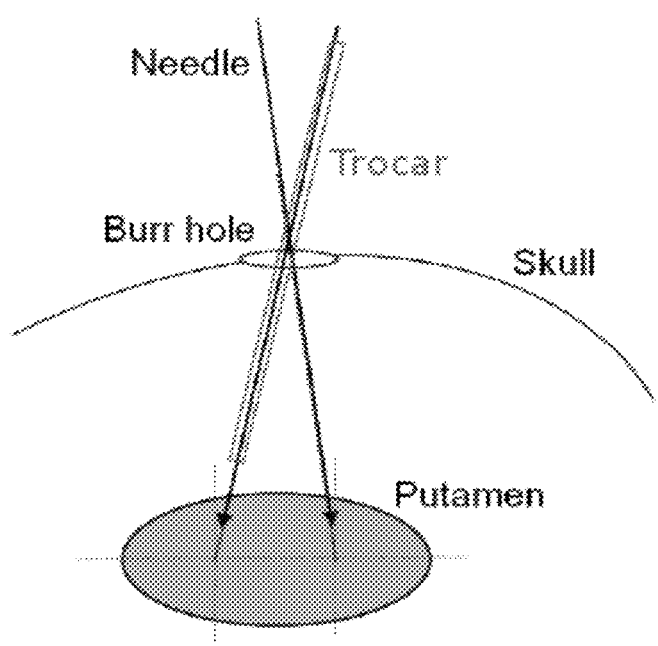
FIG. 4: Schematic Drawing of a Stereotactic Arrangement for Bilateral Injection into the Putamen.
Figure 5:
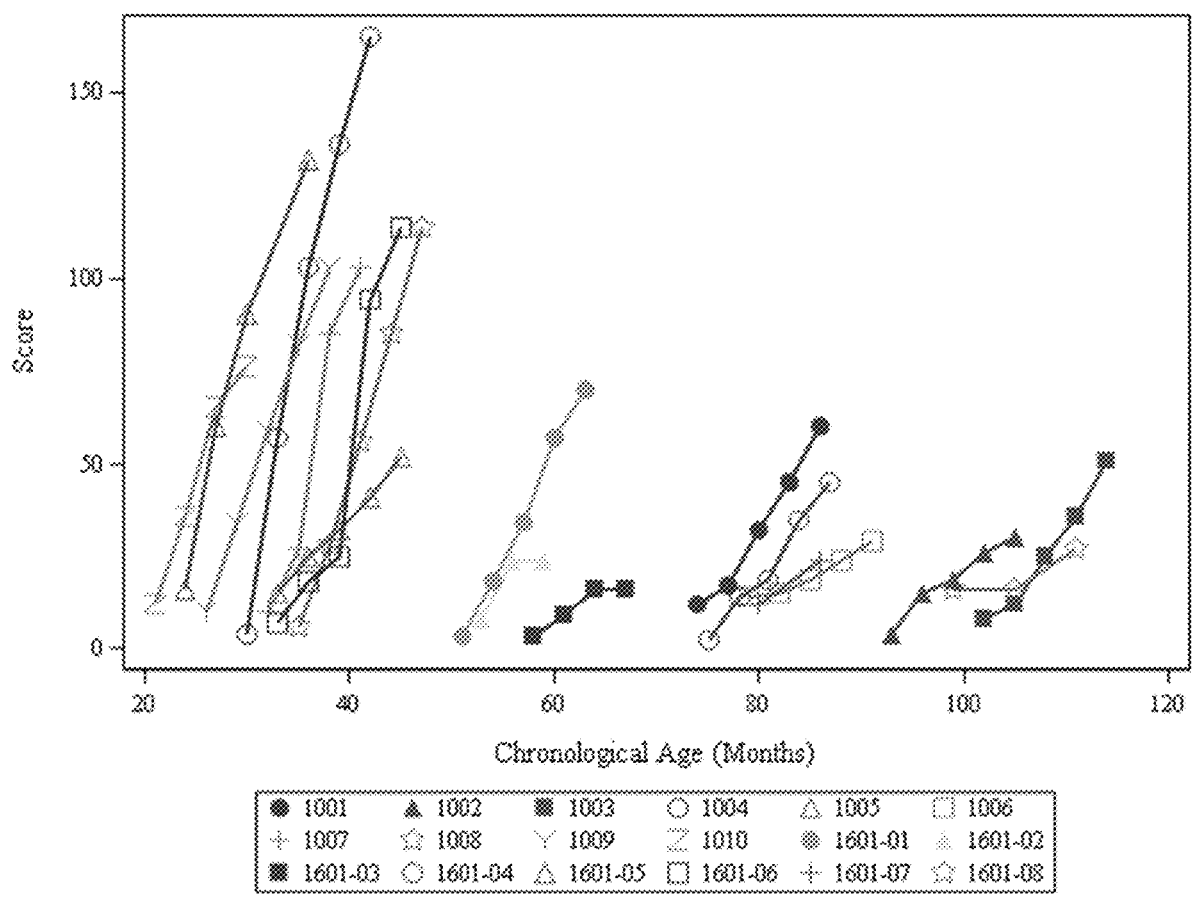
FIG. 5: Graphical representation of PDMS-2 Total Raw Scores by Subject and Chronological Age (n=18).

3) Swaged Catheter Components: Stainless Steel; Polyimide Tubing (delivers vector solution); Medical Adhesive; Teflon and "Heat-Shrink" Tubing; Microliter Syringe (e.g., Hamilton Syringe, Model 1750 TLL (500 µL)). (FIG. 4)

5) Syringe pump: Harvard Pump 11 Elite Nanomite Programmable Syringe Pump.

Device Description

Vector is delivered by a swaged catheter that is inserted in a prepositioned insertion tube. An insertion tube containing a solid stylet is accurately inserted in a surgery guided by previously-done Mill and CT scans. The insertion tube and stylet are provided in the Medtronic Nexframe® Stereotactic System. Prior to infusion, the catheter and syringe are attached and loaded with vector. The stylet is removed from the insertion tube and the swaged catheter is introduced in its place. The lengths of the insertion tube and catheter allow the catheter to extend 20 mm beyond the sleeve when fully seated. The vector solution is precisely administered by a syringe pump connected to the Hamilton syringe. The tubing between the catheter and syringe is 100 cm long and flexible enough that the placement of the catheter can be almost totally independent of the position of the syringe and Harvard syringe pump.

Example 1

Clinical Study of High Dose AADC Gene Therapy

Eighteen children (~2 to ~9 years of age) with severe AADC deficiency were treated with rAAV2-hAADC vector under two clinical studies authorized by the Taiwan FDA (TFDA). Bilateral injections of rAAV2-hAADC vector into the putamen via an established stereotactic procedure have resulted in remarkable improvements in motor control and achievement of developmental milestones in many of the children.

A pharmaceutical formulation comprising rAAV2-hAADC vector at a concentration of $5.7 \times 10^{11}$ vg/mL is injected directly into the putamen bilaterally via stereotactic procedure using a commercially available NeXframe (Medtronic) skull-mounted platform guided by the Stealthstation® Treon Navigation System (Medtronic), rAAV2-hAADC vector is administered at a dose volume of 80 µL per site to four sites (two per putamen) at a total dose of $1.8 \times 10^{11}$ vector genomes (vg) and a total volume of 320 µL.

Gene therapy was administered using an established stereotactic surgical technique employed in deep brain stimulation (DBS). DBS is an established neurosurgical procedure, with most of its applications in Parkinson's disease. Surgery was performed under general anesthesia.

As useful in gene transfer surgery, an injection catheter was used instead of the electronic lead used in DBS. Usefully the injection catheter was inserted after the placement of the insertion tube into the brain. A NeXframe skull-mounted platform using bone fiducial markers was developed specifically to provided precise targeting stability during frameless trajectory-based procedures. The application of the frameless system allowed the ability to perform the operation in children.

Before surgery, magnetic resonance imaging (MRI) was performed, 8 stainless steel self-tapping fiducials were then screwed into the skull in a generally circular pattern, avoiding regions where the skull bones are too thin or fragile. A computed tomography (CT) scan was then performed. Using fused MRI and CT images, the trajectories for the infusion were planned. Reference is made to G. H. Barnett et al., "Frameless stereotaxy with scalp-applied fiducial markers for brain biopsy procedures: experience in 218 cases" *Journal of Neurosurgery*, 1999, 91(4) 569-576.

The rAAV2-hAADC vector was injected via a two-track insertion route (two injections per putamen). Without being bound by theory, employing a multiple infusion point strategy, administering vector bilaterally to both putamen, promotes even transduction of the gene to each putamen. The stereotactic surgery was guided by the Stealthstation® Treon Navigation System.

Study AADC-1601: Eight children with severe AADC deficiency were enrolled and treated. Children enrolled in the study had a diagnosis of AADC deficiency, defined as decreased HVA and 5-HIAA CSF levels, presence of at least one AADC gene mutation, and presence of clinical symptoms. Patients were followed monthly for safety assessments and every 3 months for efficacy assessments through the first year after surgery. Patients returned for assessments every 6 months. The median age of patients at baseline was 54.0 months (range 24 to 99 months). The median age at diagnosis was 15 months (range 4.0 to 29.0 months). Five patients were >12 months of age at symptom onset. All patients were Asian-Other, and 5 were female. Seven patients had homozygous-founder mutation (IVS6+4A>T).

Study AADC 010: Ten children with severe AADC deficiency were enrolled and treated. Patients were followed for at least 1 year. Study enrollment required a diagnosis of AADC deficiency, defined as decreased HVA and 5-HIAA CSF levels, elevated L-dopa levels, presence of at least one AADC gene mutation, and presence of clinical symptoms. Patients were followed monthly for safety assessments and every 3 months for efficacy assessments through the first year after surgery. The median age of patients at baseline was 34.0 months (range 21 to 102 months). The median age at diagnosis was 10.0 months (range 6.0 to 12.0 months). Five patients were ≤6 months of age, and 5 patients were ≤12 months of age at symptom onset. Nine patients were Asian-Chinese and 1 was White; the genders were balanced (5 patients each). Six patients had homozygous-founder mutation (IVS6+4A>T).

A recombinant AAV type 2 vector, rAAV2-hAADC, was used in this study. Nucleotide sequence of a pAAV-CMV-hAADC-KanR plasmid (SEQ ID NO. 1) was used in the manufacture of the rAAV2-hAADC vector. The expression cassette consisted of a cytomegalovirus immediate-early promoter followed by the first intron of human growth hormone, human AADC cDNA, and the simian virus 40 polyadenylation signal sequence. Clinical-grade rAAV2-hAADC was manufactured, and quality control was tested in compliance with the current Good Manufacturing Practices. All patients received infusions of the vector into two target points of each putamen by stereotactic surgery. The study was conducted in compliance with the Taiwan Guidelines on Gene Therapy.

Stereotactic Infusion:

The stereotactic surgery was guided by the StealthStation Treon Navigation System (Medtronic). Two target points that were sufficiently distant from each other in the dorsolateral direction, as confirmed by CT and MM, were determined for each putamen. One burr hole was trepanned in each side of the cranial bone, and the vector was injected via a two-track insertion route. The vector-containing solution was prepared at a concentration of $5.7 \times 10^{11}$ vg/ml, and 80 µL of the solution was injected at a rate of 3 µl/min into each target; the patient received $1.8 \times 10^{11}$ vg of AAV2-hAADC in total. During the surgery, a guide tube was inserted 2 cm from the target point, located at the middle of the depth of putamen. The stylet was removed, and a long catheter was then inserted to perform the infusion. During the in-fusion, the catheter was withdrawn slightly so that the vector could be distributed along a catheter tract of 6 to 8 mm in length.

Developmental Evaluation:

The AIMS, PDMS-II, and CDIIT scales were used to evaluate the motor development of the patients. The AIMS scale is an observational measure of infant motor performance that can be administered from birth through the age at which independent walking occurs. It assesses the sequential development of motor milestones. The PDMS-II scale is a skill-based measure of gross and fine motor development for infants and children from 6 months to 6 years of age that consists of four gross motor and two fine motor subtests. The CDIIT scale is a validated tool that is designed for infants and children in Taiwan; it is composed of five subtests (cognition, language, motor, social, and self-help). The scores were rated by a specially trained physical therapist, and the whole process was videotaped. The videos were then evaluated by a blinded clinician to decrease any possible bias.

Pet Study:

AADC expression in the putamen was assessed by PET with FDOPA, which is a substrate for AADC, before surgery and 6 months after the gene transfer. None of the patients took oral carbidopa, a peripheral AADC inhibitor, because they had deficient AADC activity. For the PET study, FDOPA (0.27 mCi/kg, 10 MBq/kg) in saline was infused into the antecubital vein, and a 15-min static acquisition in the three-dimensional mode was obtained 90 min after the tracer injection. The PET and CT imaging data were acquired and co-registered with a GE PET/CT scanner (Discovery ST-16; GE Healthcare) to produce the fusion images. The amounts of FDOPA radioactivity observed in the putamen and occipital lobe were calculated as SUVmax with the Xelerix software version 1.1362 (GE Healthcare). The standardized uptake value (SUV) is defined as tissue radioactivity concentration divided by the injected dose divided by the patient weight. SUVmax is the maximum value of SUV in the region of interest drawn around the targeted tissue, that is, the putamen and occipital lobe. Given that there is very little AADC enzyme in the occipital lobe, we used the occipital lobe as a measure of nonspecific background radioactivity. The specific putaminal FDOPA uptake was expressed as the ratio of FDOPA radioactivity in the combined (right and left) putamen (minus non-specific FDOPA uptake by the occipital lobe) to the radioactivity in the occipital lobe, according to the following formula: (putamen−occipital lobe)/occipital lobe.

Analyses of CSF Neurotransmitter Metabolites and Serum Anti-AAV2 Titers:

The levels of HVA, HIAA, and 3-O-methyldopa in the CSF were measured by high-performance liquid chromatography (HPLC) at Medical Neurogenetics. We also measured the L-DOPA levels in the CSF by HPLC (26). The serum levels of antibodies against AAV2 were determined with an enzyme-linked immunosorbent assay (ELISA) (27). The ELISA method used in this study was developed for the rapid screening of neutralizing antibodies (nAbs). Using whole vector particles as antigens without degradation, we assessed antibodies that were more specific for AAV2, including nAbs. The antibody titers assessed by this ELISA method showed a good correlation with the nAb titers obtained in a previous cell transduction assay.

Family Questionnaire:

To document the symptoms that were more difficult to quantify, parents of the patients were asked to fill out a questionnaire at the end of the study to compare the status before and after the gene transfer. The questionnaire contained four items: mood, as a percentage of time in a good versus a bad mood in a day; sweating, in which the scores of 1 to 3 indicated normal, increased, and excessive sweating, respectively; body temperature, in which the scores of 1 to 3 indicated stable, occasionally unstable, and frequently unstable, respectively; and the severity of the oculogyric crisis, where scores of 1 to 3 indicated mild, moderate severe, and very severe, respectively.

Efficacy:

Peabody Developmental Motor Scale 2: The integrated analyses of PDMS 2 total and sub scale raw scores in studies AADC 1601 and AADC 010 demonstrate statistically significant improvement in gross and fine motor skills as early as 6 months after gene therapy. The increase in PDMS 2 total score was driven by statistically significant increases in 4 (Stationary, Locomotion, Grasping, and Visual-Motor Integration) of the 6 subtests. The significant treatment benefit seen on motor skills generally continued to improve over time. Younger children showed a greater treatment benefit than older children after surgery.

Figure 6:
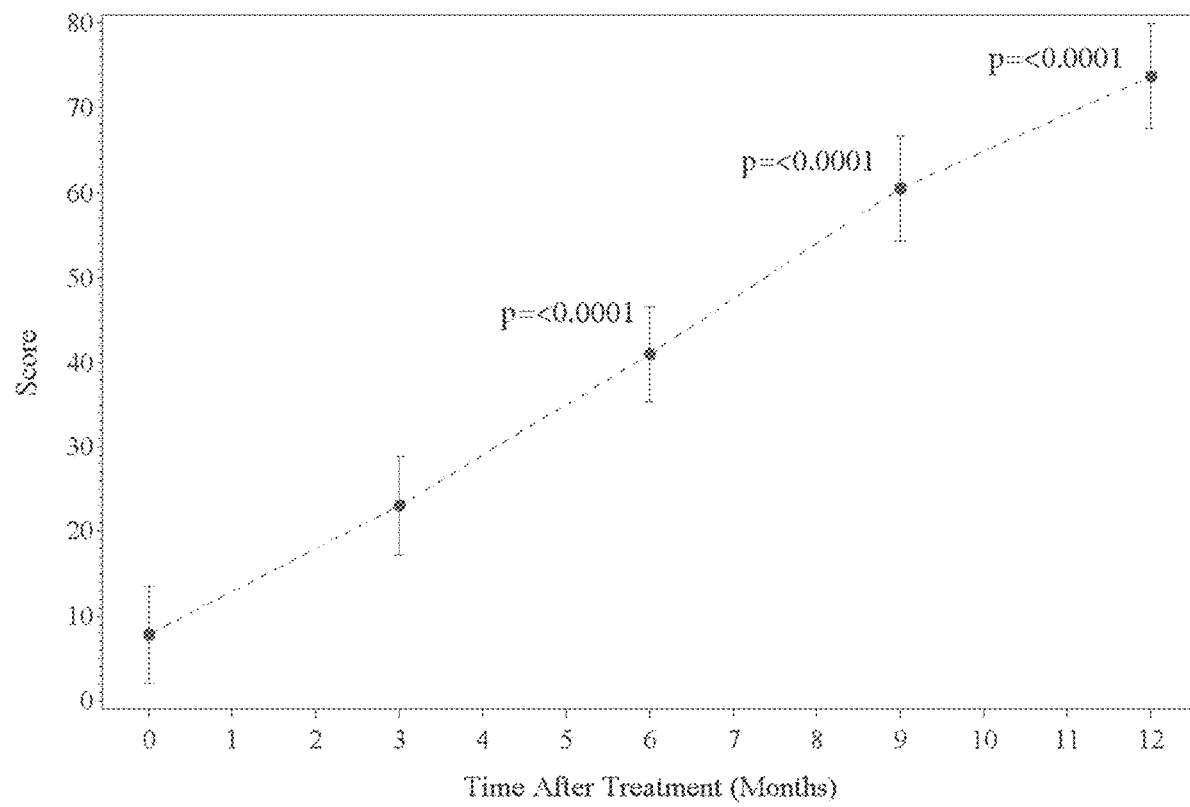
FIG. 6: Graphical representation of LS means and SE for PDMS total score over time through 12 months after vector administration (n=18).

PDMS-2 Total Score: After surgery, patients demonstrated generally continuous increases in their PDMS 2 total score (FIG. 6). The least squares (LS) mean PDMS total score over time through 12 months after the procedure is shown graphically in (FIG. 7). The increase in LS mean PDMS 2 total score was evident as early as 3 months after the procedure. The increases from baseline in LS mean PDMS 2 total score improved over time and achieved statistical significance by 6 months after the procedure (Table 2). Age at the time of the procedure was a significant factor in the model with younger patients at baseline showing the greatest increases in PDMS 2 total score (Table 3).

TABLE 1

Repeated Measures Model for PDMS-2 Total Score-LS Means by Time Point (All Patients n = 18)

| Time Point | LS Mean (SE) | 95% CI for Mean | Unadjusted P-value[1] | Adjusted P-value[2] |
|---|---|---|---|---|
| Baseline | 7.8 (5.66) | −3.5, 19.2 | | |
| 3 months | 23.0 (5.83) | 11.3, 34.7 | 0.0260 | 0.10410 |
| 6 months | 41.0 (5.53) | 29.9, 52.1 | <0.0001 | <0.0001 |
| 9 months | 60.5 (6.18) | 48.1, 72.9 | <0.0001 | <0.0001 |
| 12 months | 73.7 (6.14) | 61.4, 86.0 | <0.0001 | <0.0001 |

[1]Two-sided p-value for testing H0: Mean Score-Baseline Score = 0 at each postbaseline time point.
[2]Adjusted p-value = min(x * (p-value), 1.0), based on the Bonferroni adjustment.
CI = confidence interval; LS = least squares; PDMS-2 = Peabody Developmental Motor Scale, Second Edition; SE = standard error.

TABLE 3

Repeated Measures Model for PDMS-2 Total Score-Tests of Fixed Effects (All Patients n = 18)

| Fixed Effect | Numerator DF | Denominator DF | F-value | P-value[1] |
|---|---|---|---|---|
| Study ID | 1 | 15.22 | 0.82 | 0.3793 |
| Visit | 4 | 58.25 | 29.99 | <0.0001 |
| Age at gene therapy (months) | 1 | 14.92 | 16.98 | 0.0009 |

[1]P-value for testing the significance of each fixed effect in the model.
DF = degrees of freedom; ID = identity; LS = least squares; PDMS-2 = Peabody Developmental Motor Scale, Second Edition.

Alberta Infant Motor Scale (AIMS): The integrated analyses of AIMS total and sub scale raw scores in studies AADC 1601 and AADC 010 demonstrate clinically and statistically significant improvement motor function after surgery. Increases in AIMS scores were evident as early as 3 months after the procedure and improved continuously over a period of 12 months. Significant treatment benefit on the Prone, Supine, and Sit subtest scores contributed to the overall significant treatment benefit on the AIMS total score. Younger children show the most pronounced treatment benefit on from surgery.

AIMS Total: After surgery, all patients in the integrated group demonstrated generally continuous increases in their AIMS total score (FIG. 7). The LS mean AIMS total score over time through 12 months after the procedure is shown graphically in FIG. 8. The increase in LS mean AIMS total score was evident as early as 3 months after the procedure. The increases from baseline in LS mean AIMS total score improved over time and achieved statistical significance by 6 months after the procedure (Table 4). Age at the time of the procedure was a significant factor in the model with younger patients at baseline showing the greatest increases in AIMS total score (Table 5).

TABLE 4

Repeated Measures Model for AIMS Total Score-LS Means by Time Point (All Patients n = 18)

| Time Point | LS Mean (SE) | 95% CI for Mean | Unadjusted P-value[1] | Adjusted P-value[2] |
|---|---|---|---|---|
| Baseline | 1.5 (1.81) | −2.1, 5.2 | | |
| 3 months | 5.3 (1.72) | 1.8, 8.8 | 0.0629 | 0.25157 |
| 6 months | 10.1 (1.68) | 6.7, 13.4 | <0.0001 | 0.00020 |
| 9 months | 14.2 (1.82) | 10.5, 17.8 | <0.0001 | <0.0001 |
| 12 months | 16.9 (1.86) | 13.2, 20.6 | <0.0001 | <0.0001 |

[1]Two-sided p-value for testing H0: Mean Score-Baseline Score = 0 at each postbaseline time point.
[2]Adjusted p-value = min(x * (p-value), 1.0), based on the Bonferroni adjustment.
AIMS = Alberta Infant Motor Scale; CI = confidence interval; LS = least squares; SE = standard error.

TABLE 5

Repeated Measures Model for AIMS Total Score-Tests of Fixed Effects (All Patients n = 18)

| Fixed Effect | Numerator DF | Denominator DF | F-value | P-value[1] |
|---|---|---|---|---|
| Study ID | 1 | 15.62 | 0.13 | 0.7255 |
| Visit | 4 | 58.67 | 18.76 | <0.0001 |
| Age at gene therapy (months) | 1 | 14.90 | 12.54 | 0.0030 |

[1]P-value for testing the significance of each fixed effect in the model.
AIMS = Alberta Infant Motor Scale; DF = degrees of freedom; ID = identity.

Figure 9:
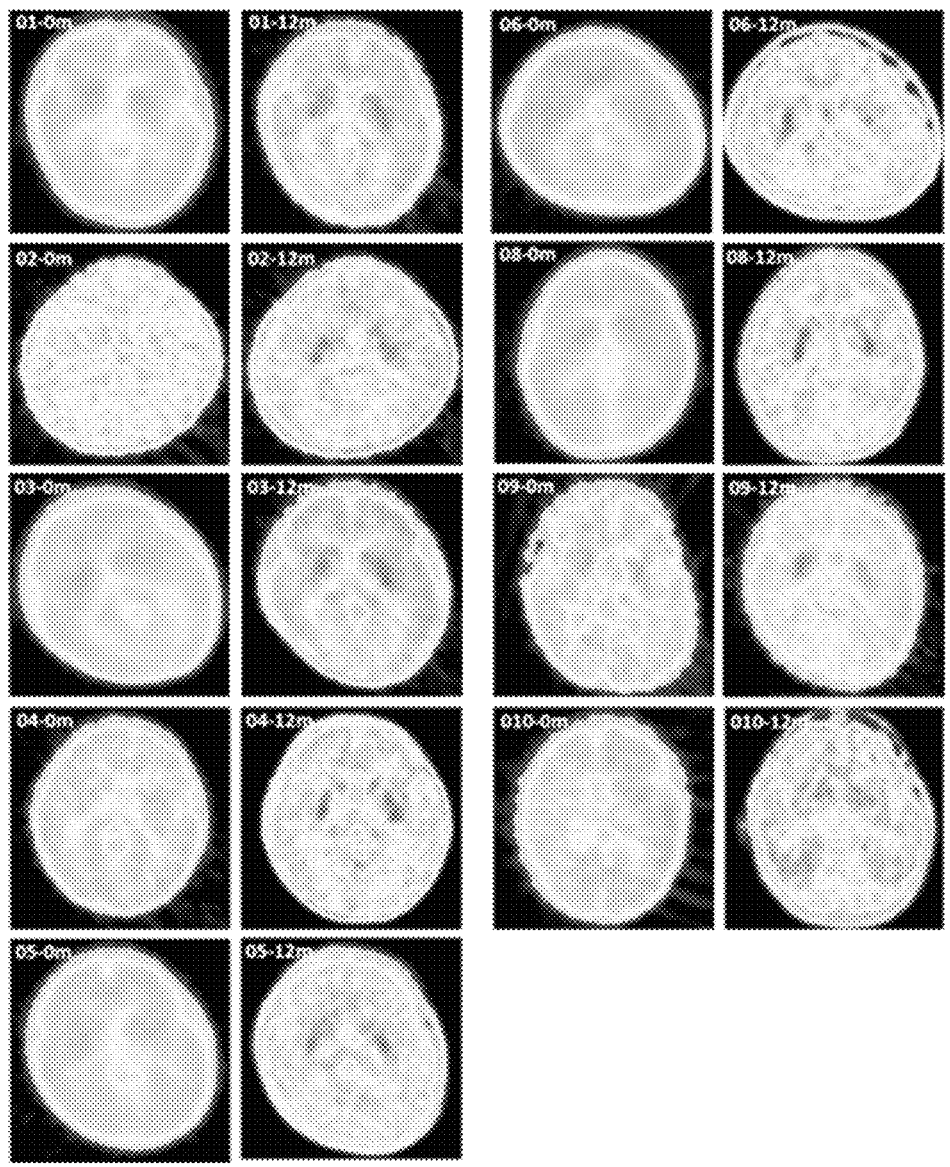
FIG. 9: Images of $^{18}$F-DOPA PET before and after gene therapy treatment.
Figure 10:
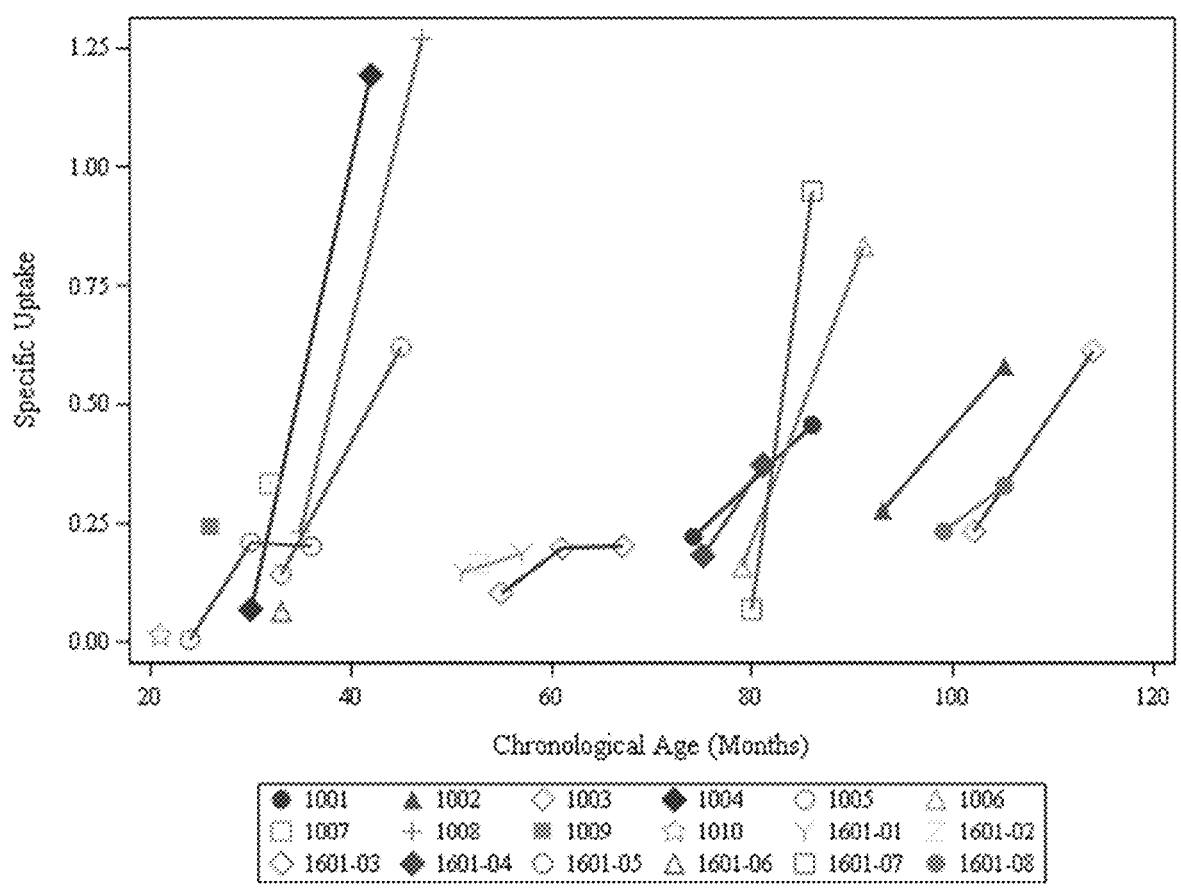
FIG. 10: Graphical representation of LS mean PET specific uptake over time through 12 months after gene therapy treatment.
Figure 11:
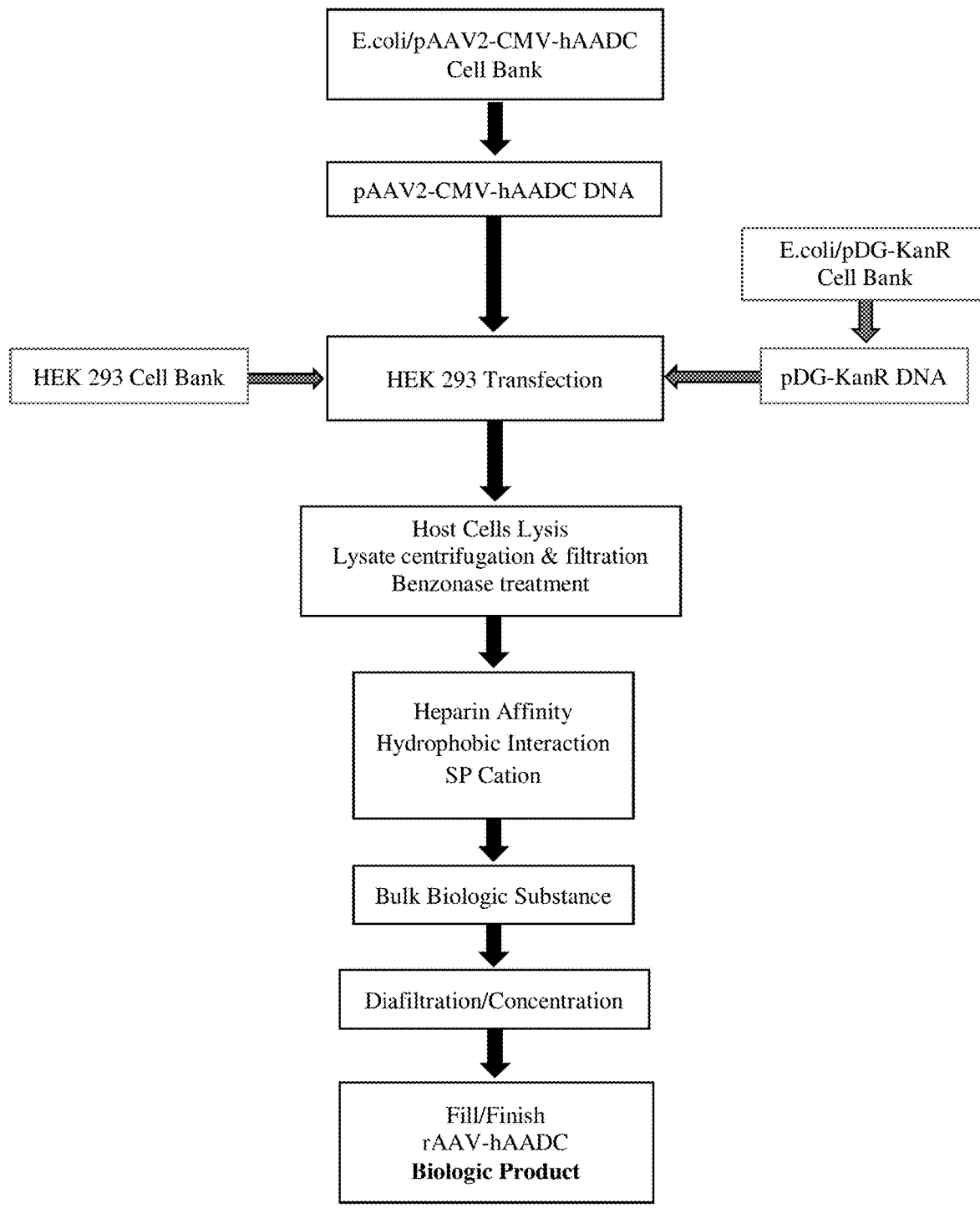
FIG. 11: Schematic Overview of a rAAV-hAADC Vector Manufacturing Process.
Figure 12:
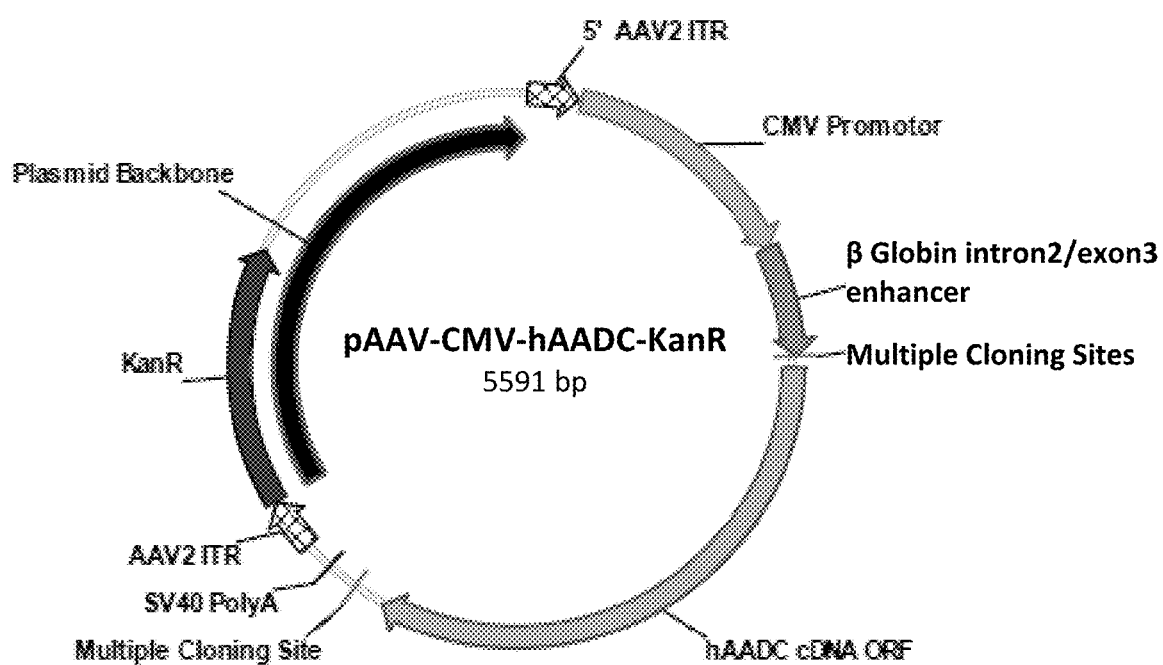
FIG. 12: Schematic Plasmid Map of pAAV-CMV-hAADC-KanR DNA.

$^{18}$F-DOPA Positron Emission Tomography (PET):

Analysis of the SUV demonstrated reproducible increases in $^{18}$F-DOPA uptake in the putamen following gene therapy treatment. Signals prior to gene therapy were uniformly low in untreated patients. Following gene therapy, $^{18}$F-DOPA PET signals increased in Study AADC 1601 at 6 months in 5 of 6 right putaminal measurements and 5 of 6 left putaminal measurements, and at 60 months in 10 of 10 right plus left putamen measurements. $^{18}$F-DOPA PET signals increased in Study AADC 010 at 12 months in 8 of 8 patients for whom measurements were available. Representative images are shown in FIG. 9. After administration of the AAV2-hAADC viral vector, most patients in the integrated group demonstrated generally continuous increases in PET specific uptake. The LS mean PET specific uptake over time through 12 months after the procedure is shown graphically in FIG. 10. A statistically significant increase in LS mean PET specific uptake was evident as early as 6 months and further increased by 12 months after the procedure.

Conclusions:

Bilateral injection of rAAV-hAADC vector into the putamen resulted in demonstrable and enduring improvements in motor control and achievement of developmental milestones in children with severe AADC. After surgery, patients demonstrated continuous increases in their PDMS 2 total scores indicating improvement in motor function. In an integrated analysis of both studies, improvement on the PDMS 2 total score was evident by 3 months after surgery and achieved statistical significance by 6 months after treatment. The results of the AIMS analysis were similar, with patients showing improvement in motor function from baseline that achieved statistical significance by 3 months after surgery. Results demonstrate that children with severe AADC deficiency who are treated early show a greater treatment benefit than older children at the time of surgery.

Example 2

A Phase I/II Trial of Gene Therapy for an Inherited Disorder of Monoamine Neurotransmitter Deficiency Intraputaminal injection of rAAV2-hAADC vector, in a compassionate use program, resulted in improvements in the motor function of patients with AADC deficiency. A phase VII trial enrolled 10 AADC deficiency patients (1.7 to 8.4 years) with bilateral intraputaminal injection of rAAV2-hAADC vector. All stereotactic surgeries and vector injections were well tolerated. Patients started to move their arms and mouths 2-3 weeks after gene transduction, and new motor skills were observed 2-3 months later. At 12 months after gene transduction, all but one patient had improvements in motor scales, showed increase in cerebral spinal fluid neurotransmitter concentrations, and increase in tracer uptake in FDOPA PET. Anti-AAV2 antibody titers rose in all patients. But titers decreased a few months after gene transduction. There were no signs of cerebral or systemic immune reaction during the follow up period. Adverse events related to treatment were generally well tolerated, including events associated with the surgery or transient post-gene transduction dyskinesia. One patient died of influenza B encephalopathy 10 months after gene transduction, but his 9-month motor scales had shown improvement. Preliminary evidence showed more substantial improvements in motor and cognitive function in the youngest patients treated. In conclusion, rAAV2-hAADC gene therapy is a potential treatment for an inherited brain neurotransmitter deficiency, and treatment at a younger age may be associated with a better outcome.

Example 3

Gene Therapy for Aromatic L-Amino Acid Decarboxylase Deficiency: 5 Years after rAAV2-hAADC Transduction Injection of rAAV2-hAADC vector bilaterally (i.e., to both putamens of subjects) with AADC deficiency resulted in improvements in patients' motor function. Data was obtained from 5 patients who have been followed for more than 5 years after treatment. These patients did not have head control and had not achieved other major motor milestones prior to gene transduction, but started to gain new motor skills after gene transduction. Motor development and cognitive function exhibited improvement over this 5-year period, with the most substantial gains observed during the first two years after gene transduction. At 5 years after gene transduction, FDOPA PET still exhibited signals of AADC activity over the putamens. Patients' anti-AAV2 antibody titers rose after gene transduction, peaked a few months later, and then decreased. There were no signs of cerebral or systemic immune reaction during the follow up period. Therefore, treatment with rAAV2-hAADC demonstrates encouraging evidence of long-term safety and therapeutic efficacy for patients with AADC deficiency.

Example 4

Treatment of Post Gene-Transduction Dyskinesia

Patients who received gene-transduction for AADC deficiency experienced post gene-transduction dyskinesia characterized by symptoms including exaggerated and uncontrolled movements over the mouth, face, and extremities. Patients were evaluated from 1-3 months after gene transduction. Administration of risperidone, a suitable dopamine antagonist resulted in reduced or elimination of dyskinesia while allowing motor development.

Dose Regimen:
Risperidone (1 mg/mL oral solution) was administered 0.1 mL-0.2 mL twice daily (BID).

Patients in the Phase I/II trial: AADC001-AADC008:

AADC001: Patient received gene transduction at the age of 6 years. Dyskinesia occurred at 5 weeks after gene transduction. Dyskinesia increased thereafter. Risperidone was administered beginning at the 7th week. Dyskinesia remained high for 3 weeks and then went down. Medication stopped 12 weeks after gene transduction.

AADC002: Patient received gene transduction at the age of 7.5 years. Risperidone treatment started when dyskinesia occurred at 4 weeks after gene transduction. Dyskinesia became more prominent and the dosage of the medication was increased. Dyskinesia then decreased and the medication stopped 12 weeks after gene transduction.

AADC003: Patient received gene transduction at the age of 8.5 years. Risperidone treatment started when dyskinesia occurred at 5 weeks after gene transduction. Dyskinesia became more prominent and we needed to increase the dosage of the medication. Dyskinesia then decreased and the medication was stopped 10 weeks after gene transduction.

AADC004: Patient received gene transduction at the age of 2.5 years. Dyskinesia was mild and transient. Patient did not receive dopamine antagonist treatment.

AADC005: Patient received gene transduction at the age of 2.5 years. Dyskinesia was mild and transient. Patient did not receive dopamine antagonist treatment.

AADC006: Patient received gene transduction at the age of 6.5 years. Risperidone treatment started when dyskinesia occurred at 6 weeks after gene transduction and interfered with the patient's swallowing. Dyskinesia became more prominent and the dosage of the medication increased twice. Dyskinesia then decreased and the medication stopped 10 weeks after gene transduction.

AADC007: Patient received gene transduction at the age of 2.5 years. Dyskinesia was mild. Risperidone treatment started at the 6th week and stopped 8 weeks after gene transduction.

AADC008: Patient received gene transduction at the age of 3 years. Dyskinesia was moderate. Risperidone treatment started at the 4th week, increasing the dose once, and stopped treatment 8 weeks after gene transduction.

Patients in the compassionate use trial: CU001-CU008 (In this early study, the dopamine antagonist treatment used to treat post-gene transduction dyskinesia was not planned. Only patients CU003 & CU008 received dopamine antagonist treatment.

CU001: Patient received gene transduction at the age of 4 years. Patient's post gene-transduction dyskinesia, occurred 2-3 months after gene transduction, was mild. Orofacial dyskinesia seemed to induce nausea, and the parents had given the patient anti-emetic agents.

CU002: Patient received gene transduction at the age of 4.5 years. Orofacial dyskinesia started one month after gene transduction which sometimes interfered with his saliva swallowing. For one month, his condition was difficult due to choking and infection. At two months after gene transduction, his tongue movement was still exaggerated, but the interference on saliva swallowing decreased. Orofacial and limb dystonia persisted for a few months, but his general condition was stable. The parents didn't bring him back to the clinic after the one-year clinical trial period.

CU003: Patient received gene transduction at the age of 4.5 years. Orofacial dyskinesia disturbed her saliva swallowing one month after gene transduction. The parents needed to aspirate her saliva almost every several minutes, and feeding was administrated through NG and sleep was poor. Anti-emetic medication was not effective on her dyskinesia. Risperidone was prescribed. The dose was increased over two weeks. This medication was effective and choking by saliva decreased. However, her movements over the extremities were also suppressed, so we needed to stop this medication. The suppressive effect lasted for a month after the last dosing. Three months after gene transduction, her motor movements returned gradually. Orofacial dyskinesia persisted for 5 months.

CU004: Patient received gene transduction at the age of 6 years. Orofacial dyskinesia started one month after gene transduction but was not serious. No specific medication was given. Three months after gene transduction, she could eat semi-liquid foods by mouth.

CU005: Patient received gene transduction on at the age of 2 years. Dyskinesia occurred one month after gene transduction, but was mild: some mouth movements and intermittent choreoathetoid movements of extremities. The dyskinesia was self-limited and no specific managements were given.

CU006: Patient received gene transduction, at the age of 2.5 years. 3 weeks after gene transduction, she had choreoathetoid movements of the mouth and fingers. Dyskinesia became most severe 6 weeks after gene transduction, which interfered with her sleep and swallowing. The severity of dyskinesia then decreased and no specific medication was given to her.

CU007: Patient received gene transduction at the age of 6.5 years. His general condition was very poor, and he had tracheostomy, gastrostomy, and anemia (parents refuse transfusion).

CU008: Patient received gene transduction on at the age of 8 years. Orofacial dyskinesia appeared one month after gene transduction, and Risperidone was prescribed. Dyskinesia increased a little bit thereafter, and then decreased. The medication was used for only two weeks.

Example 5

Age-Determined Dose Treatment with rAAV2-hAADC Vector

Using frameless stereotaxy, 80 μL of rAAV2-hAADC is injected into four target points in a patient's putamen at a rate of 3 μL/min, where the rAAV2-hAADC has a concentration of $5.7 \times 10^{11}$ vg/mL. A total of $1.8 \times 10^{11}$ vg of the viral vector is injected.

The AAV viral vector delivers AADC genes into putamens in striatums of two AADC deficiency patients. The first patient is a 4-year-old girl who had profound hypotonia and lack of any motor development. After the treatment, activities of the limbs are increased, control of the limbs is improved and recognition is enhanced. The girl can sit well without support with good head control and touch things with her hands one year after the treatment. The second patient is a 3.5-year-old boy. Two months after the treatment, activities of the limbs are increased and control of the trunk is also improved. In conclusion, the present disclosure uses the AAV viral vectors to transfer AADC genes for treating AADC deficiency practically and effectively.

Example 6

Treatment with High Dose rAAV2-hAADC Vector

Six children with severe AADC deficiency are enrolled and treated. Children enrolled in the study have a diagnosis of AADC deficiency, defined as decreased HVA and 5-HIAA CSF levels, presence of at least one AADC gene mutation, and presence of clinical symptoms. Patients are followed monthly for safety assessments and every 3 months for efficacy assessments through the first year after surgery. Patients return for assessments every 6 months. The six children have homozygous-founder mutation (IVS6+ 4A>T).

Using frameless stereotaxy, 80 μL of rAAV2-hAADC are injected into four target points in a patient's putamen (320 μL total) at a rate of 3 μL/min, where the rAAV2-hAADC has a concentration of $7.5 \times 10^{11}$ vg/mL. A total of $2.4 \times 10^{11}$ vg of the viral vector is injected.

Integrated analyses of PDMS-2 total and subscale raw scores demonstrate statistically significant improvement in gross and fine motor skills as early as 6 months after gene therapy. An increase in PDMS-2 total score is driven by statistically significant increases in 4 (Stationary, Locomotion, Grasping, and Visual-Motor Integration) of the 6 subtests. A significant treatment benefit seen on motor skills generally continues to improve over time. After surgery, patients demonstrate generally continuous increases in their PDMS-2 total score. The increase in LS mean PDMS-2 total score is evident as early as 3 months after the procedure. The increases from baseline in LS mean PDMS-2 total score improve over time and achieve statistical significance by 6 months after the procedure.

One patient is a 2-year-old girl who has profound hypotonia and lack of any motor development. After the treatment, activities of the limbs are increased, control of the limbs is improved and recognition is enhanced. The girl can sit well without support with good head control and touch things with her hands one year after the treatment. A second patient is a 1.5-year-old boy. Two months after the treatment, activities of the limbs are increased and control of the trunk is also improved. In conclusion, the present disclosure uses the AAV viral vectors to transfer AADC genes for treating AADC deficiency practically and effectively.

Example 7

Treatment with rAAV2-hAADC Vector and Empty Capsids

Using frameless stereotaxy, 80 μL of a pharmaceutical formulation comprising about $2.4 \times 10^{11}$ vg rAAV2-hAADC vector and about $1.76 \times 10^{12}$ empty capsids, is injected into four target points in a patient's putamen at a rate of 3 μL/min. The AAV viral vector delivers AADC genes into putamens in striatums of two AADC deficiency patients. Integrated analyses of PDMS-2 total and subscale raw scores demonstrate statistically significant improvement in gross and fine motor skills as early as 6 months after gene therapy. An increase in PDMS-2 total score is driven by statistically significant increases in 4 (Stationary, Locomotion, Grasping, and Visual-Motor Integration) of the 6 subtests. A significant treatment benefit seen on motor skills generally continues to improve over time. After surgery, patients demonstrate generally continuous increases in their PDMS-2 total score. The increase in LS mean PDMS-2 total score is evident as early as 3 months after the procedure. The increases from baseline in LS mean PDMS-2 total score improve over time and achieve statistical significance by 6 months after the procedure. The first patient is a 4-year-old girl who had profound hypotonia and lack of any motor development. After the treatment, activities of the limbs are increased, control of the limbs is improved and recognition is enhanced. The girl can sit well without support with good head control and touch things with her hands one year after the treatment. The second patient is a 5-year-old boy. Two months after the treatment, activities of the limbs are increased and control of the trunk is also improved. In conclusion, the present disclosure uses the AAV viral vectors to transfer AADC genes for treating AADC deficiency practically and effectively.

What is claimed is:

1. A method of treating aromatic L-amino acid decarboxylase (AADC) deficiency in a pediatric subject, the method comprising:
   (a) providing a pharmaceutical formulation comprising an rAAV2-hAADC vector comprising (i) a wild type AAV2 capsid, and (ii) a recombinant DNA dopa decarboxylase (DDC) gene insert comprising a nucleic acid sequence encoding hAADC; and
   (b) delivering the pharmaceutical formulation to at least one target site in the brain of the subject in a dose of an amount of at least $1.8 \times 10^{11}$ vg; wherein the pharmaceutical formulation further comprises empty AAV2 capsids at a percentage from about 50% cp/cp up to about 90% cp/cp, wherein the pharmaceutical formulation is delivered by stereotaxy.

2. The method of claim 1, wherein the dose is about $1.8 \times 10^{11}$ vg.

3. The method of claim 1, wherein the percentage of empty AAV2 capsids is at least about 75% cp/cp.

4. The method of claim 1, wherein the pediatric subject is less than about three years in age.

5. The method of claim 1, wherein the pediatric subject is about three or more years in age.

6. The method of claim 1, wherein the pediatric subject is human.

7. The method of claim 1, wherein the nucleic acid sequence encoding hAADC is an unmodified DDC cDNA.

8. The method of claim 1, wherein the recombinant DNA DDC gene insert comprises from 5' to 3' (i) a first inverted terminal repeat (ITR), (ii) a cytomegalovirus (CMV) immediate early promoter (IEP), (iii) a human β-globin partial intron2/exon 3, (iv) the nucleic acid sequence encoding hAADC, (v) a SV40 poly A tail, and (vi) a second ITR.

9. The method of claim 1, wherein the pharmaceutical formulation comprises the rAAV2-hAADC vector at a concentration of about $5.7 \times 10^{11}$ vg/mL.

10. The method of claim 1, wherein the pharmaceutical formulation is delivered by frameless stereotaxy.

11. The method of claim 1, wherein the pharmaceutical formulation is delivered at a rate of about 3 μL/min.

12. The method of claim 1, wherein the pharmaceutical formulation is delivered to the at least one target site at a dose volume of about 80 μL per target site.

13. The method of claim 1, wherein the pharmaceutical formulation is delivered to a putamen of the brain.

14. The method of claim 1, wherein the pharmaceutical formulation is delivered bilaterally to each putamen.

15. The method of claim 1, wherein the pharmaceutical formulation is delivered bilaterally to each putamen at target sites about 1 mm to about 10 mm apart.

* * * * *

SEQUENCE LISTING

<160> NUMBER OF SEQ ID NOS: 2

<210> SEQ ID NO 1
<211> LENGTH: 5591
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
tgacagatct gcgcgcgatc gatctgcgcg ctcgctcgct cactgaggcc gcccgggcgt      60
cgggcgacct ttggtcgccc ggcctcagtg agcgagcgag cgcgcagaga gggagtggcc     120
aactccatca ctaggggttc cttgtagtta atgattaacc cgccatgcta cttatctacg     180
tagccatgct ctagagcggc cgcacgcgta ctagttatta atagtaatca attacggggt     240
cattagttca tagcccatat atggagttcc gcgttacata acttacggta aatggcccgc     300
ctggctgacc gcccaacgac ccccgcccat tgacgtcaat aatgacgtat gttcccatag     360
taacgccaat agggactttc cattgacgtc aatgggtgga gtatttacgg taaactgccc     420
acttggcagt acatcaagtg tatcatatgc caagtacgcc ccctattgac gtcaatgacg     480
gtaaatggcc cgcctggcat tatgcccagt acatgacctt atgggacttt cctacttggc     540
agtacatcta cgtattagtc atcgctatta ccatggtgat gcggttttgg cagtacatca     600
atgggcgtgg atagcggttt gactcacggg gatttccaag tctccacccc attgacgtca     660
atgggagttt gttttggcac caaaatcaac gggactttcc aaaatgtcgt aacaactccg     720
ccccattgac gcaaatgggc ggtaggcgtg tacggtggga ggtctatata agcagagctc     780
gtttagtgaa ccgtcagatc gcctggagac gccatccacg ctgttttgac ctccatagaa     840
gacaccggga ccgatccagc ctccgcggat tcgaatcccg gccgggaacg gtgcattgga     900
acgcggattc cccgtgccaa gagtgacgta agtaccgcct atagagtcta taggcccaca     960
aaaaatgctt tcttctttta atatactttt ttgtttatct tatttctaat actttcccta    1020
atctctttct ttcagggcaa taatgataca atgtatcatg cctctttgca ccattctaaa    1080
gaataacagt gataatttct gggttaaggc aatagcaata tttctgcata taaatatttc    1140
tgcatataaa ttgtaactga tgtaagaggt ttcatattgc taatagcagc tacaatccag    1200
ctaccattct ggtttttattt tatggttggg ataaggctgg attattctga gtccaagcta    1260
ggcccttttg ctaatcatgt tcatacctct tatcttcctc ccacagctcc tgggcaacgt    1320
gctggtctgt gtgctggccc atcactttgg caaagaattg gattcgaac atcgattgaa    1380 ttccccgggg atccaccatg aacgcaagtg aattccgaag gagagggaag gagatggtgg    1440
attacgtggc caactacatg gaaggcattg agggacgcca ggtctaccct gacgtggagc    1500
ccgggtacct gcggccgctg atccctgccg ctgcccctca ggagccagac acgtttgagg    1560
```

-continued

```
acatcatcaa cgacgttgag aagataatca tgcctggggt gacgcactgg cacagcccct    1620
acttcttcgc ctacttcccc actgccagct cgtacccggc catgcttgcg gacatgctgt    1680
gcggggccat tggctgcatc ggcttctcct gggcggcaag cccagcatgc acagagctgg    1740
agactgtgat gatggactgg ctcgggaaga tgctggaact accaaaggca ttttgaatg     1800 agaaagctgg agaagggga ggagtgatcc agggaagtgc cagtgaagcc accctggtgg     1860
ccctgctggc cgctcggacc aaagtgatcc atcggctgca ggcagcgtcc ccagagctca    1920
cacaggccgc tatcatggag aagctggtgg cttactcatc cgatcaggca cactcctcag    1980
tggaaagagc tgggttaatt ggtggagtga aattaaaagc catcccctca gatggcaact    2040
tcgccatgcg tgcgtctgcc ctgcaggaag ccctggagag agacaaagcg gctggcctga    2100
ttcctttctt tatggttgcc accctgggga ccacaacatg ctgctccttt gacaatctct    2160
tagaagtcgg tcctatctgc aacaaggaag acatatggct gcacgttgat gcagcctacg    2220
caggcagtgc attcatctgc cctgagttcc ggcaccttct gaatggagtg gagttttgcag   2280 attcattcaa ctttaatccc cacaaatggc tattggtgaa ttttgactgt tctgccatgt    2340
gggtgaaaaa gagaacagac ttaacgggag cctttagact ggaccccact tacctgaagc    2400
acagccatca ggattcaggg cttatcactg actaccggca ttggcagata ccactgggca    2460
gaagatttcg ctctttgaaa atgtggtttg tatttaggat gtatggagtc aaaggactgc    2520
aggcttatat ccgcaagcat gtccagctgt cccatgagtt tgagtcactg gtgcgccagg    2580
atccccgctt tgaaatctgt gtggaagtca ttctggggct tgtctgcttt cggctaaagg    2640
gttccaacaa agtgaatgaa gctcttctgc aaagaataaa cagtgccaaa aaatccact    2700 tggttccatg tcacctcagg gacaagtttg tcctgcgctt tgccatctgt tctcgcacgg    2760
tggaatctgc ccatgtgcag cgggcctggg aacacatcaa agagctggcg gccgacgtgc    2820
tgcgagcaga gagggagtag gagtgaagcc agctgcagga atcaaaaatt gaagagagat    2880
atatctgaaa actggaataa gaagcaaata aatatcatcc tgccttcatg gaactcagct    2940
gtctgtggct tcccatgtct ttctccaaag ttatccagag ggttgtgatt ttgtctgctt    3000
agtatctcat caacaaagaa atattatttg ctaattaaaa agttaatctt catggccata    3060 gctttattc attagctgtg attttttgttg attaaaacat tatagatttt catgttcttg    3120
cagtcatcag aagtggtagg aaagcctcac tgatatattt tccagggcaa tcaatgttca    3180
cgcaacttga aattatatct gtggtcttca aattgtcttt tgtcatgtgg ctaaatgcct    3240
aataaggaat taattcgata tcaagctatc aacacactg gtagggataa cagggtaatc     3300
tcgaggcaag cttgggcccg gtacccaatt cgccctatag tgagtcgtat tacgcgcgca    3360
gcggccgacc atggcccaac ttgtttattg cagcttataa tggttacaaa taaagcaata    3420
gcatcacaaa tttcacaaat aaagcatttt tttcactgca ttctagttgt ggtttgtcca    3480
aactcatcaa tgtatcttat catgtctgga tctccggaca cgtgcggacc gagcggccgc    3540
tctagagcat ggctacgtag ataagtagca tggcgggtta atcattaact acaaggaacc    3600
cctagtgatg gagttggcca ctccctctct gcgcgctcgc tcgctcactg aggccgggcg    3660
accaaaggtc gcccgacgcc cgggctttgc ccgggcggcc tcagtgagcg agcgagcgcg    3720
cagatcagcg ctttaaattc agaagaactc gtcaagaagg cgatagaagg cgatgcgctg    3780
cgaatcggga gcggcgatac cgtaaagcac gaggaagcgg tcagcccatt cgccgccaag    3840
ctcttcagca atatcacggg tagccaacgc tatgtcctga tagcggtccg ccacacccag    3900
ccggccacag tcgatgaatc cagaaaagcg gccatttttcc accatgatat tcggcaagca    3960
```

```
ggcatcgcca tgggtcacga cgagatcctc gccgtcgggc atgctcgcct tgagcctggc    4020
gaacagttcg gctggcgcga gccctgatg ctcttcgtcc agatcatcct gatcgacaag    4080
accggcttcc atccgagtac gtgctcgctc gatgcgatgt tcgcttggt ggtcgaatgg    4140 gcaggtagcc ggatcaagcg tatgcagccg ccgcattgca tcagccatga tggatacttt    4200
ctcggcagga gcaaggtgag atgacaggag atcctgcccc ggcacttcgc ccaatagcag    4260
ccagtccctt cccgcttcag tgacaacgtc gagcacagct cgcaaggaa cgcccgtcgt    4320 ggccagccac gatagccgcg ctgcctcgtc ttgcagttca ttcagggcac cggacaggtc    4380
ggtcttgaca aaagaaccg gcgcccctg cgctgacagc cggaacacgg cggcatcaga    4440
gcagccgatt gtctgttgtg cccagtcata gccgaatagc ctctccaccc aagcggccgg    4500
agaacctgcg tgcaatccat cttgttcaat catgcgaaac gatcctcatc ctgtctcttg    4560
atcagatctt gatcccctgc gccatcagat ctttggcggc aagaaagcca tccagtttac    4620
tttgcagggc ttcccaacct taccagaggg cgccccagct ggcaattccg gttcgcttgc    4680
tgtccataaa accgcccagt ctagctatcg ccatgtaagc ccactgcaag ctacctgctt    4740
tctctttgcg cttgcgtttt cccttgtcca gatagcccag tagctgacat tcatccgggg    4800
tcagcaccgt ttctgcggac tggctttcta cgtgaaaagg atctaggtga agatccttt    4860 tgataatctc atgaccaaaa tcccttaacg tgagttttcg ttccactgag cgtcagaccc    4920
cgtagaaaag atcaaaggat cttcttgaga tccttttttt ctgcgcgtaa tctgctgctt    4980
gcaaacaaaa aaaccaccgc taccagcggt ggtttgtttg ccggatcaag agctaccaac    5040
tctttttccg aaggtaactg gcttcagcag agcgcagata ccaaatactg ttcttctagt    5100
gtagccgtag ttaggccacc acttcaagaa ctctgtagca ccgcctacat acctcgctct    5160
gctaatcctg ttaccagtgg ctgctgccag tggcgataag tcgtgtctta ccgggttgga    5220
ctcaagacga tagttaccgg ataaggcgca gcggtcgggc tgaacggggg gttcgtgcac    5280
acagcccagc ttggagcgaa cgacctacac cgaactgaga tacctacagc gtgagctatg    5340
agaaagcgcc acgcttcccg aagggagaaa ggcggacagg tatccggtaa gcggcagggt    5400
cggaacagga gagcgcacga gggagcttcc agggggaaac gcctggtatc tttatagtcc    5460
tgtcgggttt cgccacctct gacttgagcg tcgattttg tgatgctcgt caggggggcg    5520
gagcctatgg aaaaacgcca gcaacgcggc cttttacgg ttcctggcct tttgctggcc    5580
ttttgctcac a                                                        5591
```

<210> SEQ ID NO 2  
<211> LENGTH: 3703  
<212> TYPE: DNA  
<213> ORGANISM: Artificial Sequence  
<220> FEATURE:  
<223> OTHER INFORMATION: Description of Artificial Sequence: Synthetic polynucleotide

<400> SEQUENCE: 2

```
tctgcgcgct cgctcgctca ctgaggccgc ccgggcgtcg ggcgaccttt ggtcgcccgg      60
cctcagtgag cgagcgagcg cgcagagagg gagtggccaa ctccatcact aggggttcct     120
tgtagttaat gattaacccg ccatgctact tatctacgta gccatgctct agagcggccg     180
cacgcgtact agttattaat agtaatcaat tacgggtca ttagttcata gcccatatat     240
ggagttccgc gttacataac ttacggtaaa tggcccgcct ggctgaccgc ccaacgaccc     300
ccgcccattg acgtcaataa tgacgtatgt tcccatagta acgccaatag ggactttcca     360
```

```
ttgacgtcaa tgggtggagt atttacggta aactgcccac ttggcagtac atcaagtgta      420
tcatatgcca agtacgcccc ctattgacgt caatgacggt aaatggcccg cctggcatta      480
tgcccagtac atgaccttat gggactttcc tacttggcag tacatctacg tattagtcat      540
cgctattacc atggtgatgc ggttttggca gtacatcaat gggcgtggat agcggtttga      600
ctcacgggga tttccaagtc tccaccccat tgacgtcaat gggagtttgt tttggcacca      660
aaatcaacgg gactttccaa aatgtcgtaa caactccgcc ccattgacgc aaatgggcgg      720
taggcgtgta cggtgggagg tctatataag cagagctcgt ttagtgaacc gtcagatcgc      780
ctggagacgc catccacgct gttttgacct ccatagaaga caccgggacc gatccagcct      840
ccgcggattc gaatcccggc cgggaacggt gcattggaac gcggattccc cgtgccaaga      900
gtgacgtaag taccgcctat agagtctata ggcccacaaa aaatgctttc ttcttttaat      960
atactttttt gtttatctta tttctaatac tttccctaat ctctttcttt cagggcaata     1020
atgatacaat gtatcatgcc tctttgcacc attctaaaga ataacagtga taatttctgg     1080
gttaaggcaa tagcaatatt tctgcatata aatatttctg catataaatt gtaactgatg     1140
taagaggttt catattgcta atagcagcta caatccagct accattctgg ttttatttta     1200
tggttgggat aaggctggat tattctgagt ccaagctagg cccttttgct aatcatgttc     1260
atacctctta tcttcctccc acagctcctg ggcaacgtgc tggtctgtgt gctgcccat      1320 cactttggca aagaattggg attcgaacat cgattgaatt ccccggggat ccaccatgaa     1380
cgcaagtgaa ttccgaagga gagggaagga gatggtggat tacgtggcca actacatgga     1440
aggcattgag ggacgccagg tctaccctga cgtggagccc gggtacctgc ggccgctgat     1500
ccctgccgct gcccctcagg agccagacac gtttgaggac atcatcaacg acgttgagaa     1560
gataatcatg cctggggtga cgcactggca cagcccctac ttcttcgcct acttccccac     1620
tgccagctcg tacccggcca tgcttgcgga catgctgtgc ggggccattg gctgcatcgg     1680
cttctcctgg gcggcaagcc cagcatgcac agagctggag actgtgatga tggactggct     1740
cgggaagatg ctggaactac caaaggcatt tttgaatgag aaagctggag aaggggagg      1800 agtgatccag ggaagtgcca gtgaagccac cctggtggcc ctgctggccg ctcggaccaa     1860
agtgatccat cggctgcagg cagcgtcccc agagctcaca caggccgcta tcatggagaa     1920
gctggtggct tactcatccg atcaggcaca ctcctcagtg gaaagagctg ggttaattgg     1980
tggagtgaaa ttaaaagcca tcccctcaga tggcaacttc gccatgcgtg cgtctgccct     2040
gcaggaagcc ctgagagag acaaagcggc tggcctgatt cctttcttta tggttgccac      2100
cctggggacc acaacatgct gctcctttga caatctctta gaagtcggtc ctatctgcaa     2160
caaggaagac atatggctgc acgttgatgc agcctacgca ggcagtgcat tcatctgccc     2220
tgagttccgg caccttctga atggagtgga gtttgcagat tcattcaact ttaatcccca     2280
caaatggcta ttggtgaatt ttgactgttc tgccatgtgg gtgaaaaaga gaacagactt     2340
aacgggagcc tttagactgg accccactta cctgaagcac agccatcagg attcagggct     2400
tatcactgac taccggcatt ggcagatacc actgggcaga agatttcgct ctttgaaaat     2460
gtggtttgta tttaggatgt atggagtcaa ggactgcagg cttatatcc gcaagcatgt      2520 ccagctgtcc catgagtttg agtcactggt gcgccaggat ccccgctttg aaatctgtgt     2580
ggaagtcatt ctgggcttg tctgctttcg gctaaagggt tccaacaaag tgaatgaagc      2640
tcttctgcaa agaataaaca gtgccaaaaa aatccacttg gttccatgtc acctcaggga     2700
```

```
caagtttgtc ctgcgctttg ccatctgttc tcgcacggtg aatctgccc atgtgcagcg    2760 ggcctgggaa cacatcaaag agctggcggc cgacgtgctg cgagcagaga gggagtagga    2820
gtgaagccag ctgcaggaat caaaaattga agagagatat atctgaaaac tggaataaga    2880
agcaaataaa tatcatcctg ccttcatgga actcagctgt ctgtggcttc ccatgtcttt    2940
ctccaaagtt atccagaggg ttgtgatttt gtctgcttag tatctcatca acaaagaaat    3000
attatttgct aattaaaaag ttaatcttca tggccatagc ttttattcat tagctgtgat    3060
ttttgttgat taaaacatta tagattttca tgttcttgca gtcatcagaa gtggtaggaa    3120
agcctcactg atatattttc cagggcaatc aatgttcacg caacttgaaa ttatatctgt    3180
ggtcttcaaa ttgtcttttg tcatgtggct aaatgcctaa taaggaatta attcgatatc    3240
aagctatcca acacactggt agggataaca gggtaatctc gaggcaagct tgggcccggt    3300
acccaattcg ccctatagtg agtcgtatta cgcgcgcagc ggccgaccat ggcccaactt    3360
gtttattgca gcttataatg gttacaaata aagcaatagc atcacaaatt tcacaaataa    3420
agcatttttt tcactgcatt ctagttgtgg tttgtccaaa ctcatcaatg tatcttatca    3480
tgtctggatc tccggacacg tgcggaccga gcggccgctc tagagcatgg ctacgtagat    3540
aagtagcatg gcgggttaat cattaactac aaggaacccc tagtgatgga gttggccact    3600
ccctctctgc gcgctcgctc gctcactgag gccgggcgac caaaggtcgc ccgacgcccg    3660
ggctttgccc gggcggcctc agtgagcgag cgagcgcgca gat                      3703
```